(12) United States Patent
Neagu et al.

(10) Patent No.: US 8,895,599 B2
(45) Date of Patent: Nov. 25, 2014

(54) LIPOPROTEIN LIPASE-ACTIVATING COMPOSITIONS COMPRISING BENZENE DERIVATES

(71) Applicant: Otsuka Pharmaceutical Factory, Inc., Tokushima (JP)

(72) Inventors: Irina Neagu, Plainsboro, NJ (US); Michael Ohlmeyer, Plainsboro, NJ (US); Vidyadhar M. Paradkar, Somerville, NJ (US); Kurt W. Saionz, Cranford, NJ (US); Koushi Iwata, Tokushima (JP); Takashi Okamura, Tokushima (JP); Tadao Shibutani, Tokushima (JP)

(73) Assignee: Otsuka Pharmaceutical Factory, Inc., Naruto-shi (JP)

( * ) Notice: Subject to any disclaimer, the term of this patent is extended or adjusted under 35 U.S.C. 154(b) by 0 days.

(21) Appl. No.: 13/931,196

(22) Filed: Jun. 28, 2013

(65) Prior Publication Data
US 2013/0296342 A1 Nov. 7, 2013

Related U.S. Application Data

(62) Division of application No. 12/992,394, filed as application No. PCT/JP2008/059294 on May 14, 2008, now abandoned.

(51) Int. Cl.
| | | |
|---|---|---|
| A61K 31/415 | (2006.01) | |
| A61K 31/425 | (2006.01) | |
| A61K 31/519 | (2006.01) | |
| A61K 31/4164 | (2006.01) | |
| A61K 31/4184 | (2006.01) | |
| A61K 31/4188 | (2006.01) | |
| A61K 31/428 | (2006.01) | |
| A61K 31/4745 | (2006.01) | |
| C07D 233/58 | (2006.01) | |
| C07D 235/18 | (2006.01) | |
| C07D 277/66 | (2006.01) | |
| C07D 471/04 | (2006.01) | |
| C07D 487/04 | (2006.01) | |
| C07D 513/04 | (2006.01) | |
| A61K 31/429 | (2006.01) | |
| A61K 31/437 | (2006.01) | |
| C07D 233/56 | (2006.01) | |

(52) U.S. Cl.
CPC ............ *A61K 31/519* (2013.01); *C07D 233/56* (2013.01); *A61K 31/4164* (2013.01); *A61K 31/4184* (2013.01); *A61K 31/4188* (2013.01); *A61K 31/428* (2013.01); *A61K 31/4745* (2013.01); *C07D 233/58* (2013.01); *C07D 235/18* (2013.01); *C07D 277/66* (2013.01); *C07D 471/04* (2013.01); *C07D 487/04* (2013.01); *C07D 513/04* (2013.01); *A61K 31/429* (2013.01); *A61K 31/437* (2013.01)
USPC ........................ 514/397; 514/393; 514/368

(58) Field of Classification Search
CPC ..... C07D 233/56; C07D 233/58; C07D 231/12
USPC .............. 514/183, 368, 393, 397; 548/311.1, 548/343.5
See application file for complete search history.

(56) References Cited

U.S. PATENT DOCUMENTS

| | | | |
|---|---|---|---|
| 4,714,762 A | 12/1987 | Hoefle et al. | |
| 4,716,169 A | 12/1987 | Heider et al. | |
| 5,179,117 A | 1/1993 | Maduskuie, Jr. | |
| 8,329,739 B2 | 12/2012 | Shibutani et al. | |
| 2009/0075938 A1 | 3/2009 | Wynne et al. | |
| 2009/0176773 A1 | 7/2009 | Klussmann et al. | |
| 2010/0113412 A1 | 5/2010 | Zoller et al. | |
| 2011/0275823 A1 | 11/2011 | Shibutani et al. | |

FOREIGN PATENT DOCUMENTS

| | | |
|---|---|---|
| EP | 0113236 A1 | 7/1984 |
| EP | 0185345 A1 | 6/1986 |
| EP | 1964840 A1 | 9/2008 |
| JP | 07-291976 A | 11/1995 |
| JP | 2004525192 | 8/2004 |
| JP | 2006-182668 A | 7/2006 |
| WO | 01/27088 A1 | 4/2001 |
| WO | 2002092086 | 11/2002 |
| WO | 2006/122546 A1 | 11/2006 |
| WO | 2007/091106 A2 | 8/2007 |
| WO | 2008/029152 A2 | 3/2008 |

OTHER PUBLICATIONS

Ikuo Kawamura et al., "Effect of Lipoprotein Lipase Activators Bezafibrate and NO-1886, on B16 Melanoma-Induced Cachexia in Mice," *Anticancer Research*, 1999, 99: 4099-4104.

M. Kusunoki et al., "The lipoprotein lipase activator, NO-1886, suppresses fat accumulation and insulin resistance in rats fed a high-fat diet," *Diabetologia*, 2000, 43: 875-880.

(Continued)

*Primary Examiner* — My-Chau T Tran
(74) *Attorney, Agent, or Firm* — Sughrue Mion, PLLC

(57) ABSTRACT

The present invention provides pharmaceutical compositions containing benzene compound(s) represented by General Formula (1) below and, particularly, LPL-activating compositions for use in hyperlipidemia therapeutic and preventive agents, anti-obesity agents, and the like:

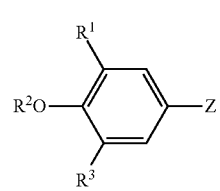

(1)

wherein $R^1$, $R^2$, $R^3$ and $R^4$ are as defined in the specification.

7 Claims, No Drawings

(56) References Cited

OTHER PUBLICATIONS

Kaori Nakayama et al., "Effect of the Lipoprotein Lipase activator NO-1886 on Adriamycin-Induced Nephrotic Syndrome in Rats," *Metabolism*, 2000, 49(5): 588-593.

Kazuhiko Tsutsumi et al., "Correction of Hypertriglyceridemia with Low High-Density Lipoprotein Cholesterol by the Novel Compound NO-1886, a Lipoprotein Lipase-Promoting Agent, in STZ-Induced Diabetic Rats," *Diabetes*, 1995, 44: 414-417.

Kazuhiko Tsutsumi et al., "Suppression of Hyperlipidemia-Associated Cataracts in Diabetic Rats with the Lipoprotein Lipase Activator NO-1886," *Biol. Pharm. Bull.*, 1996, 19(12): 1570-1573.

Kazuhiko Tsutsumi et al., "The Novel Compound NO-1886 Increases Lipoprotein Lipase Activity with Resulting Elevation of High Density Lipoprotein Cholesterol, and Long-term Administration Inhibits Atherogenesis in the Coronary Arteries of Rats with Experimental Atherosclerosis," *The Journal of Clinical Investigation*, 1993, 92: 411-417.

LIPOPROTEIN LIPASE-ACTIVATING COMPOSITIONS COMPRISING BENZENE DERIVATES

This is a divisional of U.S. patent application Ser. No. 12/992,394 filed Nov. 12, 2010, which is a 371 National Stage Entry of PCT/JP2008/059294 filed May 14, 2008, the contents of all of which are incorporated herein by reference in their entirety.

TECHNICAL FIELD

The present invention relates to compositions for activating lipoprotein lipase (hereinafter referred to as "LPL") and benzene compounds. The invention is further directed to the use of compounds activating LPL for preparing LPL-activating compositions, and a method for activating LPL using such compounds.

BACKGROUND CF THE INVENTION

Contemporary society is called a society of gluttony, and the number of people diagnosed with hyperlipidemia, obesity, etc., has been sharply rising. Hyperlipidemia, obesity and the like are extremely dangerous causing diabetes and arteriosclerosis that may result in cardiac infarction, cerebral infarction, and the like.

Accordingly, to prevent or treat hyperlipidemia, obesity, etc., a variety of research has been conducted on pharmaceuticals and chemotherapy for ameliorating pathological conditions of these diseases, for example, chemotherapy to activate LPL (lipoprotein lipase) and chemotherapeutic agents therefor. LPL activation is considered to be effective for preventing or treating hyperlipidemia, obesity, arteriosclerosis, cataract, cachexia, nephrosis, etc. Various publications describes the relationship between LPL activation and these diseases. For example, the relationship between LPL activation and arteriosclerosis is described in J. Clin. Invest., 92, 411 (1993). The relationship between LPL activation and cataract is described in Biol. Phar. Bull., 19, 1570 (1996). The relationship between LPL activation and cachexia is described in Anticancer Research, 19, 4099 (1999). The relationship between LPL activation and nephrosis is described in Metabolism, 49, 588 (2000). The relationship between LPL activation and hyperlipidemia is described in Diabetes, 44, 414 (1995). The relationship between LPL activation and obesity is described in Diabetologia, 43, 875 (2000).

DISCLOSURE OF THE INVENTION

The inventors researched compounds having an LPL-activating action to obtain pharmaceuticals (chemotherapeutic agents) effective for preventing and treating hyperlipidemia, obesity, and the like, and subsequently found that specific compounds represented by General Formula (1) below strongly activate LPL. Although such compounds may include some known compounds, it has not been known that they activate LPL. The present invention has been accomplished by further research based on the above findings.

The present invention provides as recited in Items 1 to 42 below:

Item 1. A method for activating LPL in a patient in need of LPL activation treatment, comprising administering an effective amount of a benzene compound into the patient, the benzene compound being represented by General Formula (1):

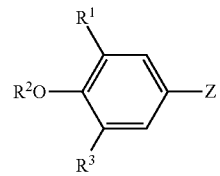

wherein $R^1$ is hydrogen, hydroxy, lower alkyl, lower alkoxy, lower alkoxycarbonyl, carboxy, or phenyl lower alkyl; and $R^2$ is hydrogen; lower alkyl; 1,2,3,4-tetrahydronaphthyl; cycloalkyl lower alkyl; phenyl; phenyl having one or two substituents selected from the group consisting of halogen, lower alkoxy, cyano, halogenated lower alkyl, and halogenated lower alkoxy; phenyl lower alkyl; phenyl lower alkyl having on the benzene ring one or two substituents selected from the group consisting of halogen, lower alkyl, halogenated lower alkyl, cyano, nitro, lower alkoxycarbonyl, carboxy, lower alkoxy, and halogenated lower alkoxy; or lower alkyl having one cycloalkyl and one phenyl or halogenated phenyl; or
$R^1$ and $R^2$ are joined to form —CH=C(Ph)- wherein Ph represents phenyl;
$R^3$ is hydrogen or lower alkoxy; and
Z is a group selected from (a) to (h) below:
(a) imidazo[2,1-b]thiazol-6-yl or imidazo[2,1-b]thiazol-6-yl having one lower alkyl substituent;
(b) benzimidazol-2-yl;
(c) benzothiazol-2-yl;
(d) imidazo[1,2-a]pyrimidin-2-yl;
(e) imidazol-4-yl having one phenyl or halogenated lower alkyl-substituted phenyl;
(f) imidazo[1,2-a]pyridin-3-yl;
(g) imidazo[1,2-a]pyridin-5-yl; and
(h) a group represented by the formula below:

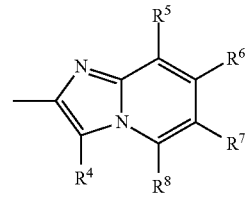

wherein $R^4$ is hydrogen, lower alkyl, or halogen;
$R^5$ is hydrogen, lower alkyl, halogen, hydroxy, lower alkoxy, phenyl lower alkoxy;
$R^6$ is hydrogen, lower alkyl, carboxy, or halogenated lower alkyl;
$R^7$ is hydrogen, lower alkyl, halogen, halogenated lower alkyl, lower alkoxycarbonyl, carboxy, cyano, carbamoyl, or phenyl; and
$R^8$ is hydrogen or lower alkyl, provided, however, that when Z is a group (e), $R^1$ is lower alkoxy, $R^2$ is phenyl lower alkyl, and $R^3$ is hydrogen.

Item 2. A method according to item 1 wherein the benzene compound is a compound of General Formula (1) wherein Z is a group (a).

Item 3. A method according to item 1 wherein the benzene compound is a compound of General Formula (1) wherein Z is a group (b).

Item 4. A method according to item 1 wherein the benzene compound is a compound of General Formula (1) wherein Z is a group (d).

Item 5. A method according to item 1 wherein the benzene compound is a compound of General Formula (1) wherein Z is a group (e).
Item 6. A method according to item 1 wherein the benzene compound is a compound of General Formula (1) wherein Z is a group (f), (g) or (h).
Item 7. A method according to item 1 wherein the benzene compound is a compound shown in any one of (1-1) to (1-4):
(1-1) a compound of formula (1) wherein $R^1$ is lower alkoxy, and $R^2$ is phenyl, phenyl having one or two halogen atoms as substituents on the benzene ring, phenyl lower alkyl group, phenyl lower alkyl group having on the benzene ring one or two substituents selected from the group consisting of halogen, and cyano, or $R^1$ and $R^2$ are jointed to form —CH=C(Ph)- (wherein Ph is phenyl), and Z is a group (h);
(1-2) a compound of formula (1) wherein $R^1$ is lower alkoxy, $R^2$ is phenyl lower alkyl having one or two halogen atoms as substituents on the benzene ring, and Z is a group (a);
(1-3) a compound of formula (1) wherein $R^1$ is lower alkoxy, $R^2$ is phenyl lower alkyl, or phenyl lower alkyl having one or two halogen atoms as substituents on the benzene ring, and Z is a group (f); and
(1-4) a compound of formula (1) wherein $R^1$ is lower alkoxy, $R^2$ is phenyl lower alkyl, and Z is a group (e).
Item 8. A method according to item 1 wherein the patient in need of LPL activation treatment is a hyperlipidemia patient.
Item 9. A method according to item 1 wherein the patient in need of LPL activation treatment is an obese patient.
Item 10. A method according to item 1, wherein the benzene compound is one member selected from the group consisting of 2-(4-benzyloxy-3-methoxyphenyl)imidazo[1,2-a]pyridine, 2-[4-(4-cyanobenzyloxy)-3-methoxyphenyl]imidazo[1,2-a]pyridine, 2-[4-(4-bromo-2-fluorobenzyloxy)-3-methoxyphenyl]imidazo[1,2-a]pyridine, and 2-[4-(4-chlorobenzyloxy)-3-methoxyphenyl]imidazo[1,2-a] pyridine.
Item 11. A method according to item 1, wherein the benzene compound is 6-[4-(4-chlorobenzyloxy)-3-methoxyphenyl] imidazo[2,1-b]thiazole.
Item 12. A method according to item 1, wherein the benzene compound is 4-(4-benzyloxy-3-methoxyphenyl)-2-(4-trifluoromethylphenyl)imidazole.
Item 13. An LPL-activating composition comprising a pharmaceutically acceptable carrier and a benzene compound represented by General Formula (1):

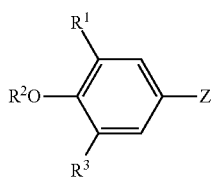

(1)

wherein $R^1$ is hydrogen, hydroxy, lower alkyl, lower alkoxy, lower alkoxycarbonyl, carboxy, or phenyl lower alkyl; and $R^2$ is hydrogen; lower alkyl; 1,2,3,4-tetrahydronaphthyl; cycloalkyl lower alkyl; phenyl; phenyl having one or two substituents selected from the group consisting of halogen, lower alkoxy, cyano, halogenated lower alkyl, and halogenated lower alkoxy; phenyl lower alkyl; phenyl lower alkyl having on the benzene ring one or two substituents selected from the group consisting of halogen, lower alkyl, halogenated lower alkyl, cyano, nitro, lower alkoxycarbonyl, carboxy, lower alkoxy, and halogenated lower alkoxy; or lower alkyl having one cycloalkyl, and one phenyl or halogenated phenyl; or
$R^1$ and $R^2$ are joined to form —CH=C(Ph)- wherein Ph represents phenyl;
$R^3$ is hydrogen or lower alkoxy; and
Z is a group selected from (a) to (h) below:
(a) imidazo[2,1-b]thiazol-6-yl or imidazo[2,1-b]thiazol-6-yl having one lower alkyl substituent;
(b) benzimidazol-2-yl;
(c) benzothiazol-2-yl;
(d) imidazo[1,2-a]pyrimidin-2-yl;
(e) imidazol-4-yl having one phenyl or halogenated lower alkyl-substituted phenyl group;
(f) imidazo[1,2-a]pyridin-3-yl;
(g) imidazo[1,2-a]pyridin-5-yl; and
(h) a group represented by the formula below:

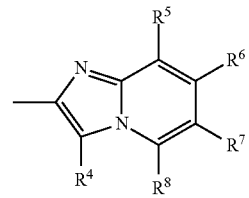

wherein $R^4$ is hydrogen, lower alkyl, or halogen; $R^5$ is hydrogen, lower alkyl, halogen, hydroxy, lower alkoxy, phenyl lower alkoxy;
$R^6$ is hydrogen, lower alkyl, carboxy, or halogenated lower alkyl;
$R^7$ is hydrogen, lower alkyl, halogen, halogenated lower alkyl, lower alkoxycarbonyl, carboxy, cyano, carbamoyl, or phenyl; and
$R^8$ is hydrogen or lower alkyl,
provided, however, that when Z is a group (e), $R^1$ is lower alkoxy, $R^2$ is phenyl lower alkyl, and $R^3$ is hydrogen.
Item 14. An LPL-activating composition according to item 13 wherein the benzene compound is a compound of General Formula (1) wherein Z is a group (a).
Item 15. An LPL-activating composition according to item 13 wherein the benzene compound is a compound of General Formula (1) wherein Z is a group (b).
Item 16. An LPL-activating composition according to item 13 wherein the benzene compound is a compound of General Formula (1) wherein Z is a group (d).
Item 17. An LPL-activating composition according to item 13 wherein the benzene compound is a compound of General Formula (1) wherein Z is a group (e).
Item 18. An LPL-activating composition according to item 13 wherein the benzene compound is a compound of General Formula (1) wherein Z is a group (f), (g) or (h).
Item 19. An LPL-activating composition according to item 13 wherein the benzene compound is a compound shown in any one of (1-1) to (1-4):
(1-1) a compound of formula (1) wherein $R^1$ is lower alkoxy, $R^2$ is phenyl, phenyl having one or two halogen atoms as substituents on the benzene ring, phenyl lower alkyl group, phenyl lower alkyl group having on the benzene ring one or two substituents selected from the group consisting of halogen, and cyano, or $R^1$ and $R^2$ join to form —CH=C(Ph)- (wherein Ph is phenyl), and Z is a group (h);
(1-2) a compound of formula (1) wherein $R^1$ is lower alkoxy, $R^2$ is phenyl lower alkyl having one or two halogen atoms as substituents on the benzene ring, and Z is a group (a);

(1-3) a compound of formula (1) wherein $R^1$ is lower alkoxy, $R^2$ is phenyl lower alkyl, or phenyl lower alkyl having one or two halogen atoms as substituents on the benzene ring, and Z is a group (f); and (1-4) a compound of formula (1) wherein $R^1$ is lower alkoxy, $R^2$ is phenyl lower alkyl, and Z is a group (e).

Item 20. A pharmaceutical composition according to item 13, wherein the benzene compound is one member selected from the group consisting of 2-(4-benzyloxy-3-methoxyphenyl)imidazo[1,2-a]pyridine, 2-[4-(4-cyanobenzyloxy)-3-methoxyphenyl]imidazo[1,2-a]pyridine, 2-[4-(4-bromo-2-fluorobenzyloxy)-3-methoxyphenyl]imidazo[1,2-a]pyridine, and 2-[4-(4-chlorobenzyloxy)-3-methoxyphenyl]imidazo[1,2-a]pyridine.

Item 21. A pharmaceutical composition according to item 13, wherein the benzene compound is 6-[4-(4-chlorobenzyloxy)-3-methoxyphenyl]imidazo[2,1-b]thiazole.

Item 22. A pharmaceutical composition according to item 13, wherein the benzene compound is 4-(4-benzyloxy-3-methoxyphenyl)-2-(4-trifluoromethylphenyl)imidazole.

Item 23. A pharmaceutical composition according to item 13 used for hyperlipidemia prevention or treatment.

Item 24. A pharmaceutical composition according to item 13 used for anti-obesity.

Item 25. A benzene compound represented by General Formula (1a)

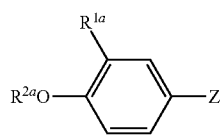

(1a)

wherein (2-1) $R^{1a}$ is lower alkoxy; $R^{2a}$ is phenyl lower alkyl having on the benzene ring one or two substituents selected from the group consisting of halogen, cyano, and nitro; and $Z^a$ is a group (a);

(2-2) $R^{1a}$ is lower alkoxy; $R^{2a}$ is hydrogen, phenyl; phenyl having one or two lower alkoxy groups as substituents; phenyl lower alkyl; or phenyl lower alkyl having on the benzene ring one or two substituents selected from the group consisting of halogen, lower alkyl, halogenated lower alkyl, cyano, nitro, lower alkoxy, and halogenated lower alkoxy; and $Z^a$ is a group (d), (f), or (g);

(2-3) $R^{1a}$ is lower alkoxy, $R^{2a}$ is phenyl lower alkyl, and $Z^a$ is a group (e); or (2-4) $R^{1a}$ is hydroxy or lower alkoxy, and $R^{2a}$ is 1,2,3,4-tetrahydronaphthyl, cycloalkyl lower alkyl, phenyl; phenyl having one or two substituents selected from the group consisting of halogen, lower alkoxy, cyano, halogenated lower alkyl, and halogenated lower alkoxy; phenyl lower alkyl having on the benzene ring one or two substituents selected from the group consisting of halogen, lower alkyl, halogenated lower alkyl, cyano, nitro, lower alkoxycarbonyl, carboxy, lower alkoxy, and halogenated lower alkoxy; or lower alkyl having one cycloalkyl and one phenyl or halogenated phenyl; or $R^{1a}$ and $R^{2a}$ are joined to form —CH=C(Ph)- (wherein Ph is phenyl), and $Z^a$ is a group (h).

Item 26. A benzene compound according to item 25 shown in any one of (3-1) to (3-4):

(3-1) a compound wherein $R^{1a}$ is lower alkoxy, and $R^{2a}$ is phenyl, pheny having one or two halogen atoms as substituents, or phenyl lower alkyl having on the benzene ring one or two substituents selected from the group consisting of halogen and cyano, or $R^1$ and $R^2$ are joined to form —CH=C(Ph)- (wherein Ph is phenyl), and $Z^a$ is a group (h), (3-2) a compound wherein $R^{1a}$ is lower alkoxy, $R^{ea}$ is phenyl lower alkyl having one or two halogen atoms as substituents on the benzene ring, and $Z^a$ is imidazo[2,1-b]thiazol-6-yl, (3-3) a compound wherein $R^{1a}$ is lower alkoxy, $R^{2a}$ is phenyl lower alkyl, or phenyl lower alkyl having one or two halogen atoms as substituents on the benzene ring, and $Z^a$ is a group (f).

(3-4) a compound wherein $R^{1a}$ is lower alkoxy, $R^{2a}$ is phenyl lower alkyl, and $Z^a$ is a group (e).

Item 27. A benzene compound according to item 25, wherein $Z^a$ in General Formula (1a) is a group (d), (f), or (g).

Item 28. A benzene compound according to item 25, wherein $R^{2a}$ in General Formula (1a) is phenyl lower alkyl having on the benzene ring one or two substituents selected from the group consisting of halogen, cyano, and nitro; and $Z^a$ is a group (a).

Item 29. A benzene compound according to item 25, wherein $Z^a$ in General Formula (1a) is a group (e).

Item 30. A benzene compound according to item 25, wherein $Z^a$ in General Formula (1a) is a group (h).

Item 31. A benzene compound according to item 25 selected from the group consisting of 2-[4-(4-cyanobenzyloxy)-3-methoxyphenyl]imidazo[1,2-a]pyridine, 2-[4-(4-bromo-2-fluorobenzyloxy)-3-methoxyphenyl]imidazo[1,2-a]pyridine, 2-[4-(4-chlorobenzyloxy)-3-methoxyphenyl]imidazo[1,2-a]pyridine, 6-[4-(4-chlorobenzyloxy)-3-methoxyphenyl]imidazo[2,1-b]thiazole, and 4-(4-benzyloxy-3-methoxyphenyl)-2-(4-trifluoromethylphenyl)imidazole.

Item 32. Use of the benzene compound of item 13 for preparing an LPL activating composition.

Item 33. Use of the benzene compound of item 13 for preparing a hyperlipidemia preventive or therapeutic composition.

Item 34. Use of the benzene compound of item 13 for preparing an anti-obesity composition.

Item 35. A pharmaceutical composition comprising the benzene compound of item 25, and a pharmaceutically acceptable carrier.

Item 36. A pharmaceutical composition according to item 25 used as an LPL activating composition.

Item 37. A pharmaceutical composition according to item 25 used as a hyperlipidemia preventive or therapeutic composition.

Item 38. A pharmaceutical composition according to item 25 used as an anti-obesity composition.

Item 39. A method for preventing hyperlipidemia in a patient in need of hyperlipidemia prevention, comprising administering an effective amount of at least one benzene compound of item 25 into the patient.

Item 40. A method for treating obesity in a patient in need of obesity treatment, comprising administering an effective amount of at least one benzene compound of item 25 into the patient.

Item 41. Use of the benzene compound of item 13 for preventing or treating hyperlipidemia.

Item 42. Use of the benzene compound of item 13 for preventing or treating obesity.

Benzene Compounds of the Present Invention

Hereinbelow, the benzene compounds represented by General Formula (1) (hereinafter simply referred to as "Compounds 1" of the present invention) used in the LPL-activating compositions of the invention are described in more detail.

Substituents used in General Formula (1) representing Compounds 1 and used elsewhere in this specification are as described below. The term "lower" used with radicals containing carbon atoms herein refers to 1 to 6 carbon atoms.

Examples of lower alkyl groups include $C_{1-6}$ linear or branched alkyl groups such as methyl, ethyl, propyl, isopropyl, butyl, isobutyl, tert-butyl, pentyl, hexyl, etc.

Examples of lower alkoxy groups include $C_{1-6}$ linear or branched alkoxy groups such as methoxy, ethoxy, propoxy, isopropoxy, butoxy, pentyloxy, hexyloxy, etc.

Examples of lower alkoxy carbonyl groups include $C_{1-6}$ linear or branched alkoxycarbonyl groups such as methoxycarbonyl, ethoxycarbonyl, propoxycarbonyl, 1-methylethoxycarbonyl, butoxycarbonyl, 2-methylpropoxycarbonyl, 1,1-dimethylethoxycarbonyl, pentyloxycarbonyl, hexyloxycarbonyl, etc.

Examples of phenyl lower alkoxy groups include $C_{1-6}$ linear or branched alkoxy groups having one phenyl substituent, such as 1-phenylethoxy, 2-phenylethoxy, 3-phenylpropoxy, 2-phenylpropoxy, 4-phenylbutyloxy, 5-phenylpentyloxy, 6-phenylhexyloxy, etc.

Examples of 1,2,3,4-tetrahydronaphthyl groups include 1,2,3,4-tetrahydronaphthalen-1-yl and 1,2,3,4-tetrahydronaphthalen-2-yl.

Examples of cycloalkyl lower alkyl groups include $C_{1-6}$ alkyl groups having one $C_{3-8}$ cycloalkyl substituent, such as cyclopropylmethyl, 2-cyclopropylethyl, 3-cyclopropylpropyl, 4-cyclopropylbutyl, 5-cyclopropylpentyl, 6-cyclopropylhexyl, cyclobutylmethyl, cyclopentylmethyl, cyclohexylmethyl, cycloheptylmethyl, cyclooctylmethyl, etc.

Examples of cycloalkyl groups include $C_{3-8}$ cycloalkyl groups such as cyclopropyl, cyclobutyl, cyclopentyl, cyclohexyl, cycloheptyl, cyclooctyl, etc.

Examples of phenyl groups having one or two substituents selected from the group consisting of halogen, lower alkoxy, cyano, halogenated lower alkyl, and halogenated lower alkoxy include 2-chlorophenyl, 3-chlorophenyl, 4-chlorophenyl, 4-fluorophenyl, 4-bromophenyl, 4-iodophenyl, 3,4-dichlorophenyl, 2,4-dichlorophenyl, 2,6-dichlorophenyl, 2-cyanophenyl, 3-cyanophenyl, 4-cyanophenyl, 2-trifluoromethoxyphenyl, 3-trifluoromethoxyphenyl, 4-trifluoromethoxyphenyl, 4-tetrafluoroethoxyphenyl, 2-methoxyphenyl, 3-methoxyphenyl, 4-methoxyphenyl, 2,4-dimethoxyphenyl, 3,4-dimethoxyphenyl, 3,5-dimethoxyphenyl, 4-ethoxyphenyl, 4-propoxyphenyl, 4-butoxyphenyl, 4-(1,1-dimethylethoxy)phenyl, 4-pentyloxyphenyl, 4-hexyloxyphenyl, 2-trifluoromethylphenyl, 3-trifluoromethylphenyl, 4-trifluoromethylphenyl, 2,4-bis(trifluoromethyl)phenyl, 3,4-bis(trifluoromethyl)phenyl, 3,5-bis(trifluoromethyl)phenyl, 4-tetrafluoroethylphenyl, 4-heptafluoropropyl phenyl, 4-nonafluorobutylphenyl, 4-undecafluoropentylphenyl, 4-tridecafluorohexylphenyl, etc.

Examples of halogen atoms include fluorine, chlorine, bromine, iodine, etc.

Examples of lower alkoxy groups include $C_{1-6}$ linear or branched alkoxy groups, such as methoxy, ethoxy, propoxy, 1-methylethoxy, butoxy, 2-methylpropoxy, pentyloxy, hexyloxy, and the like.

Examples of halogenated lower alkyl groups include $C_{1-6}$ perhalogeno-alkyl groups, especially $C_{1-6}$ perfluoro-alkyl groups. The halogen substituents are of the same type, selected from the group consisting of fluorine, chlorine, bromine, and iodine. Specific examples are trifluoromethyl, pentafluoroethyl, heptafluoropropyl, nonafluorobutyl, undecafluoropentyl, tridecafluorohexyl, etc.

Examples of halogenated lower alkoxy groups include $C_{1-6}$ perhalogeno-alkoxy groups, especially $C_{1-6}$ perfluoro-alkoxy groups. The halogen substituents are of the same type, selected from the group consisting of fluorine, chlorine, bromine, and iodine. Specific examples are trifluoromethoxy, pentafluoroethoxy, heptafluoropropoxy, nonafluorobutyloxy, undecafluoropentyloxy, tridecafluorohexyloxy, etc.

Examples of phenyl lower alkyl groups include $C_{1-6}$ alkyl groups having as a substituent one phenyl group, such as benzyl, 1-phenylethyl, 2-phenylethyl, 3-phenylpropyl, 2-phenylpropyl, 4-phenylbutyl, 5-phenylpentyl, 6-phenylhexyl, etc.

Examples of phenyl lower alkyl groups having on the benzene ring one or two substituents selected from the group consisting of halogen, lower alkyl, halogenated alkyl, cyano, nitro, lower alkoxycarbonyl, carboxy, lower alkoxy, and halogenated lower alkoxy include:

(1) Phenyl lower alkyl groups having one halogen atom as a substituent:
2-fluorobenzyl, 3-fluorobenzyl, 4-fluorobenzyl, 2,4-difluorobenzyl, 2,5-difluorobenzyl, 2,6-difluorobenzyl, 3,5-difluorobenzyl, 2-chlorobenzyl, 3-chlorobenzyl, 4-chlorobenzyl, 2,4-dichlorobenzyl, 3,4-dichlorobenzyl, 4-bromobenzyl, 4-iodobenzyl, 4-bromo-2-fluorobenzyl, 4-chloro-2-fluorobenzyl, 1-(4-chlorophenyl)ethyl, 2-(4-chlorophenyl)ethyl, 3-(4-chlorophenyl)propyl, 2-(4-chlorophenyl)propyl, 4-(4-chlorophenyl)butyl, 5-(4-chlorophenyl)pentyl, 6-(4-chlorophenyl)hexyl, and the like;

(2) Lower alkyl-substituted phenyl lower alkyl groups:
2-methylbenzyl, 3-methylbenzyl, 4-methylbenzyl, 4-ethylbenzyl, 4-(1,1-dimethylethyl)benzyl, 4-propylbenzyl, 4-butylbenzyl, 4-pentylbenzyl, 4-hexylbenzyl, 1-(4-methylphenyl)ethyl, 2-(4-methylphenyl)ethyl, 3-(4-methylphenyl)propyl, 4-(4-methylphenyl)butyl, 5-(4-methylphenyl)pentyl, 6-(4-methylphenyl)hexyl, and the like;

(3) Phenyl lower alkyl groups having one halogenated lower alkyl group (especially one $C_{1-6}$ perhalogeno-alkyl group) as a substituent:
2-trifluoromethylbenzyl, 3-trifluoromethylbenzyl, 4-trifluoromethylbenzyl, 4-pentafluoroethylbenzyl, 4-(2,2,2-trifluoroethyl)benzyl, 4-heptafluoropropylbenzyl, 4-nonafluorobutylbenzyl, 4-undecafluoropentylbenzyl, 4-tridecafluorohexylbenzyl, 1-(4-trifluoromethylphenyl)ethyl, 2-(4-trifluoromethylphenyl)ethyl, 3-(4-trifluoromethylphenyl)propyl, 4-(4-trifluoromethylphenyl)butyl, 5-(4-trifluoromethylphenyl)pentyl, 6-(4-trifluoromethylphenyl)hexyl, and the like;

(4) Cyano-substituted phenyl lower alkyl groups:
cyanophenyl-$C_{1-6}$ alkyl groups such as 2-cyanobenzyl, 3-cyanobenzyl, 4-cyanobenzyl, 1-(4-cyanophenyl)ethyl, 2-(4-cyanophenyl)ethyl, 3-(4-cyanophenyl)propyl, 4-(4-cyanophenyl)butyl, 5-(4-cyanophenyl)pentyl, 6-(4-cyanophenyl)hexyl, and the like;

(5) Nitro-substituted phenyl lower alkyl groups:
nitrophenyl-$C_{1-6}$ alkyl groups such as 2-nitrobenzyl, 3-nitrobenzyl, 4-nitrobenzyl, 1-(4-nitrophenyl)ethyl, 2-(4-nitrophenyl)ethyl, 3-(4-nitrophenyl)propyl, 4-(4-nitrophenyl)butyl, 5-(4-nitrophenyl)pentyl, 6-(4-nitrophenyl)hexyl, and the like;

(6) Lower alkoxycarbonyl-substituted phenyl lower alkyl groups:
$C_{1-6}$ alkoxycarbonylphenyl-$C_{1-6}$ alkyl groups such as 2-methoxycarbonylbenzyl, 3-methoxycarbonylbenzyl, 4-methoxycarbonylbenzyl, 4-ethoxycarbonylbenzyl, 4-propoxycarbonylbenzyl, 4-butoxycarbonylbenzyl, 4-pentyloxycarbonylbenzyl, 4-hexyloxycarbonylbenzyl, 1-(4-methoxycarbonylphenyl)ethyl, 2-(4-methoxycarbonylphenyl)ethyl, 3-(4-methoxycarbonylphenyl)propyl, 4-(4-methoxycarbonylphenyl)butyl, 5-(4-methoxycarbonylphenyl)pentyl, 6-(4-methoxycarbonylphenyl)hexyl, and the like;
(7) Carboxyl-substituted phenyl lower alkyl groups:
carboxyphenyl-$C_{1-6}$ alkyl groups such as 2-carboxylbenzyl, 3-carboxylbenzyl, 4-carboxylbenzyl, 1-(4-carboxylphenyl)ethyl, 2-(4-carboxylphenyl)ethyl, 3-(4-carboxylphenyl)propyl, 4-(4-carboxylphenyl)butyl, 5-(4-carboxylphenyl)pentyl, 6-(4-carboxylphenyl)hexyl, and the like;
(8) Lower alkoxy-substituted phenyl lower alkyl groups:
2-methoxybenzyl, 3-methoxybenzyl, 4-methoxybenzyl, 4-ethoxybenzyl, 4-propoxybenzyl, 4-butoxybenzyl, 4-pentyloxybenzyl, 4-hexyloxybenzyl, 1-(4-methoxyphenyl)ethyl, 2-(4-methoxyphenyl)ethyl, 3-(4-methoxyphenyl)propyl, 4-(4-methoxyphenyl)butyl, 5-(4-methoxyphenyl)pentyl, 6-(4-methoxyphenyl)hexyl, 3,5-dimethoxybenzyl, 3,4,5-trimethoxybenzyl, and the like;
(9) Halogenated lower alkoxy-substituted phenyl lower alkoxy groups:
2-trifluoromethoxybenzyl, 3-trifluoromethoxybenzyl, 4-trifluoromethoxybenzyl, 4-pentafluoroethoxybenzyl, 4-(2,2,2-trifluoroethoxy)benzyl, 4-heptafluoropropoxybenzyl, 4-nonafluorobutoxybenzyl, 4-undecafluoropentyloxybenzyl, 4-tridecafluorohexyloxybenzyl, 1-(4-trifluoromethoxyphenyl)ethyl, 2-(4-trifluoromethoxyphenyl)ethyl, 3-(4-trifluoromethoxyphenyl)propyl, 4-(4-trifluoromethoxyphenyl)butyl, 5-(4-trifluoromethoxyphenyl)pentyl, 6-(4-trifluoromethoxyphenyl)hexyl, and the like; and
(10) Other substituted phenyl lower alkyl groups:
5-fluoro-2-trifluoromethylbenzyl, 2-fluoro-5-trifluoromethylbenzyl, 5-fluoro-2-methylbenzyl, 5-fluoro-2-methoxybenzyl, 4-methoxy-3-methoxycarbonylbenzyl, 3-methoxy-4-methoxycarbonylbenzyl, etc.

Examples of halogenated lower phenyl groups include 4-fluorophenyl, 4-chlorophenyl, 4-bromophenyl, 4-iodophenyl, 3-chlorophenyl, 2-chlorophenyl, etc.

Examples of lower alkyl groups having one cycloalkyl and one phenyl or halogenated phenyl include α-cyclopropylbenzyl, α-cyclopropyl-4-chlorobenzyl, α-cyclopropyl-4-fluorobenzyl, α-cyclopropyl-4-bromobenzyl, α-cyclopropyl-4-iodobenzyl, α-cyclopropyl-3-chlorobenzyl, α-cyclopropyl-2-chlorobenzyl, α-cyclobutylbenzyl, α-cyclopentylbenzyl, α-cyclohexylbenzyl, α-cycloheptylbenzyl, α-cyclooctylbenzyl, etc.

Examples categorized as (a), i.e., imidazo[2,1-b]thiazol-6-yl or imidazo[2,1-b]thiazol-6-yl having one lower alkyl substituent include imidazo[2,1-b]thiazol-6-yl, 2-methylimidazo[2,1-b]thiazol-6-yl, 3-methylimidazo[2,1-b]thiazol-6-yl, 5-methylimidazo[2,1-b]thiazol-6-yl, 2-ethylimidazo[2,1-b]thiazol-6-yl, 2-propylimidazo[2,1-b]thiazol-6-yl, 2-butylimidazo[2,1-b]thiazol-6-yl, 2-pentylimidazo[2,1-b]thiazol-6-yl, 2-hexyl[2,1-b]thiazol-6-yl, etc.

Examples categorized as (e), i.e., imidazole-4-yl having one phenyl substituent or one halogenated lower alkyl-substituted lower alkyl phenyl substituent include 2-phenylimidazol-4-yl, 5-phenylimidazol-4-yl, 2-(4-trifluoromethylphenyl)imidazol-4-yl, 5-(4-trifluoromethylphenyl)imidazol-4-yl, 2-(3-trifluorophenyl)imidazol-4-yl, 2-(2-trifluoromethylphenyl)imidazol-4-yl, 2-(4-pentafluoroethylphenyl)imidazol-4-yl, 2-(4-heptafluoropropylphenyl)imidazol-4-yl, 2-(4-nonafluorobutylphenyl)imidazol-4-yl, 2-(4-undecafluorohexylphenyl)imidazol-4-yl, etc.

Among the compounds of the present invention, compounds preferable in terms of pharmacological activity are those described in (I) to (V) below:

(I) Compounds represented by General Formula (1) wherein Z is (a);
(II) Compounds represented by General Formula (1) wherein Z is (b) or (c);
(III) Compounds represented by General Formula (1) wherein Z is (d);
(IV) Compounds represented by General Formula (1) wherein Z is (e); and
(V) Compounds represented by General Formula (1) wherein Z is (f), (g) or (h).

Among the compounds described above, those belonging to (I), (IV) and (V) are preferable. Especially preferable are those that have (a), (e) or (h) as Z.

Compounds (1) (active compounds for the LPL-activating compositions of the invention) and the novel benzene compounds (hereinafter referred to as "Compounds (1a)" of the present invention and will be described later) herein include their sodium salts, potassium salts, and like alkaline metal salts; calcium salts, magnesium salts, and like alkaline-earth metal salts; and copper salts and other salts. These salts can be prepared according to known methods. These salts thus obtained have pharmacological activity identical to that of the compounds in the free form, and are also of use in LPL-activating compositions and the like.

Moreover, Compounds (1) and Compounds (1a) include their pharmaceutically acceptable acid addition salts, for example, hydrochlorides, nitrates, sulfates, hydrobromides, phosphates, carbonates, acetates, lactates, citrates, and the like. Such acid addition salts can be prepared according to known methods. These acid addition salts have pharmacological activity identical to that of the compounds in the free form. Therefore, the present invention further provides acid addition salts and pharmaceutical compositions such as LPL-activating compositions and the like containing such acid addition salts as active ingredients.

Furthermore, Compounds (1) and Compounds (1a) may include optical isomers having a carbon atom as an asymmetric center. The present invention further provides racemates that are mixtures of such optical isomers, optically active forms of such optical isomers, and LPL-activating compositions containing as active ingredients either such racemates or optical isomers. The aforementioned optical isomers can be separated according to known separation methods.

Preparation Methods for Compounds (1)

Compounds (1) of the invention, depending on the type of Substituent Z, specifically, according to which group described in (a) to (h) above is contained therein, may be known compounds or may be prepared according to known methods.

For example, compounds wherein Z is imidazo[2,1-b]thiazole-6-yl or imidazo[2,1-b]thiazole-6-yl having one lower alkyl substituent and categorized as (a) can be either compounds described in Japanese Unexamined Patent Application Publication No. 291976/1995, or have a skeletal structure similar to that of the compounds described in the publication. These compounds can be prepared according to Method 1 or 3 described in the above publication, or can be prepared with reference to its methods. More specifically, these compounds can be prepared by subjecting, as starting materials, Compounds (2) described in Method 1 of the above publication or corresponding compounds having a suitable substituent and Compounds (3) or corresponding compounds having a suitable substituent to cyclization reaction. Alternatively, they can be prepared by hydrolyzing Compounds (1c) described in Method 3 of the publication or corresponding compounds having a suitable substituent, and adding suitable halides to the compounds thus obtained. Conditions for these reactions can be selected according to the publication.

Compounds wherein Z is benzimidazol-2-yl and categorized as (b) can be prepared according to a method described in European Patent Application Publication No. 694535 or can be prepared in reference to this method. More specifically, these compounds can be prepared according to page 6, lines 24 to 58, of the publication by subjecting, as starting materials, o-phenylenediamines having a suitable substituent to cyclization reaction.

Compounds wherein Z is benzothiazol-2-yl and categorized as (c) can be prepared according to methods described in U.S. Pat. No. 3,876,791 or can be prepared with reference to these methods. More specifically, these compounds can be prepared in accordance with methods described in column 2, lines 40 to 56, and column 3, lines 39 to 50, of its specification. The details of these methods are described in U.S. Pat. Nos. 3,669,979; 3,647,812; 3,095,422; and *J. Medicinal Chem.* 14 (1971): 248. More specifically, the desired compounds wherein Z is benzothiazol-2-yl and categorized as (c) can be prepared, for example, by reacting suitable o-aminothiophenols and aromatic acids in the presence of a phosphorous trichloride, conducting this reaction in the presence of a boric acid catalyst, or subjecting suitable o-aminothiophenols and aromatic aldehydes to condensation reaction.

Compounds wherein Z is imidazo[1,2-a]pyrimidin-2-yl and categorized as (d) can be the compounds represented by General Formula Ia in European Patent Application Publication No. 113236 or be compounds similar to them. These compounds can be prepared according to a method described in the above publication or prepared in reference to the method. More specifically, these compounds can be prepared according to page 7, line 15 to page 8, line 28, or Example 1 of the above publication using suitable starting materials corresponding to amines of General Formula II and α-haloketones of General Formula III of the publication.

Compounds wherein Z is imidazol-4-yl or imidazol-4-yl having a phenyl substituent and categorized as (e) can be prepared according to methods described in Japanese Unexamined Patent Application Publication No. 163861/2001, or can be prepared with reference to these methods. More specifically, these compounds can be prepared according to Preparation Methods 1 and 2, Example 8, etc., by reacting compounds corresponding to the α-diketones of General Formula (II) and compounds corresponding to the benzaldehyde compounds of General Formula (III). Alternatively, compounds wherein Z is categorized as (e) can be prepared by reacting suitable compounds corresponding to 2-acetophenones wherein a halogen atom is substituted at the 2 position of General Formula (IV) and those corresponding to the benzamidine compounds represented by General Formula (V) of the publication.

α-Diketones of General Formula (II) can be prepared according to known methods. Examples of such methods are, for example, (1) reacting suitable amino acids with suitable alkyl, aryl, or allyl metal reagents (see *Tetrahedron. Lett.* 24 (23) (1983): 2375); (2) reacting suitable halogenated aryls with aryl acetylenes (see *Tetrahedron. Lett.* (1971): 2941; (3) reacting suitable α-aryl ketones (*J. Org. Chem.* 53 (1988): 129; *J. Org. Chem.* 24 (1995): 516; *Tetrahedron Lett.* (1972): 1175; *Org. Syn.* 32 (1952): 35; *J. Org. Chem.* 14 (1949): 836; *Am. Chem. Soc.* 71 (1949): 3760; *J. Am. Chem. Soc.* 71 (1949): 1585; etc.), and like methods.

Compounds wherein Z is a specific heterocyclic group categorized as (h) can be the compounds described in, for example, Japanese Unexamined Patent Application Publication No. 291972/1995. These compounds can be prepared according to methods described in the above publication, or can be prepared with reference to these methods. More specifically, these compounds can be prepared according to Methods 1 to 3, Examples 1 to 20, etc. In particular, compounds wherein Z is a specific heterocyclic group categorized as (h) can be prepared by (Method 1) subjecting suitable compounds corresponding to Compounds (2) and those corresponding to Compounds (3) of the publication to cyclization reaction; (Method 2) hydrolyzing compounds corresponding to Compounds (1b); or (Method 3) reacting cycloalkylhalides (4) with compounds corresponding to Compounds (1c).

The above literatures are incorporated herein by reference.

Compounds wherein Z is imidazo[1,2-a]pyridine-3-yl and categorized as (f) and compounds wherein Z is imidazo[1,2-a]pyridine-5-yl and categorized as (g) (compounds represented by General Formula (4)) can be prepared, for example, according to the process shown in Reaction Scheme 1 below:

(Reaction Scheme 1)

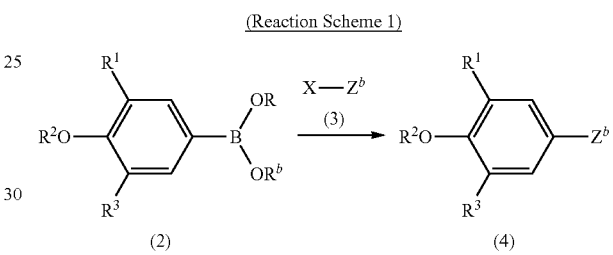

wherein $R^1$, $R^2$ and $R^3$ are as defined above; X represents halogen; B represents boron; R and Rb may be the same or different and independently represent hydrogen or lower alkyl, or R and Rb are joined to form lower alkylene that may have a lower alkyl substituent; and $Z^b$ is a group (f) or (g).

Compound (4) shown in Reaction Scheme 1 is obtained by reacting Compound (2) with a slight excess of Compound (3). This reaction can be conducted in a suitable inert solvent such as N,N-dimethylformamide (DMF), N,N-dimethylacetamide (DMA), or the like, in the presence of an aqueous solution containing an excess, relative to Compound (2), of potassium phosphate, and in the presence of a catalytic amount of tetrakis(triphenylphosphinato)palladium. The reaction temperature is selected from 50° C. to the reflux temperature of the solvent. The reaction completes in about 5 to about 50 hours.

Compound (2) can be prepared according to the method described in *J. Org. Chem.*, 60. 7508 (1995). Compound (3) can be prepared according to the method described in *J. Org. Chem.*, 30 (12), 4085 (1965), and Japanese Unexamined Patent Publication No. 324688/1998.

Compounds of the invention wherein Z is not $Z^b$ (i.e., compounds of the invention other than compound (4) in Reaction Scheme-1) can be prepared in the same manner as the above-mentioned method of preparing the compounds wherein Z is a group shown in one of (a) to (e) and (h).

Compounds 1 of the present invention wherein $R^2$ is hydrogen (for example, compounds represented by General Formula (4) in Reaction Scheme 1 when R is hydrogen) can be converted to compounds having the desired $R^2$ according to Reaction Scheme 2 below:

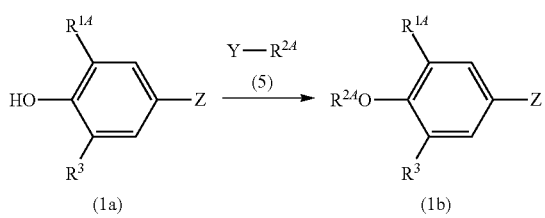

wherein $R^{1A}$ is hydrogen, hydroxy, lower alkyl, lower alkoxy, lower alkoxycarbonyl, carboxyl, or phenyl lower alkoxy. $R^{2A}$ is lower alkyl; 1,2,3,4-tetrahydronaphthyl; cycloalkyl lower alkyl; phenyl; phenyl having 1 or 2 substituents selected from the group consisting of halogen, lower alkoxy, cyano, halogenated lower alkyl, and halogenated lower alkoxy; phenyl lower alkyl; phenyl lower alkyl having on the benzene ring one or two substituents selected from the group consisting of halogen, lower alkyl, halogenated lower alkyl, cyano, nitro, lower alkoxycarbonyl, carboxyl, phenyl lower alkyl having one or two substituents selected from the group consisting of lower alkoxy and halogenated lower alkoxy, or lower alkyl having one cycloalkyl and one phenyl or halogenated phenyl. Y is halogen or —B(OH)$_2$. $R^3$ and Z are as defined above.

The conversion reaction shown in Reaction Scheme 2 can be carried out as described below, according to the type of Substituent Y of Compound (5).

In particular, when Y is halogen, Compounds (1a) and (5) are reacted in a suitable inert solvent such as DMF, DMA or the like in the presence of potassium carbonate, cesium carbonate, or like alkali. Compound (5) and alkali are both usually used equimolar to or in excess of Compound (1a). The reaction is generally conducted at 0° C. to room temperature over about 5 to about 100 hours.

When Y is —B(OH)$_2$, Compounds (1a) and (5) are reacted in a suitable inert solvent such as DMF, DMA, dichloromethane, or the like, in the presence of triethylamine, N,N-dimethylaniline or like base, by further adding copper (II) acetate as necessary. Compound (5), a base, and copper (II) acetate can each be used in equimolar to or in excess molar relative to Compound (1a). The reaction is generally conducted at 0° C. to room temperature over about 5 to about 100 hours.

As described above, the benzene compounds represented by General Formula (1a) are novel compounds.

The compound of General Formula (1a) wherein Z is a group (f) or (g) can be produced by a method according to the above Reaction Scheme-1.

The compound of General Formula (1a) wherein Z is a group (a) can be produced by the method described in Example 23 or a method similar thereto.

The compound of General Formula (1a) wherein Z is a group (d) can be produced by the method described in Example 28 or a method similar thereto.

The compound of General Formula (1a) wherein Z is a group (e) can be produced by the method described in Example 95 or a method similar thereto.

The compound of General Formula (1a) wherein Z is a group (h) can be produced by the method described in Example 1 or a method similar thereto.

The desired compounds (Compounds 1) shown in the aforementioned Reaction Formulae and salts thereof can be readily separated and purified according to conventional separation methods. Examples of such methods include adsorption chromatography, preparative thin layer chromatography, recrystallization, solvent extraction, etc.

Pharmaceutical Compositions of the Present Invention

Compounds 1 (including their salts, same applies hereinbelow) activate lipoprotein lipase (LPL) and are of use for preventing or treating hyperlipidemia, arteriosclerosis, obesity, etc. Therefore, the present invention further provides hyperlipidemia preventive and therapeutic agents, hyperlipidemia preventive and therapeutic compositions, anti-obesity agents, and anti-obesity compositions.

The LPL-activating compositions (including hyperlipidemia preventive and therapeutic agents, anti-obesity agents, etc.) of the present invention are prepared as pharmaceutical compositions (in the form of pharmaceutical preparations) containing Compound 1 and pharmaceutically acceptable carriers. Examples of pharmaceutically acceptable carriers for use in the pharmaceutical compositions of the invention include fillers, extenders, binders, humectants, disintegrants, surfactants, lubricants, and like diluents and excipients that are usually used depending on the application of the pharmaceutical preparations. These carriers are suitably selected according to the unit dosage for of the pharmaceutical preparations to be created.

A variety of unit dosage forms can be suitably selected for the pharmaceutical compositions according to their therapeutic purposes. Typical examples are tablets, pills, powders, solutions, suspensions, emulsions, granules, capsules, suppositories, injections (solutions, suspensions, etc.), ointments, etc.

In producing tablets, pharmaceutically acceptable carriers include lactose, saccharose, sodium chloride, glucose, urea, starch, calcium carbonate, kaolin, crystalline cellulose, silicic acid, potassium phosphate, and like excipients; water, ethanol, propanol, simple syrup, glucose solution, starch solution, gelatin solution, carboxylmethylcellulose, hydroxypropylcellulose, methylcellulose, polyvinylpyrrolidone, and like binders; sodium carboxymethylcellulose, calcium carboxymethylcellulose, low-substituted hydroxypropylcellulose, dried starch, sodium alginate, powdered agar, powdered laminaran, sodium hydrogencarbonate, calcium carbonate, and like disintegrants; polyoxyethylene sorbitan fatty acid esters, sodium lauryl sulfate, stearic acid monoglyceride, and like surfactants; saccharose, stearin, cacao butter, hydrogenated oils, and like disintegration inhibitors; quaternary ammonium bases, sodium lauryl sulfate, and like absorption enhancers; glycerin, starch, and like humectants; starch, lactose, kaolin, bentonite, colloidal silica, and like absorbents; purified talc, stearate, boric acid powder, polyethylene glycol, and like lubricants; etc. Furthermore, tablets can be formulated with conventional coatings if necessary, for example, sugar-coated, gelatin-coated, enteric, or film-coated, double- or multi-layer tablets, etc.

In producing pills, pharmaceutically acceptable carriers include, for example, glucose, lactose, starch, cacao butter, hydrogenated vegetable oil, kaolin, talc, and like excipients; powdered gum arabic, powdered tragacanth, gelatin, ethanol, and like binders; laminaran, agar, and like disintegrants; etc.

In producing suppositories, pharmaceutically acceptable carriers include, for example, polyethylene glycol, cacao butter, higher alcohols and their esters, gelatin, semisynthetic glycerides, etc.

Capsules can be prepared in a conventional manner usually by encapsulating Compound 1 in combination with the aforementioned pharmaceutically acceptable carriers into hard gelatin capsules, soft gelatin capsules, and the like.

When the pharmaceutical compositions of the invention are formulated into injectable forms such as solutions, emulsions, suspensions, and the like, they are preferably sterilized and isotonic with blood. In formulating into injections, examples of diluents usable are water, ethanol, macrogol, propylene glycol, ethoxylated isostearyl alcohol, polyoxylated isostearyl alcohol, polyoxyethylene sorbitan fatty acid esters, etc. In this case, common salt, glucose, or glycerin can be used in the pharmaceutical preparations in an amount sufficient to produce isotonic solutions. Furthermore, conventional auxiliary cosolvents, buffers, soothing agents can be added.

When the pharmaceutical compositions of the invention are formulated into ointments, such as paste, cream, gel, and the like, examples of diluents usable are white petrolatum, paraffin, glycerin, cellulose compounds, polyethylene glycol, silicone, bentonite, etc.

Moreover, as necessary, colorants, preservatives, aroma chemicals, flavorings, sweeteners, etc., and other pharmaceuticals can be used in the pharmaceutical compositions of the invention.

The amount of active compound contained in the pharmaceutical composition of the invention is not limited and can be suitably selected from a wide range. It is generally preferable that the active compound accounts for about 0.5 to about 90 wt. %, preferably about 1 to about 85 wt. %, of the pharmaceutical composition.

Administrative routes for the pharmaceutical preparations of the invention are not limited, and can be selected according to the form of each preparation, age of the patient, gender, degree of the disease, and other conditions. For example, tablets, pills, solutions, suspensions, emulsions, granules, and capsules are administered orally. Injections are intravenously, intramuscularly, intracutaneously, subcutaneously, or intraperitoneally administered alone or in combination with glucose, amino acid, or like conventional replenisher fluids. Suppositories are administered intrarectally.

Dosage of the pharmaceutical preparation of the invention can be suitably selected according to the application, age of the patient, gender, degree of the disease, and other conditions. Usually, the pharmaceutical preparation is administered such that the active ingredient, i.e., Compound (1), can be given to an adult in a dose of about 0.5 to about 20 mg, and preferably about 1 to about 10 mg, per kg body weight. The pharmaceutical preparation can be given in a single dose or divided (2 to 4) doses per day.

Preventive and Therapeutic Methods of the Present Invention

The present invention provides a method for activating LPL in a patient in need of LPL activation including administering to the patient at least one member of Compounds 1 in an amount effective for LPL activation.

Moreover, the invention is directed to a method for preventing hyperlipidemia for a patient requiring hyperlipidemia prevention including administering to the patient at least one member of Compounds 1 in an amount effective for hyperlipidemia prevention.

The invention further relates to a method for treating hyperlipidemia for a patient requiring hyperlipidemia treatment including administering to the patient at least one member of Compounds 1 in an amount effective for hyperlipidemia treatment.

Furthermore, the invention provides a method for preventing obesity for a patient requiring obesity prevention including administering to the patient at least one member of Compounds 1 in an amount effective for obesity prevention.

The invention also pertains to a method for treating obesity for a patient requiring obesity treatment including administering to the patient at least one member of Compounds 1 in an amount effective for obesity treatment.

Furthermore, the present invention provides a use of Compounds 1 for preparing LPL-activating compositions, use of Compounds 1 for preparing hyperlipidemia preventive compositions, use of Compounds 1 for preparing hyperlipidemia therapeutic compositions, and use of Compounds 1 for preparing anti-obesity compositions.

BEST MODE FOR CARRYING OUT THE INVENTION

Examples are given below to illustrate the invention in more detail, but the scope of the invention is not limited to these examples.

In the examples, unless otherwise specified, $^1$H-NMR spectroscopy was conducted in dimethylsulfoxide-$D_6$ (DMSO-$d_6$) solvent using tetramethylsilane (TMS) as an internal standard.

Example 1

Preparation of 2-(4-benzyloxy-3-methoxyphenyl)imidazo[1,2-a]pyridine (Step 1)

At a temperature of 0° C., 28.5 g (75.8 mmol) of phenyltrimethylammonium tribromide was added over 75 minutes to 120 ml of an anhydrous tetrahydrofuran solution of 12.0 g (72.2 mmol) of 4'-hydroxy-3'-methoxyacetophenone. This mixture was stirred for 2 hours at 0° C. and 30 minutes at room temperature. The reaction suspension thus obtained was concentrated under reduced pressure, mixed with 100 ml of ethyl acetate/hexane (1:1 v/v), and stirred for 30 minutes at 0° C. The crystalline phenyltrimethylammonium tribromide present in the suspension was removed by suction filtration and rinsed with 50 ml of ethyl acetate/hexane (1:1 v/v). The filtered solution was concentrated under reduced pressure, thereby giving 30 g of crude product.

At room temperature, 14.95 g (158.9 mmol) of 2-aminopyridine was added to 150 ml of an acetonitrile solution of the crude product (30 g) obtained above. The mixture was stirred for 45 minutes at 50° C. and 30 minutes at 80° C. The reaction mixture was left to stand at room temperature overnight, and the precipitated crystals were collected by suction filtration and rinsed with about 50 ml of acetonitrile. The crystals thus obtained were dried at 80° C. under reduced pressure, thereby yielding 19.0 g 2-(4-hydroxy-3-methoxyphenyl)imidazo[1,2-a]pyridine hydrobromide. This compound hereinafter is referred to as "Example Compound 145".

(Step 2)

At a temperature of 0° C., 15.4 g (111.4 mmol) of potassium carbonate was added to a 106 ml anhydrous DMF suspension of 17.0 g (52.9 mmol) of the compound obtained in Step 1 (Example Compound 145). The mixture was stirred for 60 minutes while adding dropwise 10.4 g (60.8 mmol) of benzyl bromide, and further stirred for 60 minutes at 0° C. and for 24 hours at room temperature. The reaction mixture was cooled to 0° C., and 30 ml of water was added. After stirring for 10 minutes, 300 ml of water was further added, and then the mixture was stirred for 1 hour. The crystals precipitated were suction filtered, rinsed with 100 ml of water, and dried at 60° C. under reduced pressure, thereby producing 18.2 g of crude crystals.

The crude crystals obtained above (18.2 g) were recrystallized from methanol-water yielding crystals (15.18 g) of the desired compound (Example Compound 1).

Preparation of Example Compounds 2-11, 13-22, 26, 27, 30-41, 44-47, 50-75, 80-83, 85-94, 96-104, 114, 115, 119, 121, 123, 125-130, 134, 136, and 138-149

The compounds of Examples 2-11, 13-22, 26, 27, 30-41, 44-47, 50-75, 80-83, 85-94, 96-104, 114, 115, 119, 121, 123, 125-130, 134, 136, and 138-149 were prepared by repeating the procedures described in Step 1, or Steps 1 and 2 of Example 1 using the appropriate starting materials.

Example 12

Preparation of 3-(4-benzyloxy-3-methoxyphenyl)imidazo[1,2-a]pyridine (Step 1)

To a solution of 4.23 g (16.9 mmol) of 2-methoxy-4-(4,4,5,5)-tetramethyl-1,3,2-dioxaborane-2-yl phenol in 200 ml dry DMF were added 5.0 g (25.4 mmol) of 3-bromoimidazo[1,2-a]pyridine, 0.39 g (0.34 mmol) of tetrakis(triphenylphosphinato)palladium [0] ($Pd(PPh_3)_4$ wherein Ph is phenyl), and 42.25 ml of 2M aqueous potassium phosphate solution. The mixture was stirred for 20 hours at 80° C. After reaction, DMF was distilled off under reduced pressure, and the residue was purified using a silica gel column (eluant: methanol/methylene chloride=2/98 to 4/96).

The crystals thus obtained were recrystallized using methanol-hexane, thereby producing 2.82 g of 3-(4-hydroxy-3-methoxyphenyl)imidazo[1,2-a]pyridine (yield: 70%). This compound will be referred to as "Example Compound 131".

(Step 2)

To 1 ml of DMF were added 24 mg (0.1 mmol) of the compound obtained in Step 1 (Example Compound 131), 65 mg (0.2 mmol) of cesium carbonate, and 17 mg (0.1 mmol) of benzyl bromide. The mixture was stirred overnight at room temperature. DMF was distilled off under reduced pressure, and the residue was purified using a preparative TLC plate (eluant:methanol/methylene chloride=1/98), thereby giving 28 mg of the desired compound in an yield of 83% ("Example Compound 12").

Preparation of Example Compounds 105-113, 116-118, 120, 122, 124, 132, 133, 135 and 137

The compounds of Examples 105-113, 116-118, 120, 122, 124, 132, 133, 135 and 137 were prepared by repeating the procedures described in Step 1, or Steps 1 and 2 of Example 12 using the appropriate starting materials.

Example 23

Preparation of 6-[4-(4-chlorobenzyloxy)-3-methoxyphenyl]imidazo[2,1-b]thiazole (Step 1)

To 600 ml of an anhydrous THF solution of 100 g 4'-hydroxy-3'-methoxyacetophenone was added 237.5 g phenyltrimethylammonium tribromide over 3 hours at a temperature of 0° C., followed by stirring at 0° C. for 6 hours and at room temperature for 13 hours. The reaction solution thus obtained was concentrated under reduced pressure, mixed with 500 ml of ethyl acetate, and stirred at 0° C. for 1 hour. The precipitated crystals were removed by suction filtration, and the filtered solution was concentrated under reduced pressure, thereby yielding 265 g of oily matter.

This oily matter was dissolved in 400 ml of anhydrous DMF, and the solution thus obtained was added to 60 g of 2-aminothiazole followed by stirring at room temperature for 30 minutes and 40° C. for 3.5 hours. The reaction mixture thus prepared was diluted with 400 ml of ethyl acetate and left for 15 hours at room temperature. The precipitated crystals were collected by suction filtration. The crystals thus obtained were rinsed with ethyl acetate and dried under reduced pressure, thereby producing 153 g of transparent crystalline thiazolium salt of (2-amino-3-[2-(4-hydroxy-3-methoxyphenyl)-2-oxoethyl]thiazol-3-ium bromide).

To 590 ml of n-butanol was added 152.6 g of the thiazolium salt obtained above, and stirred at 100° C. for 45 hours and 120° C. for 1 hour. After cooling, the reaction solution was diluted with 600 ml of ethyl acetate and left to stand 3 hours at room temperature. The precipitated crystals were suction filtered, rinsed with ethyl acetate, and dried under reduced pressure, thereby giving 140.8 g of transparent crystalline 6-(4-hydroxy-3-methoxyphenyl)imidazo[2,1-b]thiazole hydrobromide.

Melting point: 253-254° C.

$^1$H-NMR (DMSO-$d_6$, δ): 8.43 (1H, s), 8.23 (1H, d, J=4.6 Hz), 7.64 (1H, d, J=4.6 Hz), 7.40 (1H, d, J=2.1 Hz), 7.25 (1H, dd, J=2.1, 8.3 Hz), 6.91 (1H, d, J=8.3 Hz), 3.86 (3H, s)

(Step 2)

Potassium carbonate (106 g) was added to 490 ml of an anhydrous DMF suspension of 120 g of the compound obtained in Step 1. After stirring for 2 hours, to the mixture was added 82.9 g of p-chlorobenzyl bromide at 0° C., and stirred for 3 hours at 0° C. and for 42 hours at room temperature. The reaction mixture was mixed with 500 ml of methanol and 450 ml of water, and stirred at 70° C. for 30 minutes. After cooling the mixture to room temperature, the precipitated crystals were suction filtered, rinsed with 50% methanol and water, and dried under reduced pressure, thereby yielding 102 g of transparent crystals of the desired compound ("Example Compound 23").

Preparation of Example Compounds 24, 25, 42, 43, 48, 49 and 84

The compounds of Examples 24, 25, 42, 43, 48, 49 and 84 were prepared by repeating the procedures described in Example 23 using the appropriate starting materials.

Example 28

Preparation of 2-(4-benzyloxy-3-methoxyphenyl)imidazo[1,2-a]pyrimidine

To 30 ml of an acetonitrile solution of 3.9 g (16 mmol) of 4'-hydroxy-3'-methoxy-2-bromoacetophenone was added 3.2 g (34 mmol) of 2-aminopyrimidine, and the mixture was stirred at 65° C. for 2 hours. The precipitated crystals were suction filtered and dissolved in 100 ml of 50% methanol. This solution was mixed with 1.3 g of sodium hydrogencarbonate and stirred at room temperature for 10 minutes. The precipitated crystals were suction filtered, and recrystallized from 50 ml of 50% methanol, thereby giving 2.4 g of 2-(4-hydroxy-3-methoxyphenyl)imidazo[1,2-a]pyrimidine in an yield of 62%.

Melting point: 230-233° C.

$^1$H-NMR (DMSO-$d_6$, δ): 9.21 (1H, s), 8.92 (1H, dd, J=2.1, 6.7 Hz), 8.48 (1H, dd, J=2.1, 4.1 Hz), 8.25 (1H, s), 7.57 (1H, d, J=1.5 Hz), 7.54 (1H, dd, J=1.5, 7.9 Hz), 7.02 (1H, dd, J=4.1, 6.7 Hz), 6.86 (1H, d, J=7.9 Hz), 3.87 (3H, s)

To 4.2 ml of an anhydrous DMF suspension of 0.50 g (2.1 mmol) of the above-obtained compound at a temperature of 0° C. was added 0.34 g (2.5 mmol) of potassium carbonate. The mixture was stirred for 30 minutes, 0.41 g (2.4 mmol) of benzyl bromide was added dropwise followed by stirring for 15 minutes at 0° C., for 20 minutes at room temperature, and for 16 hours at 40° C. The reaction mixture was added to 20 ml of water at room temperature and stirred for 1 hour. The precipitated crystals were then collected by suction filtration, thereby yielding 0.72 g of crude crystals of the desired compound.

These crude crystals were purified using a silica gel column (10 g silica gel, eluant:methylene chloride/methanol=50/1). The desired compound was recrystallized from methylene chloride/diethyl ether in an amount of 0.55 g (yield: 79%).

Preparation of Compound of Example 29

Example Compound 29 was prepared by repeating the procedures described in Example 28 using the appropriate starting materials.

Example 76

Preparation of 2-(4-benzyloxy-3-methoxyphenyl)benzimidazole (Step 1)
In 20 ml of methylene chloride was suspended 2.0 g (7.7 mmol) of 4-benzyloxy-3-methoxy benzoic acid. DMF (0.05 g) and thionyl chloride (0.68 ml) were added to this suspension. The mixture was stirred at 50° C. for 2 hours. At a temperature of 0° C., 20 ml of pyridine wherein 1.1 g (8.0 mmol) of 2-nitroaniline had been dissolved at room temperature was added dropwise to the mixture. The mixture was stirred for 2 hours at room temperature, and water was added thereto to extract the methylene chloride phase. The extract was dried over anhydrous magnesium sulfate, and the solvent was distilled off. The crystals thus obtained were recrystallized using methylene chloride-hexane, thereby yielding 1.5 g of N-(2-nitrophenyl)-4-benzyloxy-3-methoxybenzamide crystals.

$^1$H-NMR (DMSO-d$_6$, δ): 11.32 (1H, br s), 8.99 (1H, d, J=8.0 Hz), 8.27 (1H, d, J=7.6 Hz), 7.70 (1H, dd, J=7.6, 7.6 Hz), 7.59 (1H, d, J=2.0 Hz), 7.51 (1H, dd, J=2.0, 8.4 Hz), 7.30-7.47 (5H, m), 7.20 (1H, dd, J=7.6, 8.0 Hz), 6.99 (1H, d, J=8.4 Hz)

(Step 2)
The crystals (1.5 g) obtained above were suspended in 100 ml of ethanol. This suspension was mixed with 4.5 g of tin chloride 2-hydrate and stirred at 80° C. for 2 hours. The reaction mixture was added to ice-cooled saturated sodium hydrogencarbonate solution (50 ml), and subjected to celite filtration to remove insoluble matter. The filtered solution was diluted with 200 ml of ethyl acetate. The mixture (ethyl acetate phase) was sequentially washed with water and brine. The organic phase (ethyl acetate phase) thus obtained was dried over anhydrous magnesium sulfate. The solvent was distilled off, and the residue was crystallized by diethyl ether, thereby yielding the desired compound in an amount of 1.2 g.

Preparation of the compound of Example 77

Example Compound 77 was prepared by repeating the procedures described in Example 76 using the appropriate starting materials.

Example 78

Preparation of 2-(4-benzyloxy-3-methoxyphenyl)benzothiazole

In methylene chloride (10 ml) was suspended 2.0 g (7.7 mmol) of 4-benzyloxy-3-methoxy benzoic acid. To this suspension was added 0.05 g of DMF and 0.68 ml of thionyl chloride, followed by stirring at 50° C. for 2 hours. This reaction solution was introduced dropwise at 0° C. into a solution wherein 1.2 g (9.3 mmol) of 2-aminothiophenol had been dissolved in 10 ml of pyridine at room temperature. The mixture was further stirred overnight at room temperature, diluted with water, and subjected to ethyl acetate extraction (50 ml×2 times). The extracts were dried over anhydrous magnesium sulfate, and the solvent was distilled off. The residue thus obtained was dissolved in 30 ml of toluene. This toluene solution was heated to reflux overnight while water was distilled off. Toluene was removed from this solution by distillation under reduced pressure, and the residue was purified using a silica gel column (eluant:ethyl acetate/hexane=1/5). The solvent was distilled off under reduced pressure. Using the crystals thus obtained, the desired compound was recrystallized in an amount of 0.18 g from methylene chloride-hexane.

Example 95

Preparation of 4-(4-benzyloxy-3-methoxyphenyl)-2-(4-trifluoromethylphenyl)imidazole Potassium hydrogencarbonate (2.9 g, 29.0 mmol) and α-bromo-4-benzyloxy-3-methoxyacetophenone (1.9 g, 7.3 mmol) were suspended in a mixture of water (2.5 ml) and THF (10 ml). To this suspension was mixed 2.4 g (7.3 mmol) of 4-trifluoromethyl benzamidine at a temperature of 70° C., followed by stirring for 1 hour. The mixture was cooled to room temperature, mixed with 70 ml of ethyl acetate, and stirred for 30 minutes. The solution thus obtained was sequentially washed with water and brine, and dried over anhydrous magnesium sulfate. The solvent was distilled off under reduced pressure. The residue was purified using a silica gel column (eluant:ethyl acetate/hexane=1/1), and the residual compound thus obtained was dissolved in a mixture of 20 ml of ethyl acetate and 5 ml of ethanol. At room temperature 1.9 ml of a 4N 1,4-dioxane solution of hydrochloric acid was added dropwise to this solution. The hydrochloride salt thus produced was filtered and dried at 60° C. under reduced pressure overnight, thereby giving the desired compound in an amount of 2.0 g (yield: 59%).

Preparation of Example Compound 79

The compound of Example 79 was prepared by repeating the procedures described in Example 95 using the appropriate starting materials.

The following Table 1 shows the structures and properties (melting points, $^1$H-NMR spectroscopic data, and mass spectrometric data) of the compounds obtained in the Examples above. Abbreviations in the tables are Me: methyl MeO: methoxy Et: ethyl EtO (OEt): ethoxy n-Pr: n-propyl n-PrO (O-n-Pr): n-propoxy t-Bu: tert-butyl

TABLE 1

| Example No. | Structure | Melting Point (° C.) | ¹H-NMR (CDCl₃) δ, ppm | Mass (EI) |
|---|---|---|---|---|
| 1 | (benzyloxy-methoxyphenyl imidazopyridine) | 128-129.5 | 8.07 (1H, d, J = 6.8 Hz), 7.76 (1H, s), 7.59-7.62 (2H, m), 7.46 (2H, d, J = 7.6 Hz), 7.27-7.39 (4H, m), 7.15 (1H, dd, J = 6.8, 7.6 Hz), 6.93 (1H, d, J = 8.4 Hz), 6.74 (1H, dd, 6.8, 7.6 Hz), 5.19 (2H, s), 4.00 (3H, s) | — |
| 2 | (3-Cl analog) | 103-104 | 8.11 (1H, d, J = 6.4 Hz), 7.74 (1H, d, J = 2.0 Hz), 7.67 (1H, dd, J = 2.0, 8.4 Hz), 7.63 (1H, d, J = 9.2 Hz), 7.47 (2H, d, J = 7.6 Hz), 7.38 (2H, dd, J = 7.2, 7.6 Hz), 7.31-7.33 (1H, m), 7.23-7.26 (1H, m), 6.99 (1H, d, J = 8.4 Hz), 6.94 (1H, dd, 6.4, 8.0 Hz), 5.22 (2H, s), 4.01 (3H, s) | — |
| 3 | (3-Br analog) | 115-117 | 8.17 (1H, d, J = 6.8 Hz), 7.73 (1H, d, J = 2.0 Hz), 7.66 (1H, dd, J = 2.0, 8.4 Hz), 7.62 (1H, d, J = 9.2 Hz), 7.47 (2H, d, J = 7.6 Hz), 7.38 (2H, dd, 7.6, 8.0 Hz), 7.27-7.37 (1H, m), 7.25 (1H, dd, J = 6.8, 9.2 Hz), 6.99 (1H, d, J = 8.4 Hz), 6.93 (1H, dd, J = 6.4, 6.8 Hz), 5.22 (2H, s), 4.01 (3H, s) | — |
| 4 | (2-F benzyl) | 115-117 | 8.08 (dt, J = 7.9, 1.1 Hz, 1H), 7,78 (d, J = 0.5 Hz, 1H), 7.63-7.61 (overlap of 2H), 7.60-7.53 (m, 1H), 7.38 (dd, J = 8.2, 2.2 Hz, 1H), 7.30-7.25 (m, 1H), 7.18-7.04 (overlap of 3H), 6.97 (d, J = 8.2 Hz, 1H), 6.75 (ddd, J = 6.7, 6.6, 1.1 Hz, 1H), 5.26 (s, 2H), 4.01 (s, 3H) | m/z 349.2 (MH⁺) |
| 5 | (3-F benzyl) | 117-118 | 8.08 (dt, J = 7.9, 1.1 Hz, 1H), 7.77 (d, J = 0.6 Hz, 1H), 7.63-7.58 (overlap of 2H), 7.39-7.12 (overlap of 5H), 7.02-6.96 (m, 1H), 6.91 (d, J = 8.2 Hz, 1H), 6.75 (ddd, J = 6.7, 6.6, 1.1 Hz, 1H), 5.17 (s, 2H), 4.01 (s, 3H) | m/z 349.1 (MH+) |
| 6 | (4-F benzyl) | 144-146 | 8.09 (1H, bd, J = 6.6 Hz), 7.78 (1H, s), 7.61 (1H, bd, J = 9.1 Hz), 7.60 (1H, d, J = 2.1 Hz), 7.40-7.45 (2H, m), 7.38 (m), 6.92 (1H, d, J = 8.3 Hz), 6.76 (1H, bt, J = 6.6 Hz), 5.14 (2H, s), 4.00 (3H, s) | — |
| 7 | (4-CF₃ benzyl) | 172-173 | 8.09 (1H, bd, J = 6.6 Hz), 7.78 (1H, s), 7.56-7.64 (6H, m), 7.37 (1H, dd, J = 2.1, 8.3 Hz), 7.13-7.17 (1H, m), 6.90 (1H d, J = 8.3 Hz), 7.76 (1H, bt, J = 6.6 Hz), 5.24 (2H, s), 4.01 (3H, s) | — |

TABLE 1-continued

| Example No. | Structure | Melting Point (° C.) | ¹H-NMR (CDCl₃) δ, ppm | Mass (EI) |
|---|---|---|---|---|
| 8 | 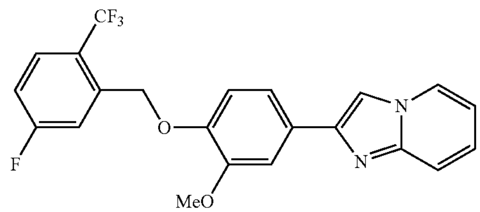 [SMILES: COc1cc(-c2cn3ccccc3n2)ccc1OCc1cc(F)ccc1C(F)(F)F] | 125-126 | 8.10 (1H, bd, J = 6.6 Hz), 7.80 (1H, s), 759-7.69 (4H, m), 7.38 (1H, dd, J = 2.1, 8.3 Hz), 7.13-7.18 (1H, m), 7.04-7.09 (1H, m), 6.89 (1H, d, J = 8.3 Hz), 6.77 (1H, bt, J = 6.6 Hz), 5.37 (2H, s), 4.04 (3H, s) | — |
| 9 | 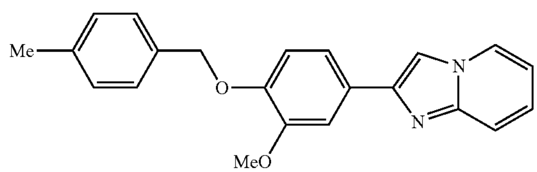 [SMILES: COc1cc(-c2cn3ccccc3n2)ccc1OCc1ccc(C)cc1] | 155-157 | 8.08 (1H, d, J = 7.2 Hz), 7.76 (1H, s), 7.58-7.62 (2H, m), 7.35 (1H, d, J = 8.0 Hz), 7.34 (2H, d, J = 8.0 Hz), 7.17 (2H, d, J = 8.0 Hz), 7.12-7.15 (1H, m), 6.93 (1H, d, J = 8.0 Hz), 6.74 (1H, dd, J = 6.8, 7.2 Hz), 5.16 (2H, s), 4.00 (3H, s), 2.34 (3H, s) | — |
| 10 | 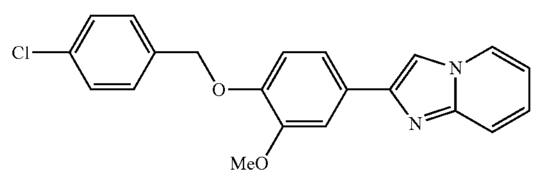 [SMILES: COc1cc(-c2cn3ccccc3n2)ccc1OCc1ccc(Cl)cc1] | 141-143 | 8.07 (br dd, J = 6.9, 0.8 Hz, 1H), 7.77 (s, 1H), 7.62-7.59 (m, 2H), 7.41-7.32 (overlap of 5H), 7.17-7.11 (m, 1H), 6.90 (dd, J = 8.4, 0.7 Hz, 1H), 6.77-6.72 (m, 1H), 5.14 (s, 2H), 4.00 (s, 3H) | m/z 365.2 (MH⁺) |
| 11 | 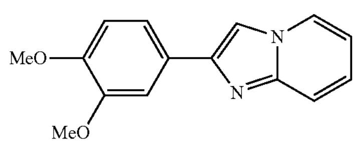 [SMILES: COc1ccc(-c2cn3ccccc3n2)cc1OC] | 88-89 | 8.09 (1H, bd, J = 6.6 Hz), 7.79 (1H, s), 7.61 (1H, d, J = 9.1 Hz), 7.57 (1H, d, J = 2.1 Hz), 7.45 (1H, dd, J = 2.1, 8.3 Hz), 7.12-7.17 (1H, m), 6.93 (1H, d, J = 8.3 Hz), 6.76 (1H, bt, J = 6.6 Hz), 4.00 (3H, s), 3.92 (3H, s) | — |
| 12 | 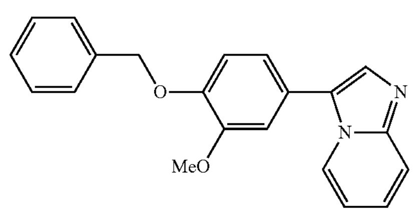 [SMILES: COc1cc(-c2cnc3ccccn23)ccc1OCc1ccccc1] | 129-131 | (CD₃OD) 8.29 (d, 1H), 7.65 (m, 2H), 7.50-7.28 (m, 5H), 7.20 (t, 1H), 7.01 (m, 3H), 6.80 (m, 1H), 5.21 (s, 2H), 3.92 (s, 3H) | m/z 331 (MH⁺) |
| 13 | 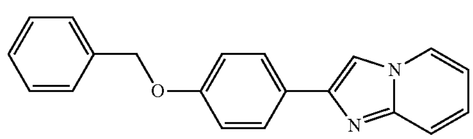 | 171-173 | 8.10 (bd, 1H, J = 6.7 Hz), 7.8-7.9 (2H, m), 7.78 (1H, s), 7.61 (1H, bd, J = 9.1 Hz), 7.3-7.5 (5H, m), 7.1-7.2 (1H, m), 7.0-7.1 (2H, m), 6.76 (1H, bt, J = 6.7 Hz), 5.11 (2H, s) | — |
| 14 | 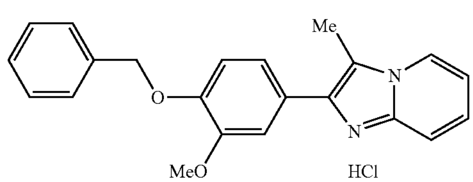 [SMILES: COc1cc(-c2nc3ccccn3c2C)ccc1OCc1ccccc1 ; Cl] | 241-243 | 8.39 (1H, bd, J = 8.5 Hz), 8.15 (1H, bd, J = 6.7 Hz), 7.6-7.7 (2H, m), 7.3-7.5 (6H, m), 7.20 (1H, bd, J = 7.9 Hz), 6.98 (1H, d, J = 8.5 Hz), 5.23 (2H, s), 4.11 (3H, s), 2.73 (3H, s) | — |
| 15 | 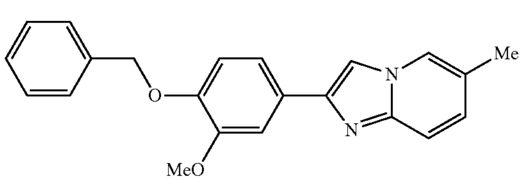 [SMILES: COc1cc(-c2cn3cc(C)ccc3n2)ccc1OCc1ccccc1] | 135-136 | 7.86 (1H, bs), 7.68 (1H, s), 7.59 (1H, d, J = 2.0 Hz), 7.52 (1H, d, J = 9.2 Hz), 7.49 (2H, d, J = 7.6 Hz), 7.27-7.38 (4H, m), 7.00 (1H, dd, J = 2.0, 9.2 Hz), 6.92 (1H, d, J = 8.4 Hz), 5.19 (2H, s), 4.00 (3H, s), 2.30 (3H, s) | — |

TABLE 1-continued

| Example No. | Structure | Melting Point (°C.) | ¹H-NMR (CDCl₃) δ, ppm | Mass (EI) |
|---|---|---|---|---|
| 16 | 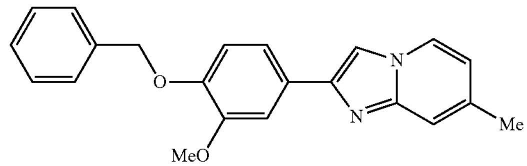 [SMILES: COc1cc(-c2cn3ccc(C)cc3n2)ccc1OCc1ccccc1] | 171-173 | 7.96 (1H, bd, J = 7.0 Hz), 7.69 (1H, s), 7.58 (1H, d, J = 2.0 Hz), 7.45-7.47 (2H, m), 7.27-7.39 (5H, m), 6.93 (1H, d, J = 8.5 Hz), 6.59 (1H, dd, J = 1.8, 7.0 Hz), 5.19 (2H, s), 4.00 (3H, s), 2.39 (3H, s) | — |
| 17 | 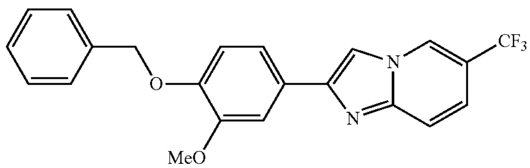 [SMILES: COc1cc(-c2cn3cc(C(F)(F)F)ccc3n2)ccc1OCc1ccccc1] | 172-173 | 8.45-8.47 (1H, m), 7.85 (1H, bs), 7.69 (1H, bd, J = 9.4 Hz), 7.59 (1H, d, J = 2.1 Hz), 7.45-7.47 (2H, m), 7.35-7.39 (3H, m), 7.28-7.32 (2H, m), 6.95 (1H, d, J = 8.5 Hz), 5.20 (2H, s), 4.01 (3H, s) | — |
| 18 | 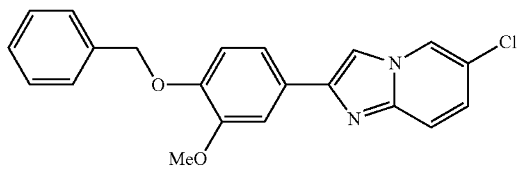 [SMILES: COc1cc(-c2cn3cc(Cl)ccc3n2)ccc1OCc1ccccc1] | 177-179 | 8.12 (1H, m), 7.74 (1H, s), 7.54-7.57 (2H, m), 7.44-7.47 (2H, m), 7.28-7.39 (4H, m), 7.12 (1H, dd, J = 2.1, 9.7 Hz), 6.93 (1H, d, J = 8.2 Hz), 5.20 (2H, s), 4.00 (3H, s) | — |
| 19 | 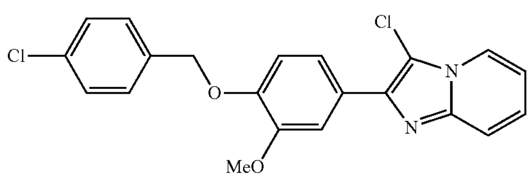 | 139-140 | 8.10 (1H, bd, J = 6.7 Hz), 7.74 (1H, d, J = 2.1 Hz), 7.65 (1H, dd, J = 2.1, 8.5 Hz), 7.62 (1H, bd, J = 9.1 Hz), 7.39-7.42 (2H, m), 7.33-7.36 (2H, m), 7.22-7.26 (1H, m), 6.95 (1H, d, J = 8.5 Hz), 6.93 (1H, bt, J = 6.7 Hz), 5.17 (2H, s), 4.01 (3H, s) | — |
| 20 | 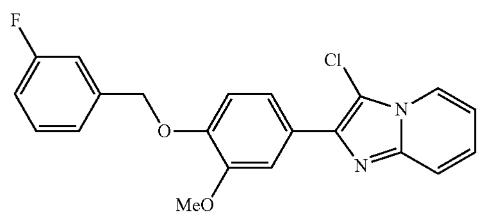 [SMILES: COc1cc(-c2nc3ccccn3c2Cl)ccc1OCc1cccc(F)c1] | 104-105 | 8.11 (1H, bd, J = 6.7 Hz), 7.74 (1H, d, J = 2.1 Hz), 7.66 (1H, dd, J = 2.1, 8.5 Hz), 7.63 (1H, bd, J = 9.1 Hz), 7.31-7.37 (1H, m), 7.19-7.27 (3H, m), 6.97-7.02 (1H, m), 6.96 (1H, d, J = 8.5 Hz), 6.93 (1H, bt, J = 6.7 Hz), 5.21 (2H, s), 4.02 (3H, s) | — |
| 21 | 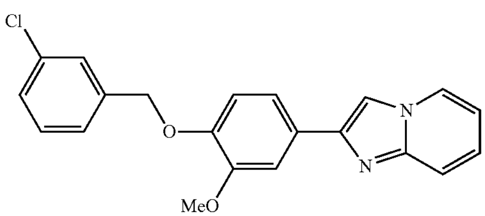 [SMILES: COc1cc(-c2cn3ccccc3n2)ccc1OCc1cccc(Cl)c1] | 114-115 | 8.10 (1H, bd, J = 6.7 Hz), 7.79 (1H, s), 7.60-7.63 (2H, m), 7.48 (1H, bs), 7.38 (1H, dd, J = 2.1, 8.5 Hz), 7.27-7.35 (3H, m), 7.13-7.18 (1H, m), 6.91 (1H, d, J = 8.5 Hz), 6.76 (1H, bt, J = 6.7 Hz), 5.16 (2H, s), 4.02 (3H, s) | — |
| 22 | 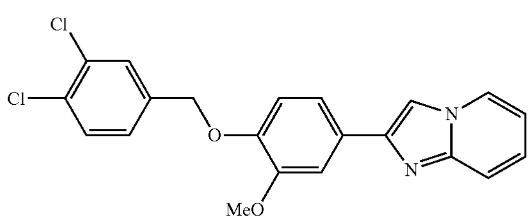 [SMILES: COc1cc(-c2cn3ccccc3n2)ccc1OCc1ccc(Cl)c(Cl)c1] | 138-139 | 8.10 (br d, J = 6.6 Hz, 1H), 7.79 (s, 1H), 7.64-7.57 (overlap of 3H), 7.45 (d, J = 8.5 Hz, 1H), 7.40-7.36 (m, 1H), 7.31-7.26 (m, 1H), 7.19-7.13 (m, 1H), 6.89 (d, J = 8.6 Hz, 1H), 6.77 (ddd, J = 6.8, 6.7, 1.1 Hz, 1H), 5.12 (s, 2H), 4.01 (s, 3H) | m/z 399.1 (M⁺) |
| 23 | 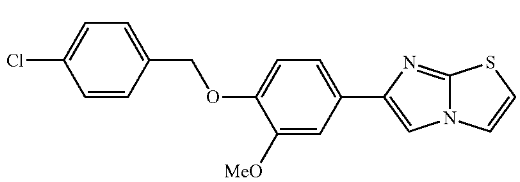 [SMILES: COc1cc(-c2cn3ccsc3n2)ccc1OCc1ccc(Cl)cc1] | 126-128 | 7.66 (1H, s), 7.47 (1H, d, J = 2.1 Hz), 7.42 (1H, d, J = 4.4 Hz), 7.38-7.40 (2H, m), 7.32-7.35 (2H, m), 7.23 (1H, dd, J = 2.1, 8.2 Hz), 6.87 (1H, d, J = 8.2 Hz), 6.82 (1H, d, J = 4.4 Hz), 5.14 (2H, s), 3.98 (3H, s) | — |

TABLE 1-continued

| Example No. | Structure | Melting Point (° C.) | ¹H-NMR (CDCl₃) δ, ppm | Mass (EI) |
|---|---|---|---|---|
| 24 | 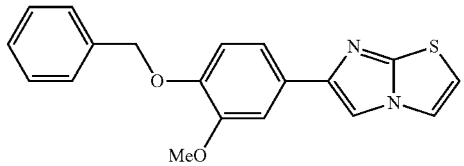 [SMILES: COc1cc(-c2cn3ccsc3n2)ccc1OCc1ccccc1] | 130-132 | 7.66 (1H, s), 7.47 (1H, d, J = 2.1 Hz), 7.43-7.46 (2H, m), 7.42 (1H, bd, J = 4.4 Hz), 7.35-7.39 (2H, m), 7.28-7.32 (1H, m), 7.23 (1H, dd, J = 2.1, 8.2 Hz), 6.90 (1H, d, J = 8.2 Hz), 6.83 (1H, bd, J = 4.4 Hz), 5.19 (2H, s), 3.99 (3H, s) | — |
| 25 | 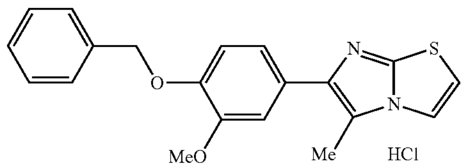 [SMILES: COc1cc(-c2nc3sccn3c2C)ccc1OCc1ccccc1 ; Cl] | 228-230 | (DMSO-d₆) 8.29 (1H, d, J = 4.6 Hz), 7.66 (1H, d, J = 4.6 Hz), 7.32-7.48 (6H, m), 7.19 (2H, m), 5.16 (2H, s), 3.86 (3H, s), 2.63 (3H, s) | — |
| 26 | 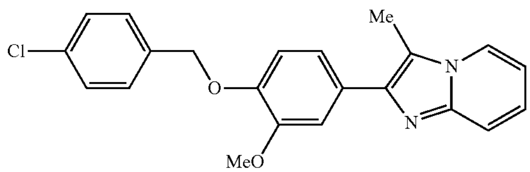 [SMILES: COc1cc(-c2nc3ccccn3c2C)ccc1OCc1ccc(Cl)cc1] | 114-115 | 7.89 (1H, bd, J = 6.7 Hz), 7.63 (1H, bd, J = 9.1 Hz), 7.46 (1H, d, J = 2.1 Hz), 7.40-7.42 (1H, m), 7.33-7.36 (1H, m), 7.20 (1H, dd, J = 2.1, 8.5 Hz), 7.15-7.19 (1H, m), 6.94 (1H, d, J = 8.5 Hz), 6.85 (1H, dt, J = 0.9, 6.7 Hz), 5.17 (2H, s), 3.99 (1H, s), 2.63 (3H, s) | — |
| 27 | 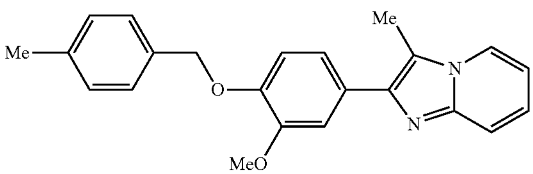 [SMILES: COc1cc(-c2nc3ccccn3c2C)ccc1OCc1ccc(C)cc1] | 118-120 | 7.88 (1H, bd, J = 6.7 Hz), 7.63 (1H, bd, J = 9.1 Hz), 7.44 (1H, d, J = 2.1 Hz), 7.35 (2H, d, J = 7.9 Hz), 7.14-7.20 (4H, m), 6.96 (1H, d, J = 8.2 Hz), 6.84 (1H, dt, J = 1.2, 6.7 Hz), 5.18 (2H, s), 3.98 (3H, s), 2.62 (3H, s), 2.35 (3H, s) | — |
| 28 | 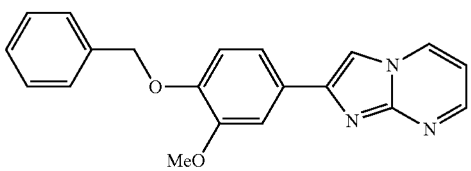 | 168-169 | 8.50 (1H, dd, J = 1.8, 4.1 Hz), 8.39 (1H, dd, J = 1.8, 6.7 Hz), 7.75 (1H, d, J = 2.1 Hz), 7.73 (1H, s), 7.29-7.47 (6H, m), 6.93 (1H, d, J = 8.2 Hz), 6.83 (1H, dd, J = 4.1, 6.7 Hz), 5.21 (2H, s), 4.01(3H, s) | — |
| 29 | 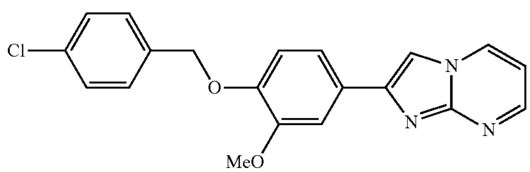 | 216-218 | 8.51(1H, dd, J = 2.1, 4.1 Hz), 8.40 (1H, dd, J = 2.1, 6.7 Hz), 7.76 (1H, d, J = 1.8 Hz), 7.75 (1H, s), 7.39-7.42 (3H, m), 7.33-7.39 (2H, m), 6.90 (1H, d, J = 8.5 Hz), 6.85 (1H, dd, J = 4.1, 6.7 Hz), 5.17 (2H, s), 4.01 (3H, s) | — |
| 30 | 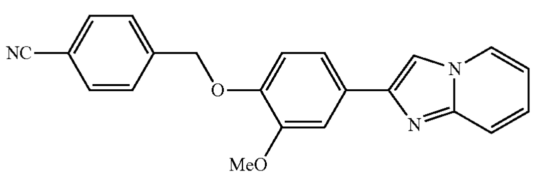 [SMILES: COc1cc(-c2cn3ccccc3n2)ccc1OCc1ccc(C#N)cc1] | 175-177 | 8.11 (br d, J = 6.6 Hz, 1H), 7.80 (s, 1H), 7.69-7.57 (overlap of 6H), 7.38 (br dd, J = 8.4, 1.8 Hz, 1H), 7.20-7.15 (m, 1H), 6.88 (br d, J = 8.5 Hz, 1H), 6.78 (br t, 3 J = 6.7 Hz, 1H), 5.24 (s, 2H), 4.02 (s, 3H) | m/z 356.2 (MH⁺) |
| 31 | 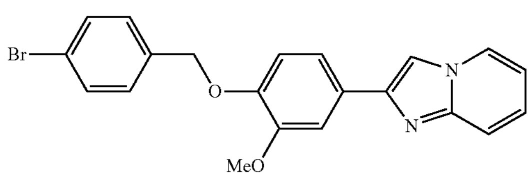 [SMILES: COc1cc(-c2cn3ccccc3n2)ccc1OCc1ccc(Br)cc1] | 136-137 | 8.09 (1H, bd, J = 6.7 Hz), 7.78 (1H, s), 7.60-7.63 (2H, m), 7.49 (2H, d, J = 8.2 Hz), 7.37 (1H, dd, J = 2.1, 8.2 Hz), 7.33 (2H, d, J = 8.2 Hz), 7.13-7.17 (1H, m), 6.89 (1H, d, J = 8.2 Hz), 6.76 (1H, bt, J = 6.7 Hz), 5.13 (2H, s), 4.00 (3H, s) | — |

TABLE 1-continued

| Example No. | Structure | Melting Point (° C.) | ¹H-NMR (CDCl₃) δ, ppm | Mass (EI) |
|---|---|---|---|---|
| 32 | 4-Cl-benzyloxy-3-methoxyphenyl-(6-methyl-imidazo[1,2-a]pyridin-2-yl) | 140-142 | 7.88 (1H, bs), 7.70 (1H, s), 7.59 (1H, d, J = 1.8 Hz), 7.51 (1H, d, J = 9.1 Hz), 7.38-7.40 (2H, m), 732-7.36 (3H, m), 7.00 (1H, dd, J = 1.5, 9.1 Hz), 6.89 (1H, d, J = 8.5 Hz), 5.15 (2H, s), 4.00 (3H, s), 2.31(3H, s) | — |
| 33 | benzyloxy-3-methoxyphenyl-(5-methyl-imidazo[1,2-a]pyridin-2-yl) | 130-132 | 7.67 (s, 1H), 7.63 (d, J = 1.9 Hz, 1H), 7.55 (d, J = 9.1 Hz, 1H), 7.49-7.26 (overlap of 6H), 7.15 (dd, J = 9.0, 6.9 Hz, 1H), 6.95 (d, J = 8.3 Hz, 1H), 6.61 (br d, J = 6.8 Hz, 1H), 5.21 (s, 2H), 4.02 (s, 3H), 2.62 (s, 3H) | m/z 345.1 (MH⁺) |
| 34 | benzyloxy-3-methoxyphenyl-(8-methyl-imidazo[1,2-a]pyridin-2-yl) | 99-100 | 7.98 (d, 1H), 7.77 (s, 1H), 7.60 (s, 1H), 7.25-7.50(m, 6H), 6.94(d, 2H), 6.65(t, 1H), 5.20(s, 2H), 4.00(s, 3H), 2.65(s, 3H) | m/z 345 (MH⁺) |
| 35 | 4-MeO-benzyloxy-3-methoxyphenyl-imidazo[1,2-a]pyridin-2-yl | 165-167 | 8.09 (1H, bd, J = 7.0 Hz), 7.78 (1H, s), 7.61 (1H, bd, J = 9.1 Hz), 7.59 (1H, d, J = 2.1 Hz), 7.36-7.40 (3H, m), 7.12-7.17 (1H, m), 6.95 (1H, d, J = 8.2 Hz), 6.88-6.92 (2H, m), 6.76 (1H, bt, J = 7.0 Hz), 5.12 (2H, s), 3.99 (3H, s), 3.80 (3H, s) | — |
| 36 | 4-MeO-benzyloxyphenyl-imidazo[1,2-a]pyridin-2-yl | 215-218 | (DMSO-d₆) 8.49 (1H, d, J = 6.7 Hz), 8.28 (1H, s), 7.88 (2H, d, J = 8.8 Hz), 7.54 (1H, d, J = 9.1 Hz), 7.40 (2H, d, J = 8.8 Hz), 7.20-7.23 (1H, m), 7.06 (2H, d, J = 8.5 Hz), 6.95 (2H, d, J = 8.5 Hz), 6.87 (1H, dt, J = 0.9, 6.7 Hz), 5.06 (2H, s), 3.76 (3H, s) | — |
| 37 | 4-Cl-benzyloxyphenyl-imidazo[1,2-a]pyridin-2-yl | 229-231 | (DMSO-d₆) 8.49 (1H, d, J = 6.7 Hz), 8.29 (1H, s), 7.89 (2H, d, J = 8.8 Hz), 7.46-7.56 (5H, m), 7.20-7.23 (1H, m), 7.08 (2H, d, J = 8.8 Hz), 6.87 (1H, bt, J = 6.7 Hz), 5.16 (2H, s) | — |
| 38 | 4-O₂N-benzyloxy-3-methoxyphenyl-imidazo[1,2-a]pyridin-2-yl | 197-200 | 8.21-8.25 (2H, m), 8.10 (1H, bd, J = 6.7 Hz), 7.80 (1H, s), 7.60-7.65 (4H, m), 7.38 (1H, dd, J = 2.1, 8.2 Hz), 7.14-7.19 (1H, m), 6.89 (1H, d, J = 8.2 Hz), 6.77 (1H, bt, J = 6.7 Hz), 5.28 (2H, s), 4.03 (3H, s) | — |
| 39 | benzyloxy-3-methylphenyl-imidazo[1,2-a]pyridin-2-yl | 123-124 | 8.09-8.11 (1H, m), 7.80 (1H, d, J = 2.3 Hz), 7.78 (1H, s), 7.72 (1H, dd, J = 2.3, 8.5 Hz), 7.61 (1H, bd, J = 9.1 Hz), 7.31-7.48 (5H, m), 7.12-7.16 (1H, m), 6.95 (1H, d, J = 8.5 Hz), 6.75 (1H, dt, J = 1.2, 6.7 Hz), 5.13 (2H, s), 2.36 (3H, s) | — |

TABLE 1-continued

| Example No. | Structure | Melting Point (°C.) | ¹H-NMR (CDCl₃) δ, ppm | Mass (EI) |
|---|---|---|---|---|
| 40 | 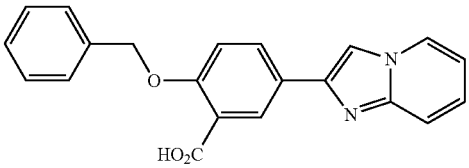 [SMILES: O=C(O)c1cc(-c2cn3ccccc3n2)ccc1OCc1ccccc1] | 239-240 | (DMSO-d6) 8.49 (1H, bd, J = 6.6 Hz), 837 (1H, s), 8.26 (1H, d, J = 2.5 Hz), 8.04 (1H, dd, J = 2.5, 8.7 Hz), 7.51-7.57 (3H, m), 7.21-7.42 (5H, m), 6.88 (1H, bt, J = 6.6 Hz), 5.25 (2H, s) | — |
| 41 | 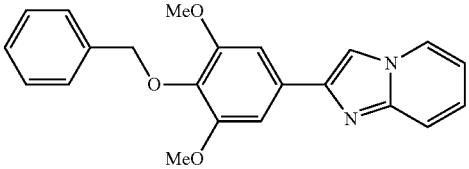 [SMILES: COc1cc(-c2cn3ccccc3n2)cc(OC)c1OCc1ccccc1] | 154-155 | (CD₃OD) 8.42 (br d, 1H), 8.21 (s, 1H), 7.60-7.47 (overlap of 3H), 7.19-7.12 (overlap of 6H), 6.94 (br t, 1H), 5.01 (s, 2H), 3.93 (s, 6H) | m/z 361.2 (MH⁺) |
| 42 | 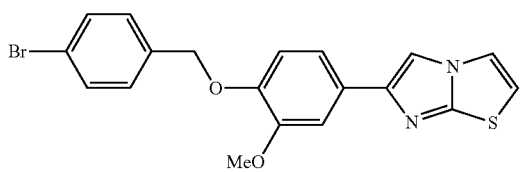 [SMILES: COc1cc(-c2cn3ccsc3n2)ccc1OCc1ccc(Br)cc1] | 134-136 | 7.66 (1H, s), 7.48-7.50 (2H, m), 7.47 (1H, d, J = 2.1 Hz), 7.41 (1H, d, J = 4.7 Hz), 7.32-7.34 (2H, m), 7.23 (1H, dd, J = 2.1. 8.2 Hz), 6.86 (1H, d, J = 8.2 Hz), 6.81 (1H, d, J = 4.7 Hz), 5.12 (2H, s), 3.98 (3H, s) | — |
| 43 | 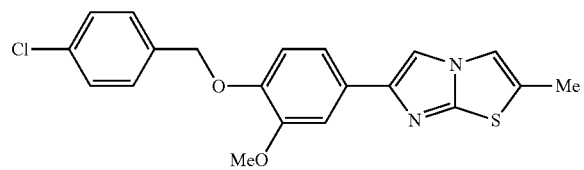 [SMILES: COc1cc(-c2cn3cc(C)sc3n2)ccc1OCc1ccc(Cl)cc1] | 156-158 | 7.53 (1H, s), 7.44 (1H, d, J = 2.1 Hz), 7.37-7.39 (2H, m), 7.31-7.34 (2H, m), 7.20 (1H, dd, J = 2.1, 8.3 Hz), 7.10-7.11 (1H, m), 6.85 (1H, d, J = 8.3 Hz), 5.13 (2H, s), 3.97 (3H, s), 2.42 (3H, d, J = 1.7 Hz) | — |
| 44 | 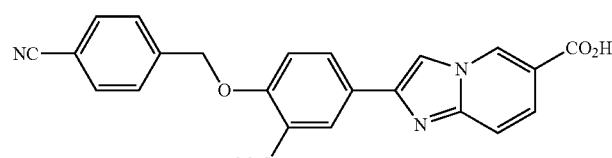 | 242-243 | (DMSO-d₆) 9.17 (1H, s), 8.46 (1H, s), 7.88 (2H, d, J = 8.3 Hz), 7.59-7.67 (5H, m), 7.47 (1H, dd, J = 2.1, 8.3 Hz), 7.10 (1H, d, J = 8.3 Hz), 5.26 (2H, s), 3.89 (3H, s) | — |
| 45 | 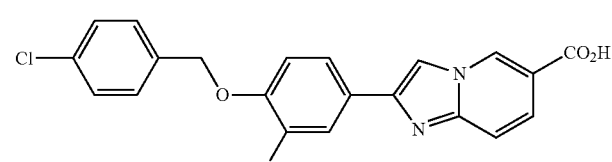 | 251-253 | (DMSO-d₆) 9.17 (1H, s), 8.45 (1H, s), 7.58-7.64 (3H, m), 7.45-7.51 (5H, m), 7.11 (1H, d, J = 8.3 Hz), 5.14 (2H, s), 3.87 (3H, s) | — |
| 46 | 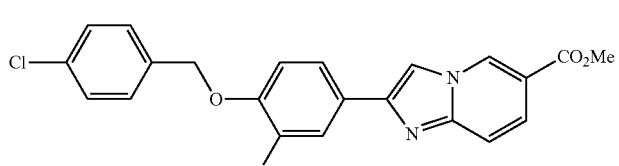 | 182-183 | 8.88 (1H, s), 7.84 (1H, s), 7.71 (1H, dd, J = 1.7, 9.6 Hz), 7.59-7.61 (2H, m), 7.32-7.40 (5H, m), 6.91 (1H, d, J = 8.3 Hz), 5.16 (2H, s), 4,00 (3H, s), 3.95 (3H, s) | — |
| 47 | 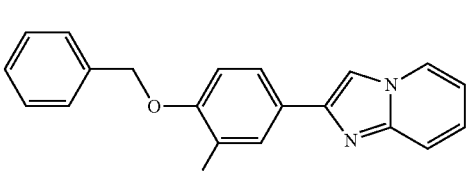 | 179-181 | 8.37 (1H, d, J = 2.1 Hz), 8.10 (1H, bd, J = 6.6 Hz), 8.07 (1H, dd, J = 2.1, 8.7 Hz), 7.83 (1H, s), 7.61 (1H, bd, J = 9.1 Hz), 7.50-7.51 (2H, m), 7.37-7.41 (2H, m), 7.29-7.33 (1H, m), 7.14-7.19 (1H, m), 7.09 (1H, d, J = 8.7 Hz), 6.77 (1H, dt, J = 0.8, 6.6 Hz), 5.24 (2H, s), 3.93 (3H, s) | — |

TABLE 1-continued

| Example No. | Structure | Melting Point (° C.) | $^1$H-NMR (CDCl$_3$) δ, ppm | Mass (EI) |
|---|---|---|---|---|
| 48 | (4-NC-benzyl)-O-[3-MeO-phenyl]-imidazo[2,1-b]thiazole | 179-181 | 7.68 (1H, s), 7.67 (2H, bd, J = 8.2 Hz), 7.57 (2H, bd, J = 8.2 Hz), 7.49 (1H, d, J = 2.1 Hz), 7.42 (1H, d, J = 4.4 Hz), 7.24 (1H, dd, J = 2.1, 8.2 Hz), 6.85 (1H, d, J = 8.2 Hz), 6.82 (1H, d, J = 4.4 Hz), 5.22 (2H, s), 3.99 (3H, s) | — |
| 49 | (4-O$_2$N-benzyl)-O-[3-MeO-phenyl]-imidazo[2,1-b]thiazole | 189-191 | 8.23-8.25 (2H, m), 7.67 (1H, s), 7.62-7.65 (2H, m), 7.49 (1H, d, J = 2.1 Hz), 7.42 (1H, d, J = 4.7 Hz), 7.24 (1H, dd, J = 2.1, 8.2 Hz), 6.86 (1H, d, J = 8.2 Hz), 6.82 (1H, d, J = 4.7 Hz), 5.27 (2H, s), 4.00 (3H, s) | — |
| 50 | (4-MeO$_2$C-benzyl)-O-[3-MeO-phenyl]-imidazo[1,2-a]pyridine | 125-126 | 8.10 (1H, bd, J = 6.6 Hz), 8.04 (2H, d, J = 8.3 Hz), 7.78 (1H, s), 7.62 (1H, bd, J = 9.1 Hz), 7.61 (1H, d, J = 1.7 Hz), 7.53 (2H, d, J = 8.3 Hz), 7.36 (1H, dd, J = 1.7, 8.3 Hz), 7.13-7.18 (1H, m) 6.89 (1H, d, J = 8.3 Hz), 6.76 (1H, dd, J = 6.6, 7.1 Hz), 5.25 (2H, s), 4.02 (3H, s), 3.91 (3H, s) | — |
| 51 | (4-HO$_2$C-benzyl)-O-[3-MeO-phenyl]-imidazo[1,2-a]pyridine | 245-247 | (DMSO-d$_6$) 8.84 (1H, bd, J = 6.6 Hz), 8.76 (1H, s), 7.87-7.99 (4H, m), 7.74 (1H, d, J = 2.1 Hz), 7.57-7.59 (3H, m), 7.46 (1H, bt, J = 6.6 Hz), 7.23 (1H, d, J = 8.7 Hz), 5.28 (2H, s), 3.93 (3H, s) | — |
| 52 | benzyl-O-[3-MeO-phenyl]-6,8-dichloroimidazo[1,2-a]pyridine | 163-165 | 8.82 (s, 1H), 8.45 (s, 1H), 7.30-7.65 (m, 8H), 7.13(d, 1H), 5.14(s, 2H), 3.87(s, 3H) | m/z 399, 401 (MH$^+$) |
| 53 | benzyl-O-[3-MeO-phenyl]-6-CF$_3$-8-Cl-imidazo[1,2-a]pyridine | 155-156 | 8.40-8.36 (m, 1H), 7.88 (s, 1H), 7.60 (d, J = 1.9 Hz, 1H), 7.46-7.29 (overlap of 7H), 6.93 (d, J = 8.2 Hz, 1H), 5.19 (s, 2H), 4.00 (s, 3H) | m/z 433.1 (MH$^+$) |
| 54 | benzyl-O-[3-MeO-phenyl]-8-OH-imidazo[1,2-a]pyridine | 187-189 | 7.72 (1H, bs), 7.71 (1H, bd, J = 6.4 Hz), 7.47 (1H, d, J = 2.1 Hz), 7.42-7.44 (2H, m), 7.34-7.38 (2H, m), 7.27-7.31(1H, m), 7.25 (1H, dd, J = 2.1, 8.5 Hz), 6.86 (1H, d, J = 8.5 Hz), 6.71 (1H, dd, J = 6.4, 7.6 Hz), 6.64 (1H, bd, J = 7.6 Hz), 5.17 (2H, s), 3.75 (3H, s) | — |

TABLE 1-continued

| Example No. | Structure | Melting Point (° C.) | $^1$H-NMR (CDCl$_3$) δ, ppm | Mass (EI) |
|---|---|---|---|---|
| 55 | (structure) | 140-141 | 7.78 (s, 1H), 7.75(d, 1H), 7.70(d, 1H), 7.25-7.55(m, 11H), 6.95(d, 1H), 6.60(t, 1H), 5.40(s, 2H), 5.20(s, 2H), 4.00(s, 3H) | m/z 437 (MH$^+$) |
| 56 | (structure) | 155-157 | 7.96 (1H, bs), 7.73-7.76 (2H, m), 7.68 (1H, bd, J = 1.8 Hz), 7.48-7.51 (2H, m), 7.31-7.36 (3H, m), 7.17 (1H, bd, J = 9.1 Hz), 6.88 (1H, d, J = 8.2 Hz), 5.13 (2H, s), 4.03 (3H, s), 2.35 (3H, s) | — |
| 57 | (structure) | 168-169 | 7.97 (1H, bs), 7.78 (1H, bd, J = 9.4 Hz), 7.73 (1H, s), 7.72 (1H, d, J = 2.1 Hz), 7.67 (2H, d, J = 8.5 Hz), 7.57 (2H, d, J = 8.5 Hz), 7.37 (1H, dd, J = 2.1, 8.2 Hz), 7.20 (1H, bd, J = 9.4 Hz), 6.87 (1H, d, J = 8.2 Hz), 5.24 (2H, s), 4.05 (3H, s), 2.37 (3H, s) | — |
| 58 | (structure) | 111-113 | 8.10 (1H, bd, J = 6.6 Hz), 7.80 (1H, s), 7.61-7.63 (2H, m), 7.44 (1H, t, J = 7.9 Hz), 7.39 (1H, dd, J = 2.1, 8.3 Hz), 7.25-7.31 (2H, m), 7.14-7.18 (1H, m), 6.93 (1H, d, J = 8.3 Hz), 6.77 (1H, dt, J = 0.8, 6.6 Hz), 5.20 (2H, s), 4.00 (3H, s) | — |
| 59 | (structure) | 169-171 | 8.10 (1H, d, J = 6.6 Hz), 7.76 (1H, s), 7.60 (1H, d, J = 8.3 Hz), 7.49-7.53 (2H, m), 7.36-7.45 (5H, m), 7.12-7.17 (1H, m), 7.00 (1H, d, J = 8.3 Hz), 6.76 (1H, dt, J = 0.8, 6.6 Hz), 5.70 (1H, s), 5.16 (2H, s) | — |
| 60 | (structure) | 157-158 | 8.09 (1H, bd, J = 6.6 Hz), 7.77 (1H, s), 7.59-7.62 (2H, m), 7.45-7.48 (2H, m), 7.28-739 (4H, m), 7.12-7.17 (1H, m), 6.95 (1H, d, J = 8.3 Hz), 6.76 (1H, bt, J = 6.6 Hz), 5.19 (2H, s), 4.27 (2H, q, J = 7.1 Hz), 1.50 (3H, t, J = 7.1 Hz) | — |
| 61 | (structure) | 126-127 | 8.08-8.10 (1H, m), 7.78 (1H, s). 7.59-7.63 (2H, m), 7.46-7.48 (2H, m), 7.28-7.40 (4H, m), 7.12-7.17 (1H, m), 6.96 (1H, d, J = 8.5 Hz), 6.76 (1H, dt, J = 1.2, 6.7 Hz), 5.18 (2H, s), 4.13 (2H, t, J = 6.8 Hz), 1.86-1.95 (2H, m), 1.08 (3H, t, J = 7.6 Hz) | — |

TABLE 1-continued

| Example No. | Structure | Melting Point (° C.) | ¹H-NMR (CDCl₃) δ, ppm | Mass (EI) |
|---|---|---|---|---|
| 62 | 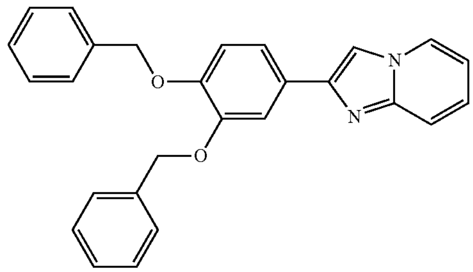 [SMILES: c1ccc(COc2ccc(-c3cn4ccccc4n3)cc2OCc2ccccc2)cc1] | 122-124 | 8.09 (1H, bd, J = 6.6 Hz), 7.74 (1H, s), 7.66 (1H, d, J = 2.1 Hz), 7.61 (1H, d, J = 8.7 Hz), 7.28-7.51 (11H, m), 7.12-1.11 (1H, m), 7.00 (1H, d, J = 8.3 Hz), 6.76 (1H, bt, J = 6.6 Hz), 5.26 (2H, s), 5.19 (2H, s) | — |
| 63 | 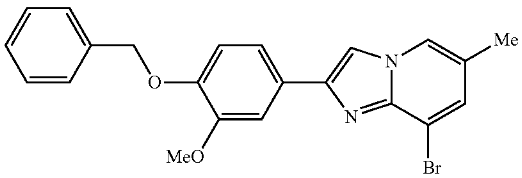 [SMILES: COc1cc(-c2cn3cc(C)cc(Br)c3n2)ccc1OCc1ccccc1] | 136-137 | 7.84 (1H, bs), 7.74 (1H, s), 7.59 (1H, d, J = 2.1 Hz), 7.43-7.46 (2H, m), 7.27-7.38 (5H, m), 6.91 (1H, d, J = 8.3 Hz), 5.19 (2H, s), 4.00 (3H, s), 2.30 (3H, s) | — |
| 64 | 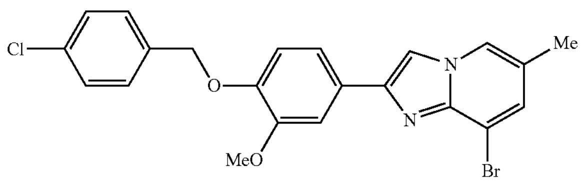 [SMILES: COc1cc(-c2cn3cc(C)cc(Br)c3n2)ccc1OCc1ccc(Cl)cc1] | 136-138 | 7.86 (1H, bs), 7.76 (1H, s), 7.60 (1H, d, J = 2.1 Hz), 7.29-7.40 (6H, m), 6.88 (1H, d, J = 8.3 Hz), 5.14 (2H, s), 4.00 (3H, s), 2.31 (3H, s) | — |
| 65 | 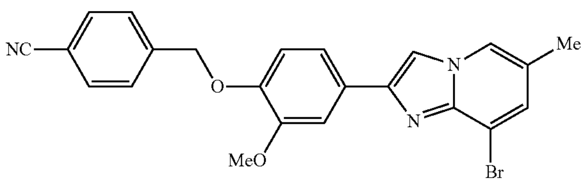 [SMILES: COc1cc(-c2cn3cc(C)cc(Br)c3n2)ccc1OCc1ccc(C#N)cc1] | 175-176 | 7.86 (1H, bs), 7.77 (1H, s), 7.66 (2H, d, J = 7.9 Hz), 7.62 (1H, d, J = 2.1 Hz), 7.56 (2H, d, J = 7.9 Hz), 7.38 (1H, dd, J = 2.1, 8.3 Hz), 7.30 (1H, d, J = 1.2 Hz), 6.86 (1H, d, J = 8.3 Hz), 5.23 (2H, s), 4.02 (3H, s), 2.31 (3H, s) | — |
| 66 | 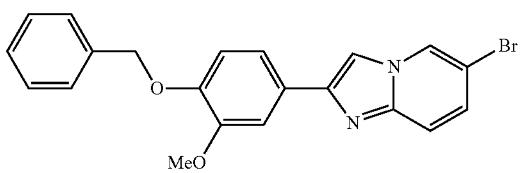 [SMILES: COc1cc(-c2cn3cc(Br)ccc3n2)ccc1OCc1ccccc1] | 175-176 | 8.25-8.23 (m, 1H), 7.74 (s, 1H), 7.57 (d, J = 1.8 Hz, 1H), 7.52-7.19 (overlap of 8H), 6.93 (d, J = 8.3 Hz, 1H), 5.20 (s, 2H), 4.00 (s, 3H) | m/z 409.1 (M⁺) |
| 67 | 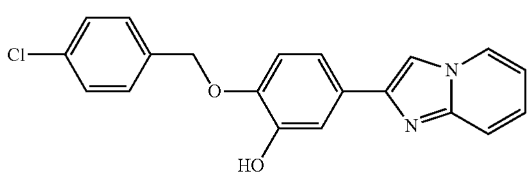 [SMILES: Oc1cc(-c2cn3ccccc3n2)ccc1OCc1ccc(Cl)cc1] | 206-208 | (DMSO-d₆) 9.17 (1H, s), 8.48 (1H, d, J = 7.1 Hz). 8.21 (1H, s), 7.44-7.53 (6H, m), 7.31 (1H, dd, J = 1.7, 8.3 Hz), 7.18-7.22 (1H, m), 7.01 (1H, d, J = 8.3 Hz), 6.85 (1H, bt, J = 6.6 Hz), 5.14 (2H, s) | — |
| 68 | 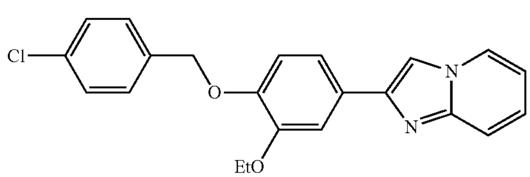 | 136-137 | 8.09 (1H, bd, J = 6.6 Hz), 7.78 (1H, s), 7.59-7.62 (2H, m), 7.32-7.41 (5H, m), 7.13-7.17 (1H, m), 6.92 (1H, d, J = 8.3 Hz), 6.76 (1H, dt, J = 0.8, 6.6 Hz), 5.14 (2H, s), 4.23 (2H, q, J = 7.1 Hz), 1.49 (3H, t, J = 7.1 Hz) | — |
| 69 | 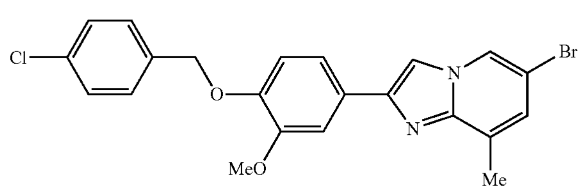 [SMILES: COc1cc(-c2cn3cc(Br)cc(C)c3n2)ccc1OCc1ccc(Cl)cc1] | 155-156 | 8.10 (1H, bs), 7.70 (1H, s), 7.57 (1H, d, J = 2.1 Hz), 7.32-7.39 (5H, m), 7.03 (1H, bs), 6.89 (1H, d, J = 8.3 Hz), 5.15 (2H, s), 4.00 (3H, s). 2.64 (3H, s) | — |

TABLE 1-continued

| Example No. | Structure | Melting Point (° C.) | ¹H-NMR (CDCl₃) δ, ppm | Mass (EI) |
|---|---|---|---|---|
| 70 | 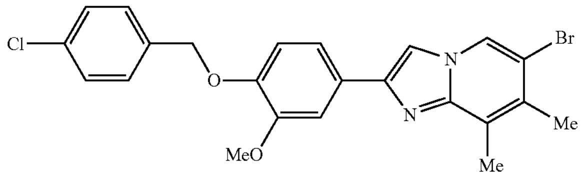 [SMILES: COc1cc(-c2cn3cc(Br)c(C)c(C)c3n2)ccc1OCc1ccc(Cl)cc1] | 166-167 | 8.19 (1H, s), 7.66 (1H, s), 7.59 (1H, d, J = 1.8 Hz), 7.32-7.40 (5H, m), 6.89 (1H, d, J = 8.5 Hz), 5.15 (2H, s), 4.00 (3H, s), 2.68 (3H, s), 2.42 (3H, s) | — |
| 71 | 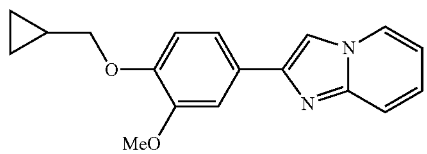 [SMILES: COc1cc(-c2cn3ccccc3n2)ccc1OCC1CC1] | 121-123 | 8.10 (1H, bd, J = 6.6 Hz), 7.79 (1H, s), 7.62 (1H, bd, J = 9.1 Hz), 7.57 (1H, d, J = 2.1 Hz), 7.42 (1H, dd, J = 2.1, 8.3 Hz), 7.13-7.18 (1H, m), 6.92 (1H, d, J = 8.3 Hz), 6.77 (1H, bt, J = 6.6 Hz), 4.00 (3H, s), 3.90 (2H, d, J = 7.1 Hz), 1.31-1.42 (1H, m), 0.63-0.68 (2H, m), 0.35-0.40 (2H, m) | — |
| 72 | 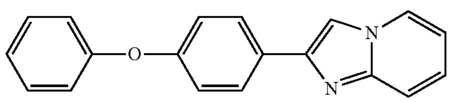 [SMILES: c1ccc(Oc2ccc(-c3cn4ccccc4n3)cc2)cc1] | 164-165 | 8.11 (1H, bd, J = 7.1 Hz), 7.90-7.94 (2H, m), 7.81 (1H, s), 7.62 (1H, d, J = 9.1 Hz), 7.32-7.38 (2H, m), 7.04-7.19 (6H, m), 6.77 (1H, bt, J = 7.1 Hz) | — |
| 73 | 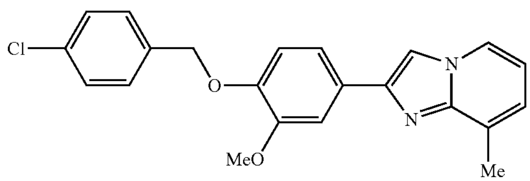 [SMILES: COc1cc(-c2cn3cccc(C)c3n2)ccc1OCc1ccc(Cl)cc1] | 132-133 | 7.96 (1H, bd, J = 6.6 Hz), 7.75 (1H, s), 7.60 (1H, d, J = 1.7 Hz), 7.37-7.40 (3H, m), 7.31-7.35 (2H, m), 6.93 (1H, bd, J = 6.6 Hz), 6.90 (1H, d, J = 8.3 Hz), 6.66 (1H, t, J = 6.6 Hz), 5.15 (2H, s), 4.01 (3H, s), 2.66 (3H, s) | — |
| 74 | 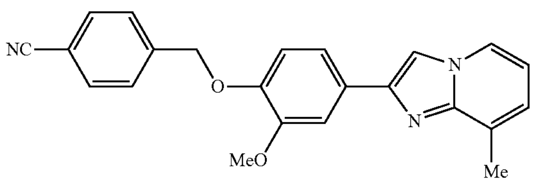 [SMILES: COc1cc(-c2cn3cccc(C)c3n2)ccc1OCc1ccc(C#N)cc1] | 144-146 | 7.97 (1H, bd, J = 6.6 Hz), 7.76 (1H, s), 7.66 (2H, d, J = 8.7 Hz), 7.61 (1H, d, J = 2.1 Hz), 7.57 (2H, d, J = 8.7 Hz), 7.39 (1H, dd, 2.1, 8.3 Hz), 6.94 (1H, bd, J = 7.1 Hz), 6.87 (1H, d, J = 8.3 Hz), 6.67 (1H, dd, J = 6.6, 7.1 Hz), 5.23 (2H, s), 4.02 (3H, s), 2.66 (3H, s) | — |
| 75 | 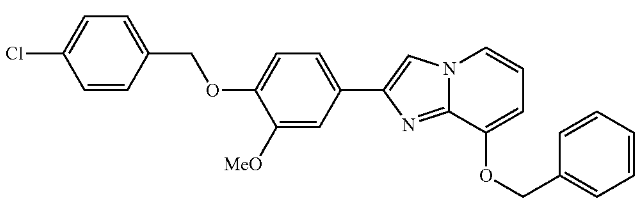 [SMILES: COc1cc(-c2cn3cccc(OCc4ccccc4)c3n2)ccc1OCc1ccc(Cl)cc1] | 164-166 | 7.76 (1H, s), 7.73 (1H, bd, J = 6.6 Hz), 7.64 (1H, bs), 7.50-7.52 (2H, m), 7.29-7.40 (8H, m), 6.88 (1H, d, J = 8.3 Hz), 6.59 (1H, dd, J = 6.6, 7.1 Hz), 6.44 (1H, bd, J = 7.1 Hz), 5.39 (2H, s), 5.14 (2H, s), 3.99 (3H, s) | — |
| 76 | 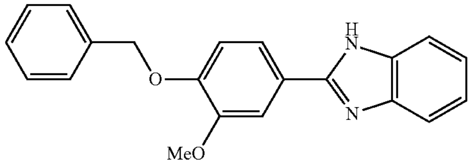 [SMILES: COc1cc(-c2nc3ccccc3[nH]2)ccc1OCc1ccccc1] | 219-221 | (DMSO-d₆) 12.74 (1H, s), 7.80 (1H, d, J = 2.1 Hz), 7.72 (1H, dd, J = 2.1, 8.3 Hz), 7.61-7.64 (1H, m), 7.47-7.52 (3H, m), 7.40-7.44 (2H, m), 7.33-7.37 (1H, m), 7.22 (1H, d, J = 8.3 Hz), 7.14-7.19 (2H, m), 5.18 (2H, s), 3.90 (3H, s) | — |
| 77 | 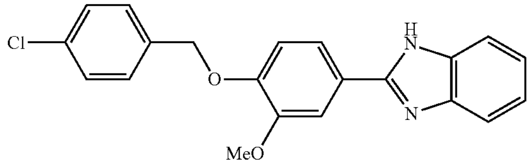 [SMILES: COc1cc(-c2nc3ccccc3[nH]2)ccc1OCc1ccc(Cl)cc1] | 204-206 | (DMSO-d₆) 11.96(1H, brs), 7.83(1H, d, J = 2.0 Hz), 7.75(1H, br), 7.65(1H, dd, J = 2.0, 8.4 Hz), 7.46(1H, br), 7.35-7.44(4H, m), 7.18-7.24(2H, m), 6.95(1H, d, J = 8.4 Hz), 5.17(2H, s), 3.98(3H, s) | — |

TABLE 1-continued

| Example No. | Structure | Melting Point (° C.) | ¹H-NMR (CDCl₃) δ, ppm | Mass (EI) |
|---|---|---|---|---|
| 78 | 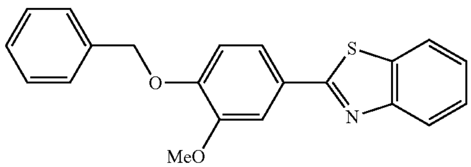 | 108-109 | 8.03(1H, d, J = 8.4 Hz), 7.87(1H, d, J = 7.6 Hz), 7.73(1H, d, J = 2.0 Hz), 7.52(1H, dd, J = 2.0, 8.8 Hz), 7.45-7.48(3H, m), 7.28-7.39(4H, m), 6.95(1H, d, J = 8.8 Hz), 5.24(2H, s), 4.03(3H, s) | m/z 348.0 (MH⁺) |
| 79 | 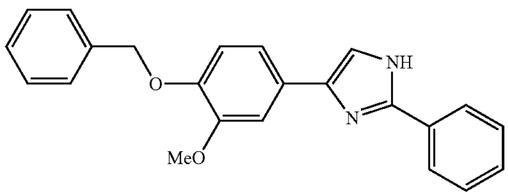 [SMILES: COc1cc(-c2c[nH]c(-c3ccccc3)n2)ccc1OCc1ccccc1] | 190-192 | (DMSO-d₆) 8.30-832 (2H, m), 8.22 (1H, s), 7.73 (1H, bd, J = 1.7 Hz), 7.64-7.66 (3H, m), 7.57 (1H, dd, J = 1.7, 8.3 Hz), 7.34-7.48 (5H, m), 7.19 (1H, d, J = 8.3 Hz), 5.16 (2H, s), 3.91 (3H, s) | — |
| 80 | 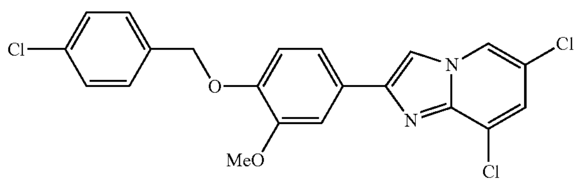 [SMILES: COc1cc(-c2cn3cc(Cl)cc(Cl)c3n2)ccc1OCc1ccc(Cl)cc1] | 162-163 | 8.09 (1H, d, J = 1.8 Hz), 7.80 (1H, s), 7.59 (1H, d, J = 2.1 Hz), 7.32-7.40 (5H, m), 7.25 (1H, d, J = 1.8 Hz), 6.90 (1H, d, J = 8.2 Hz), 5.15 (2H, s), 4.00 (3H, s) | — |
| 81 | 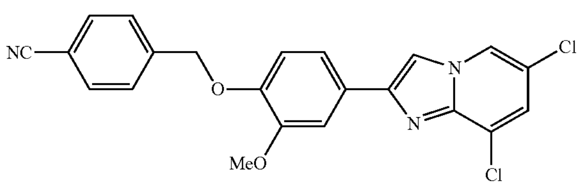 [SMILES: COc1cc(-c2cn3cc(Cl)cc(Cl)c3n2)ccc1OCc1ccc(C#N)cc1] | 187-189 | 8.09 (1H, d, J = 1.5 Hz), 7.81 (1H, s), 7.67 (2H, d, J = 7.9 Hz), 7.61 (1H, d, J = 2.1 Hz), 7.57 (2H, d, J = 7.9 Hz), 7.39 (1H, dd, J = 2.1, 8.2 Hz), 7.25 (1H, d, J = 1.5 Hz), 6.88 (1H, d, J = 8.2 Hz), 5.23 (2H, s), 4.02 (3H, s) | — |
| 82 | 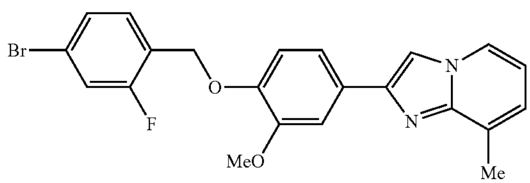 [SMILES: COc1cc(-c2cn3cccc(C)c3n2)ccc1OCc1ccc(Br)cc1F] | 122-124 | 7.97 (1H, d, J = 6.7 Hz), 7.76 (1H, s), 7.61 (1H, d, J = 2.5 Hz), 7.43 (1H, bt, J = 7.6 Hz), 7.40 (1H, dd, J = 2.5, 8.5 Hz), 7.24-7.30 (2H, m), 6.92-6.95 (1H, m), 6.93 (1H, d, J = 8.5 Hz), 6.67 (1H, t, J = 6.7 Hz), 5.19 (2H, s), 4.01 (3H, s), 2.66 (3H, s) | — |
| 83 | 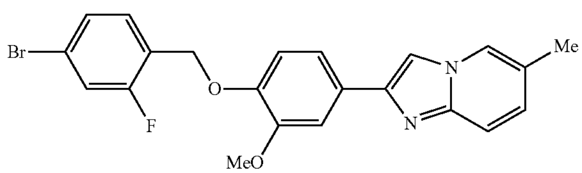 [SMILES: COc1cc(-c2cn3cc(C)ccc3n2)ccc1OCc1ccc(Br)cc1F] | 147-148 | 7.87-7.88 (1H, m), 7.70 (1H, s), 7.59 (1H, d, J = 2.1 Hz), 7.51 (1H, d, J = 9.1 Hz), 7.44 (1H, t, J = 7.9 Hz), 7.36 (1H, dd, J = 2.1, 8.3 Hz), 7.24-7.30 (2H, m), 7.00 (1H, dd, J = 1.7, 9.1 Hz), 6.92 (1H, d, J = 8.3 Hz), 5.19 (2H, s), 3.99 (3H, s), 2.31 (3H, s) | — |
| 84 | 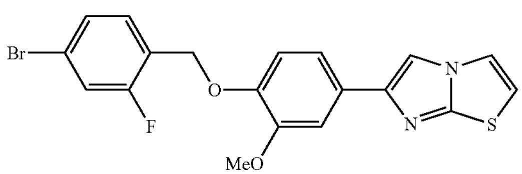 [SMILES: COc1cc(-c2cn3ccsc3n2)ccc1OCc1ccc(Br)cc1F] | 109-111 | 7.67 (1H, s). 7.48 (1H, d, J = 1.8 Hz), 7.43 (1H, d, J = 7.9 Hz), 7.42 (1H, d, J = 4.7 Hz), 7.23-7.31 (3H, m). 6.90 (1H, d, J = 8.5 Hz), 6.81 (1H, d, J = 4.7 Hz), 5.18 (2H, s), 3.97 (3H, s) | — |
| 85 | 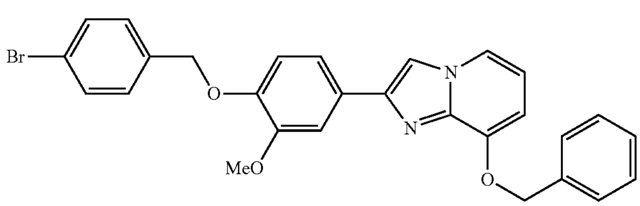 [SMILES: COc1cc(-c2cn3cccc(OCc4ccccc4)c3n2)ccc1OCc1ccc(Br)cc1] | 168-169 | 7.75 (1H, s), 7.72 (1H, bd, J = 7.1 Hz), 7.47-7.52 (4H, m), 7.29-7.40 (6H, m), 6.88 (1H, d, J = 8.3 Hz), 6.58 (1H, bt, J = 7.1 Hz), 6.44 (1H, bd, J = 7.1 Hz), 5.39 (2H, s), 5.12 (2H, s), 3.99 (3H, s) | — |

TABLE 1-continued

| Example No. | Structure | Melting Point (° C.) | ¹H-NMR (CDCl₃) δ, ppm | Mass (EI) |
|---|---|---|---|---|
| 86 | 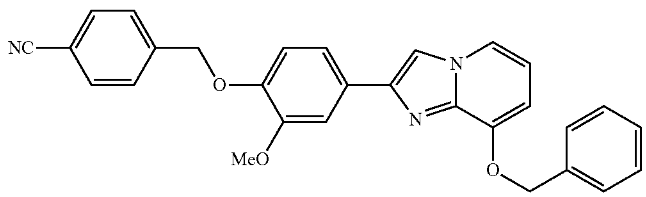 [SMILES: COc1cc(-c2cn3cccc(OCc4ccccc4)c3n2)ccc1OCc1ccc(C#N)cc1] | 169-170 | 7.76 (1H, s), 7.73 (1H, bd, J = 6.6 Hz), 7.65-7.67 (3H, m), 7.50-7.58 (4H, m), 7.30-7.41 (4H, m), 6.86 (1H, d, J = 8.3 Hz), 6.59 (1H, bt, J = 6.6 Hz), 6.44 (1H, bd, J = 6.6 Hz), 5.39 (2H, s), 5.22 (2H, s), 4.01 (3H, s) | — |
| 87 | 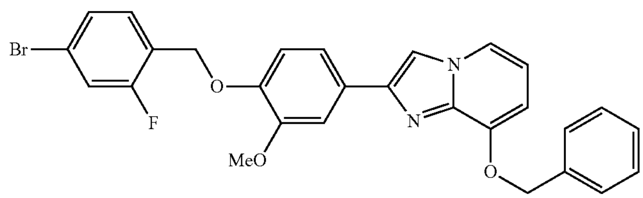 [SMILES: COc1cc(-c2cn3cccc(OCc4ccccc4)c3n2)ccc1OCc1ccc(Br)cc1F] | 108-109 | 7.77 (1H, s), 7.74 (1H, bd, J = 6.6 Hz), 7.51-7.53 (2H, m), 7.25-7.46 (7H, m), 6.92 (1H, d, J = 8.3 Hz), 6.59 (1H, bt, J = 6.6 Hz), 6.45 (1H, bd, J = 6.6 Hz), 5.40 (2H, s), 5.19 (2H, s), 4.00 (3H, s) | — |
| 88 | 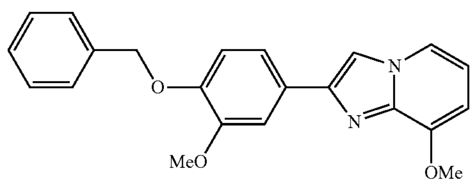 | 189-191 | (DMSO-d₆) 8.75 (1H, bs), 8.42 (1H, dd, J = 2.1, 5.4 Hz), 7.68 (1H, d, J = 2.1 Hz), 7.56 (1H, dd, J = 2.1, 8.3 Hz), 7.35-7.49 (7H, m), 7.22 (1H, d, J = 8.3 Hz), 5.18 (2H, s), 4.12 (3H, s), 3.90 (3H, s) | — |
| 89 | 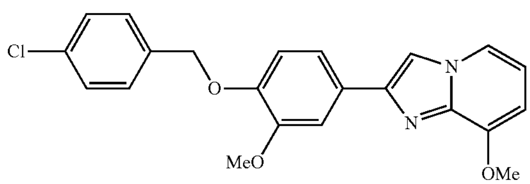 | 132-134 | 7.76 (1H, s), 7.74 (1H, d, J = 6.7 Hz), 7.67 (1H, d, J = 2.0 Hz), 7.37-7.40 (3H, m), 7.32-7.35 (2H, m), 6.88 (1H, d, J = 8.2 Hz), 6.67 (1H, dd, J = 6.7, 7.6 Hz), 6.44 (1H, d, J = 7.6 Hz), 5.14 (2H, s), 4.04 (3H, s), 4.00 (3H, s) | — |
| 90 | 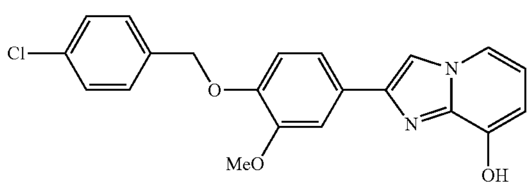 | 220-222 | (DMSO-d₆) 8.28 (1H, s), 7.99 (1H, dd, J = 0.8, 6.6 Hz), 7.59 (1H, d, J = 1.7 Hz), 7.44-7.51 (5H, m), 7.08 (1H, d, J = 8.3 Hz), 6.67 (1H, bt, J = 6.6 Hz), 6.48 (1H, dd, J = 0.8, 6.6 Hz), 5.12 (2H, s), 3.87 (3H, s) | — |
| 91 | 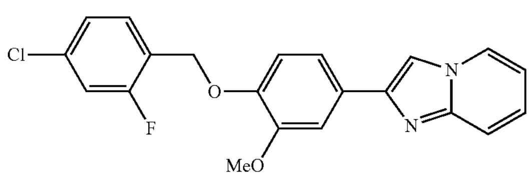 | 119-120 | 8.10 (1H, bd, J = 6.7 Hz), 7.79 (1H, s), 7.60.7.63 (2H, m), 7.50 (1H, bt, J = 7.9 Hz), 7.39 (1H, dd, J = 2.1, 8.2 Hz), 7.09-7.18 (3H, m), 6.94 (1H, d, J = 8.2 Hz), 6.74-6.78 (1H, m), 5.21 (2H, s), 4.00 (3H, s) | — |
| 92 | 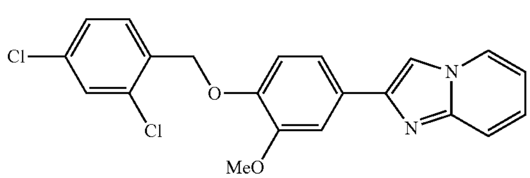 | 138-139 | 8.09 (1H, bd, J = 6.7 Hz), 7.78 (1H, s), 7.60-7.63 (2H, m), 7.55 (1H, d, J = 8.2 Hz), 7.40 (1H, d, J = 2.1 Hz), 7.37 (1H, dd, J = 2.1, 8.2 Hz), 7.26 (1H, dd, J = 2.1, 8.2 Hz), 7.13-7.17 (1H, m), 6.89 (1H, d, J = 8.2 Hz), 6.76 (1H, bt, J = 6.7 Hz), 5.23 (2H, s), 4.02 (3H, s) | — |
| 93 | 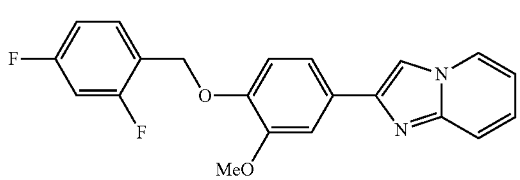 [SMILES: COc1cc(-c2cn3ccccc3n2)ccc1OCc1ccc(F)cc1F] | 137-138 | 8.10 (1H, d, J = 6.7 Hz), 7.80 (1H, s), 7.60-7.63 (2H, m), 7.49-7.56 (1H, m), 7.40 (1H, dd, J = 2.1, 8.5 Hz), 7.13-7.18 (1H, m), 6.96 (1H, d, J = 8.5 Hz), 6.80-6.90 (2H, m), 6.77 (1H, bt, J = 6.7 Hz), 5.19 (2H, s), 4.00 (3H, s) | — |

TABLE 1-continued

| Example No. | Structure | Melting Point (° C.) | ¹H-NMR (CDCl₃) δ, ppm | Mass (EI) |
|---|---|---|---|---|
| 94 | 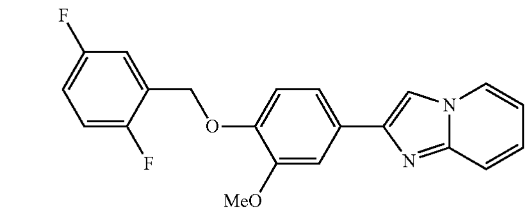 | 115-117 | 8.10 (1H, bd, J = 6.7 Hz), 7.80 (1H, s), 7.62 (1H, bd, J = 9.1 Hz), 7.61 (1H, d, J = 2.1 Hz), 7.40 (1H, dd, J = 2.1, 8.2 Hz), 7.28-7.33 (1H, m), 7.13-7.18 (1H, m), 6.93-7.06 (3H, m), 6.77 (1H, bt, J = 6.7 Hz), 5.23 (2H, s), 4.02 (3H, s) | — |
| 95 | 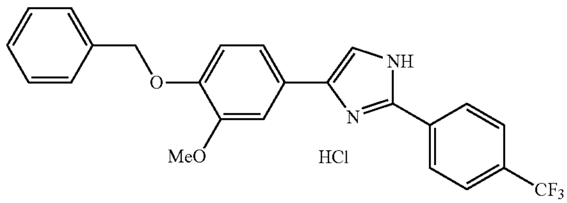 [SMILES: COc1cc(-c2c[nH]c(-c3ccc(C(F)(F)F)cc3)n2)ccc1OCc1ccccc1 ; Cl] | 247-249 | (DMSO-d₆) 8.51 (2H, d, J = 8.3 Hz), 8.26 (1H, s), 8.04 (2H, d, J = 8.3 Hz), 7.73 (1H, d, J = 2.1 Hz), 7.56 (1H, dd, J = 2.1, 8.3 Hz), 7.33-7.49 (5H, m), 7.19 (1H, d, J = 8.3 Hz), 5.17 (2H, s), 3.91 (3H, s) | — |
| 96 | 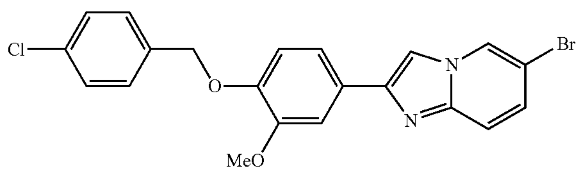 | 178-180 | 8.24-8.25 (1H, m), 7.75 (1H, s), 7.57 (1H, d, J = 2.1 Hz), 7.50 (1H, d, J = 9.5 Hz), 7.32-7.40 (5H, m), 7.21 (1H, dd, J = 2.1, 9.5 Hz), 6.90 (1H, d, J = 8.3 Hz), 5.15 (2H, s), 4.00 (3H, s) | — |
| 97 | 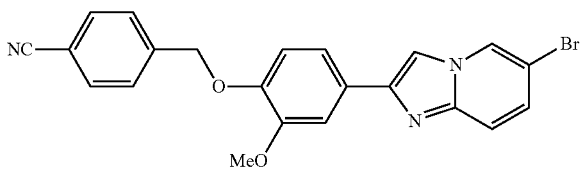 [SMILES: COc1cc(-c2cn3cc(Br)ccc3n2)ccc1OCc1ccc(C#N)cc1] | 165-166 | 8.24-8.25 (1H, m), 7.75 (1H, s), 7.67 (2H, d, J = 8.3 Hz), 7.59 (1H, d, J = 2.1 Hz), 7.57 (2H, d, J = 8.3 Hz), 7.51 (1H, d, J = 9.6 Hz), 7.35 (1H, dd, J = 2.1, 8.3 Hz), 7.22 (1H, dd, J = 2.1, 9.6 Hz), 6.88 (1H, d, J = 8.3 Hz), 5.23 (2H, s), 4.01 (3H, s) | — |
| 98 | 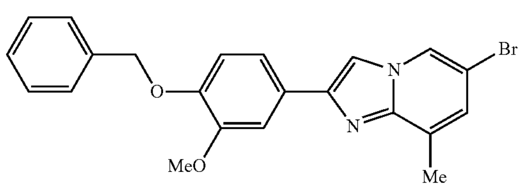 [SMILES: COc1cc(-c2cn3cc(Br)cc(C)c3n2)ccc1OCc1ccccc1] | 164-165 | 8.10 (1H, bs), 7.70 (1H, s), 7.57 (1H, d, J = 2.1 Hz), 7.27-7.46 (6H, m), 7.03 (1H, bs), 6.92 (1H, d, J = 8.3 Hz), 5.20 (2H, s), 4.01 (3H, s), 2.64 (3H, s) | — |
| 99 | 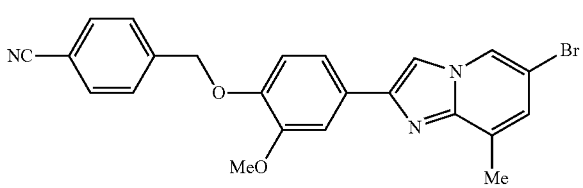 | 177-178 | 8.11 (1H, bs), 7.71 (1H, s), 7.66 (2H, d, J = 8.3 Hz), 7.59 (1H, d, J = 1.7 Hz), 7.56 (2H, d, J = 8.3 Hz), 7.36 (1H, dd, J = 1.7, 8.7 Hz), 7.04 (1H, bs), 6.87 (1H, d, J = 8.7 Hz), 5.23 (2H, s), 4.01 (3H, s), 2.64 (3H, s) | — |
| 100 | 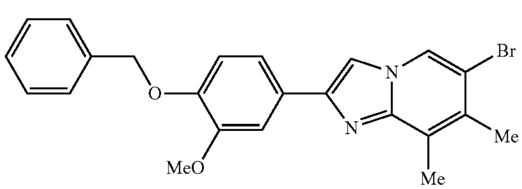 | 158-160 | 8.19 (1H, s), 7.65 (1H, s), 7.58 (1H, d, J = 1.8 Hz), 7.44-7.46 (2H, m), 7.27-7.38 (4H, m), 6.92 (1H, d, J = 8.2 Hz), 5.20 (2H, s), 4.01 (3H, s), 2.68 (3H, s), 2.42 (3H, s) | — |
| 101 | 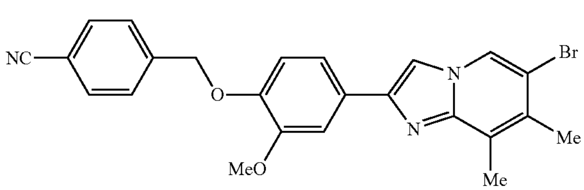 [SMILES: COc1cc(-c2cn3cc(Br)c(C)c(C)c3n2)ccc1OCc1ccc(C#N)cc1] | 180-181 | 8.19 (1H, s), 7.66 (1H, s), 7.65 (2H, d, J = 8.3 Hz), 7.60 (1H, d, J = 2.1 Hz), 7.56 (2H, d, J = 8.3 Hz), 7.36 (1H, dd, J = 2.1, 8.3 Hz), 6.86 (1H, d, J = 8.3 Hz), 5.23 (2H, s), 4.01 (3H, s), 2.68 (3H, s), 2.42 (3H, s) | — |

TABLE 1-continued

| Example No. | Structure | Melting Point (°C.) | ¹H-NMR (CDCl₃) δ, ppm | Mass (EI) |
|---|---|---|---|---|
| 102 | t-Bu-phenyl-CH₂-O-(3-MeO-phenyl)-imidazo[1,2-a]pyridine | — | 8.08 (br d, J = 6.6 Hz, 1H), 7.77 (br s, 1H), 7.63-7.59 (overlap of 2H), 7.40-7.36 (overlap of 5H), 7.17-7.12 (m, 1H), 6.96 (d, J = 8.2 Hz, 1H), 6.75 (br t, J = 6.7 Hz, 1H), 5.16 (s, 2H), 4.00 (s, 3H), 1.31 (s, 9H) | m/z 387.3 (MH⁺) |
| 103 | 2-phenyl-benzofuran-5-yl-imidazo[1,2-a]pyridine | 239.5-241 | 6.79 (ddd, 1H, J = 1.1, 6.7, 6.7 Hz), 7.1 (d, 1H, 0.5 Hz,), 7.15-7.21 (m, 1H), 7.34-7.39 (m, 1H) 7.44-7.49 (overlap of 2H), 7.57 (d, 1H, J = 8.5 Hz), 7.65 (d, 1H, J = 8.5 Hz), 7.87-7.91 (overlap of 4H), 8.14 (d, 1H, J = 6.9 Hz), 8.22 (d, 1H, J = 1.4 Hz) | m/z 311.3 (MH⁺) |
| 104 | 2,6-difluorobenzyl-O-(3-MeO-phenyl)-imidazo[1,2-a]pyridine | 136-137 | 8.25 (s, 1H), 7.79 (s, 1H), 7.60 (s, 1H), 7.55 (d, 1H), 7.40 (d, 1H), 7.25 (d, 1H), 7.19 (d, 1H), 7.15 (d, 2H), 6.82 (d, 2H), 6.5 (s, 1H), 5.20 (s, 2H), 3.92 (s, 3H) | m/z 367 (MH⁺) |
| 105 | (R)-1-phenylethyl-O-(3-OMe-phenyl)-imidazo[1,2-a]pyridine | — | (CD₃OD) 8.38 (d, 1H), 7.62-7.54 (m, 2H), 7.47-7.22 (overlap of 6H), 7.14 (s, 1H), 6.98-6.89 (m, 3H), 5.50 (q, 1H), 3.96 (s, 3H), 1.70 (d, 3H) | m/z 345.2 (MH⁺) |
| 106 | phenyl-O-(3-OMe-phenyl)-imidazo[1,2-a]pyridine | — | 8.55 (d, J = 7.1 Hz, 1H), 7.72 (br s, 1H), 7.62 (d, J = 9.1 Hz, 1H), 7.40-7.29 (overlap of 4H), 7.23-7.20 (dd, J = 8.2, 1.9 Hz, 1H), 7.16-7.13 (d, J = 8.2 Hz, 1H), 7.08-6.92 (overlap of 4H), 3.86 (s, 3H) | m/z 317.3 (MH⁺) |
| 107 | F₃CO-phenyl-CH₂-O-(3-OMe-phenyl)-imidazo[1,2-a]pyridine | — | (CD₃OD) 8.48 (br d, 1H), 7.70-7.55 (overlap of 4H), 7.40-7.28 (overlap of 3H), 7.24-7.08 (overlap of 3H), 6.98 (br t, 1H), 5.21 (s, 2H), 3.92 (s, 3H) | m/z 415.2 (MH⁺) |
| 108 | NC-phenyl-CH₂-O-(3-OMe-phenyl)-imidazo[1,2-a]pyridine | 148-149 | 8.28(1H, d, J = 6.8 Hz), 7.70(2H, d, J = 7.6 Hz), 7.67(1H, d, J = 8.0 Hz), 7.65(1H, s), 7.60(2H, d, J = 7.6 Hz), 7.19(1H, dd, J = 7.6, 8.0 Hz), 7.07(1H, s), 7.06(1H, d, J = 8.0 Hz), 6.97(1H, d, J = 8.0 Hz), 6.80(1H, dd, J = 6.8, 7.6 Hz) | — |

TABLE 1-continued

| Example No. | Structure | Melting Point (° C.) | ¹H-NMR (CDCl₃) δ, ppm | Mass (EI) |
|---|---|---|---|---|
| 109 | 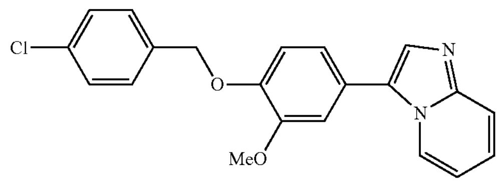 [SMILES: COc1cc(-c2cnc3ccccn23)ccc1OCc1ccc(Cl)cc1] | — | 8.30 (d, 1H), 7.70-7.62 (m, 1H), 7.50-7.32 (overlap of 4H), 7.25-7.15 (m, 1H), 7.12-6.96 (overlap of 4H), 6.80 (br t, 1H), 5.20 (s, 2H), 3.98 (s, 3H) | m/z 365.2 (MH⁺) |
| 110 | 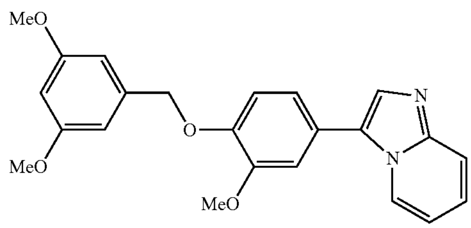 [SMILES: COc1cc(COc2ccc(-c3cnc4ccccn34)cc2OC)cc(OC)c1] | — | (CD₃OD) 8.48 (br d, 1H), 7.67-7.56 (overlap of 2H), 7.40-7.32 (m, 1H), 7.23-7.10 (overlap of 3H), 6.98 (br t, 1H), 6.68 (d, 2H), 6.45 (t, 1H), 5.17 (s, 2H), 3.95 (s, 3H), 3.80 (s, 6H) | m/z 391.3 (MH⁺) |
| 111 | 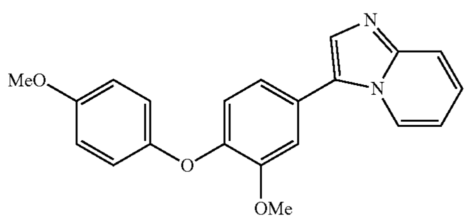 [SMILES: COc1ccc(Oc2ccc(-c3cnc4ccccn34)cc2OC)cc1] | — | 8.32 (br d, J = 6.9 Hz, 1H), 7.70-7.67 (overlap of 2H), 7.26-7.21 (m, 1H), 7.13 (d, J = 1.9 Hz, 1H), 7.08-7.01 (overlap of 3H), 6.96-6.89 (overlap of 3H), 6.83 (br t, J = 6.9 Hz, 1H), 3.94 (s, 3H), 3.82 (s, 3H) | m/z 347.3 (MH⁺) |
| 112 | 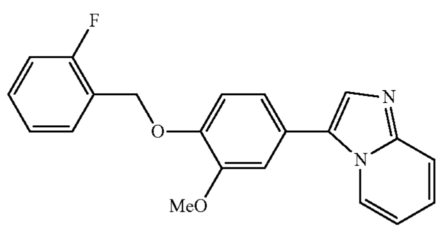 [SMILES: COc1cc(-c2cnc3ccccn23)ccc1OCc1ccccc1F] | — | (CD₃OD) 8.50 (d, 1H), 7.70-7.55 (overlap of 3H), 7.44-7.30 (overlap of 2H), 7.27-7.08 (overlap of 5H), 6.97 (t, 1H), 5.22 (s, 2H), 3.92 (s, 3H) | m/z 349.2 (MH⁺) |
| 113 | 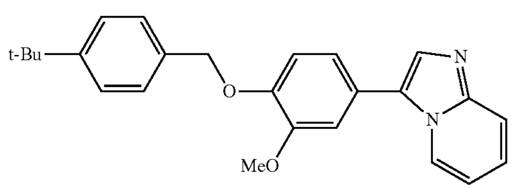 [SMILES: COc1cc(-c2cnc3ccccn23)ccc1OCc1ccc(C(C)(C)C)cc1] | — | (CD₃OD) 8.48 (br d, 1H), 7.70-7.55 (overlap of 2H), 7.50-7.32 (overlap of 5H), 7.22-7.08 (overlap of 3H), 6.99 (br t, 1H), 5.19 (s, 2H), 3.92 (s, 3H), 1.37 (s, 9H) | m/z 387.3 (MH⁺) |
| 114 | 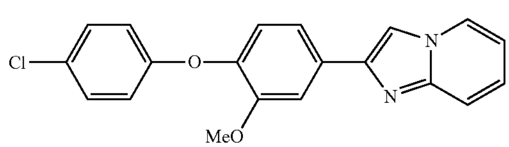 [SMILES: COc1cc(-c2cn3ccccc3n2)ccc1Oc1ccc(Cl)cc1] | 148-149 | 3.88 (s, 3H), 6.83-6.91 (m, 1H), 6.90 (d, 1H, J = 9.0 Hz), 6.99 (d, 1H, J = 8.3 Hz), 7.21-7.32 (overlap of 4H), 7.38 (dd, 1H, J = 1.2, 8.2 Hz), 7.64 (d, 1H, J = 1.9 Hz), 7.69 (d, 1H, J = 9.3 Hz), 7.82 (d, 1H, J = 0.5 Hz), 8.13 (ddd, 1H, J = 1.1, 1.2, 6.8 Hz) | m/z 351.3 (MH⁺) |
| 115 | 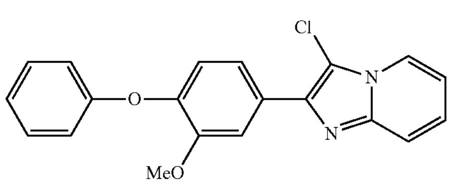 [SMILES: COc1cc(-c2nc3ccccn3c2Cl)ccc1Oc1ccccc1] | 108-109 | 8.09 (d, 1H), 7.89 (d, 1H), 7.70 (d, 1H), 7.57 (d, 1H), 7.35 (d, 1H), 7.29 (d, 1H), 715-6.82 (m, 5H), 3.92 (s, 3H) | m/z 351 (MH⁺) |

TABLE 1-continued

| Example No. | Structure | Melting Point (° C.) | ¹H-NMR (CDCl₃) δ, ppm | Mass (EI) |
|---|---|---|---|---|
| 116 | 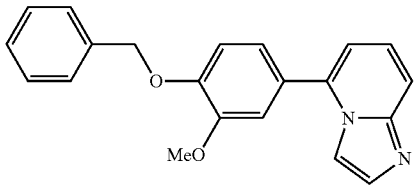 [SMILES: COc1cc(-c2cccc3nccn23)ccc1OCc1ccccc1] | 164-166 | 7.70-7.59 (m, 3H), 7.50 (d, 2H), 7.45-7.34 (m, 3H), 7.26 (dd, 1H), 7.15 (m, 2H), 7.04 (d, 1H), 6.73 (d, 1H), 5.25 (s, 2H), 3.98 (s, 3H) | m/z 331 (MH+) |
| 117 | 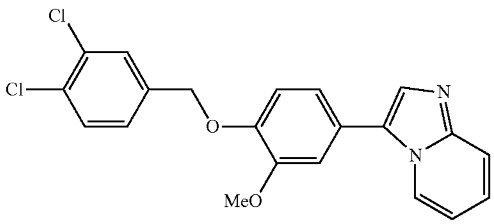 [SMILES: COc1cc(-c2cnc3ccccn23)ccc1OCc1ccc(Cl)c(Cl)c1] | — | 8.28 (dt, 1H), 7.71-7.63 (m, 2H), 7.61-7.54 (m, 1H), 7.50-7.42 (d, 1H), 7.34-7.27 (m, 1H), 7.22-7.14 (m, 1H), 7.10-7.00 (overlap of 2H), 6.99-6.92 (m, 1H), 6.84-6.75 (br t, 1H), 5.20 (s, 2H), 3.98 (s, 3H) | m/z 399.1 (MH⁺) |
| 118 | 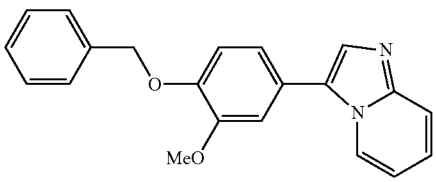 [SMILES: COc1cc(-c2cnc3ccccn23)ccc1OCc1ccccc1] | — | (CD₃OD) 8.29 (d, 1H), 7.65 (m, 2H), 7.50-7.28 (m, 5H), 7.20 (t, 1H), 7.01 (m, 3H), 6.80 (m, 1H), 5.21 (s, 2H), 3.92 (s, 3H) | m/z 331 (MH⁺). |
| 119 | 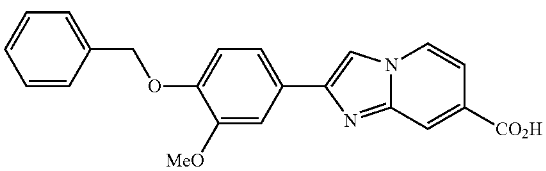 [SMILES: COc1cc(-c2cn3ccc(C(=O)O)cc3n2)ccc1OCc1ccccc1] | — | (DMSO-d₆) 13.40(br, 1H), 9.22(s, 1H), 8.50(s, 1H), 7.709dd, 2H), 7.60 (d, 1H), 7.30-7.55(m, 6H), 7.16(d, 1H), 5.15(s, 1H), 3.88(s, 3H) | m/z 375 (MH⁺). |
| 120 | 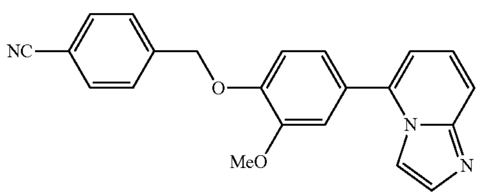 [SMILES: COc1cc(-c2cccc3nccn23)ccc1OCc1ccc(C#N)cc1] | 155-157 | 7.72-7.59 (overlap of 7H), 7.27-7.12 (overlap of 3H), 6.98 (d, J = 8.1 Hz, 1H), 6.72 (dd, J = 6.9, 1.0 Hz, 1H), 5.28 (s, 2H), 3.94 (s, 3H) | m/z 356.1 (MH⁺) |
| 121 | 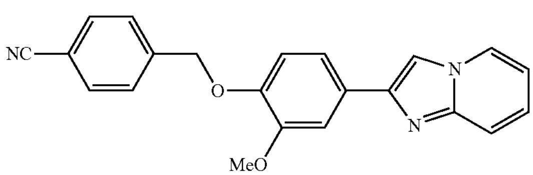 [SMILES: COc1cc(-c2cn3ccccc3n2)ccc1OCc1ccc(C#N)cc1] | — | 8.22 (dd, J = 6.9, 1.1 Hz, 1H), 7.86-7.81 (overlap of 3H), 7.61-7.53 (overlap of 4H), 7.39-7.33 (m, 1H), 7.08 (d, J = 8.2 Hz, 1H), 6.99-6.95 (overlap of 2H), 3.77 (s, 3H) | m/z 342.4 (MH⁺) |
| 122 | 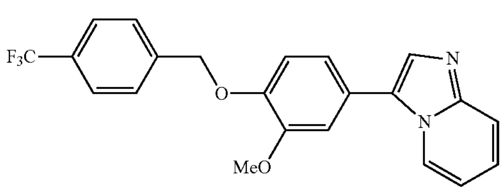 [SMILES: COc1cc(-c2cnc3ccccn23)ccc1OCc1ccc(C(F)(F)F)cc1] | 133-135 | 8.30 (d, 1H), 7.80-7.60 (overlap of 6H), 7.20 (t, 1H), 7.15-6.90 (overlap of 3H), 6.80 (t, 1H), 5.30 (s, 2H), 3.95 (s, 3H) | m/z 399 (MH⁺) |
| 123 | 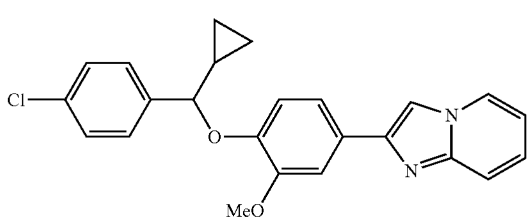 [SMILES: COc1cc(-c2cn3ccccc3n2)ccc1OC(c1ccc(Cl)cc1)C1CC1] | — | 8.08 (dt, J = 7.7, 1.1 Hz, 1H), 7.74 (br s, 1H), 7.62-7.56 (overlap of 2H), 7.39-7.26 (overlap of 4H), 7.22 (dd, J = 8.4, 1.8 Hz, 1H), 7.18-7.12 (m, 1H), 6.78-6.70 (overlap of 2H), 4.55 (d, J = 8.0 Hz, 1H), 4.00 (s, 3H), 1.46-1.38 (m, 1H), 0.74-0.67 (m, 1H), 0.62-0.51 (overlap of 2H), 0.44-0.38 (m, 1H) | m/z 405.2 (MH⁺) |

TABLE 1-continued

| Example No. | Structure | Melting Point (° C.) | 1H-NMR (CDCl3) δ, ppm | Mass (EI) |
|---|---|---|---|---|
| 124 | 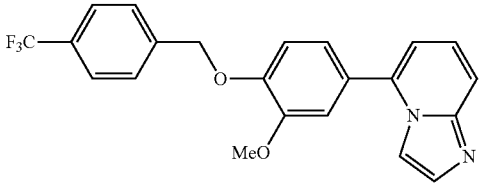 [SMILES: COc1cc(-c2cccc3nccn23)ccc1OCc1ccc(C(F)(F)F)cc1] | — | 7.74-7.60 (m, 7H), 7.26 (m, 1H), 7.16 (m, 2H), 7.00 (d, 1H), 6.74 (d, 1H), 5.31 (s, 2H), 3.98 (s, 3H) | m/z 399 (MH+) |
| 125 | 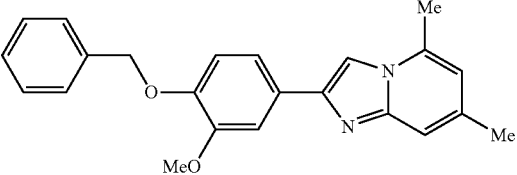 [SMILES: COc1cc(-c2cn3c(C)cc(C)cc3n2)ccc1OCc1ccccc1] | — | 7.64 (d, 2H), 7.25-7.55(m, 7H), 6.95(d, 1H), 6.47(s, 1H), 5.20(s, 2H), 4.00(s, 3H), 2.58(s, 3H), 2.48(s, 3H) | m/z 359 (MH+) |
| 126 | 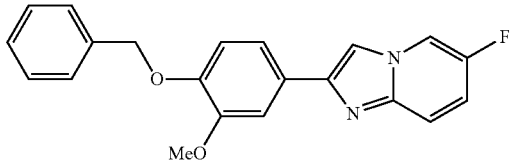 [SMILES: COc1cc(-c2cn3cc(F)ccc3n2)ccc1OCc1ccccc1] | — | 8.04-8.03 (m, 1H), 7.78 (s, 1H), 7.61-7.52 (overlap of 2H), 7.48-7.42 (overlap of 2H), 7.41-7.26 (overlap of 4H), 7.11-7.04 (m, 1H), 6.93 (d, J = 8.5 Hz, 1H), 5.20 (s, 2H), 4.00 (s, 3H) | m/z 349.1 (MH+) |
| 127 | 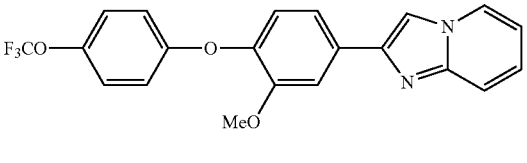 [SMILES: COc1cc(-c2cn3ccccc3n2)ccc1Oc1ccc(OC(F)(F)F)cc1] | — | 8.14 (br d, J = 6.9 Hz, 1H), 7.83 (br s, 1H), 7.72-7.65 (overlap of 2H), 7.39 (dd, J = 8.3, 1.9 Hz, 1H), 7.27-7.21 (m, 1H), 7.17-7.14 (overlap of 2H), 7.02 (d, J = 8.2 Hz, 1H), 6.99-6.95 (overlap of 2H), 6.86 (ddd, J = 6.8, 6.7, 1.1 Hz, 1H), 3.88 (s, 3H) | m/z 401.3 (MH+) |
| 128 | 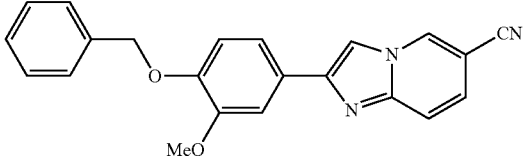 [SMILES: COc1cc(-c2cn3cc(C#N)ccc3n2)ccc1OCc1ccccc1] | — | 8.55 (s, 1H), 7.86(s, 1H), 7.70(d, 1H), 7.60(d, 1H), 7.7.25-7.55(m, 7H), 6.96(d, 2H), 5.20(s, 2H), 4.00(s, 3H) | m/z 356 (MH+) |
| 129 | 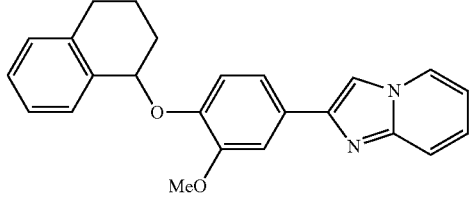 [SMILES: COc1cc(-c2cn3ccccc3n2)ccc1OC1CCCc2ccccc21] | — | 8.03 (br d, J = 6.9 Hz, 1H), 7.61-7.57 (overlap of 2H), 7.50 (d, J = 1.9 Hz, 1H), 7.16-7.00 (overlap of 5H), 6.95-6.92 (overlap of 2H), 6.72 (ddd, J = 6.8, 6.7, 1.1 Hz, 1H), 4.57 (t, J = 7.0 Hz, 1H), 4.03 (s, 3H), 2.96-2.87 (m, 2H), 2.15-2.05 (m, 1H), 2.02-1.92 (m, 2H), 1.85-1.80 (m, 1H) | m/z 371.3 (MH+) |
| 130 | 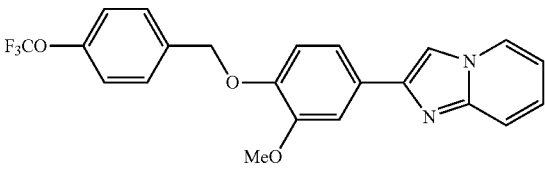 [SMILES: COc1cc(-c2cn3ccccc3n2)ccc1OCc1ccc(OC(F)(F)F)cc1] | — | 8.09 (dt, J = 8.0, 1.1 Hz, 1H), 7.79 (d, J = 0.6 Hz, 1H), 7.64-7.61 (overlap of 2H), 7.50 (br d, J = 8.8 Hz, 2H), 7.39 (dd, J = 8.4, 1.9 Hz, 1H), 7.26-7.13 (overlap of 3H), 6.92 (d, J = 8.3 Hz, 1H), 6.76 (ddd, J = 6.8, 6.7, 1.1 Hz, 1H), 5.17 (s, 2H), 4.00 (s, 3H) | m/z 415.1 (MH+) |

TABLE 1-continued

| Example No. | Structure | Melting Point (° C.) | ¹H-NMR (CDCl₃) δ, ppm | Mass (EI) |
|---|---|---|---|---|
| 131 | 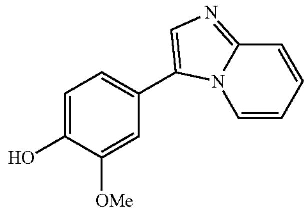 [SMILES: COc1cc(-c2cnc3ccccn23)ccc1O] | — | (CD3OD) 8.42 (d, 1H), 7.60 (m, 2H), 7.35 (t, 1H) 7.17-6.90 (m, 4H), 3.92 (s, 3H) | m/z 241 (M + 1). |
| 132 | 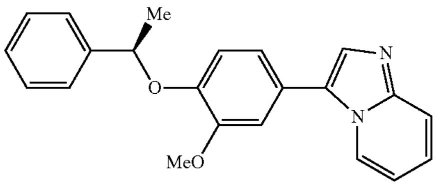 [SMILES: COc1cc(-c2cnc3ccccn23)ccc1O[C@H](C)c1ccccc1] | — | (CD₃OD) 8.55 (app d, 1H), 7.78-7.70 (m, 2H), 7.64-7.35 (overlap of 6H), 7.31 (s, 1H), 7.19-7.13 (m, 3H), 5.62 (q, 1H), 4.05 (s, 3H), 1.81 (d, 3H) | m/z 345.3 (MH⁺) |
| 133 | 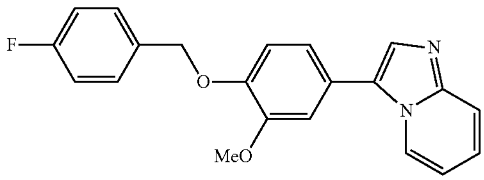 [SMILES: COc1cc(-c2cnc3ccccn23)ccc1OCc1ccc(F)cc1] | 118-119 | 8.25 (s, 1H), 7.70 (d, 1H), 7.57 (d, 1H), 7.35 (d, 1H), 7.29 (d, 1H), 7.15 (d, 2H), 6.82 (d, 2H), 5.20 (s, 2H), 3.92 (s, 3H) | m/z 349 (MH⁺) |
| 134 | 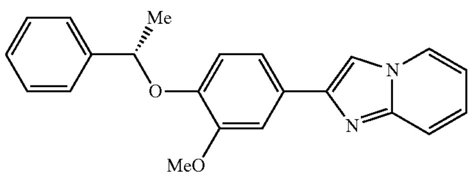 [SMILES: COc1cc(-c2cn3ccccc3n2)ccc1O[C@@H](C)c1ccccc1] | 149-150 | 8.07 (app d, J = 7.7 Hz, 1H), 7.73 (s, 1H), 7.62-7.57 (m, 2H), 7.41 (app d, J = 7.7 Hz, 2H), 7.33 (br t, J = 7.4 Hz, 2H), 7.27-7.22 (m, 2H), 7.17-7.12 (m, 1H), 6.77-6.73 (m, 2H), 5.36 (q, J = 6.4 Hz, 1H), 4.01 (s, 3H), 1.71 (d, J = 6.3 Hz, 3H) | m/z 345.2 (MH⁺) |
| 135 | 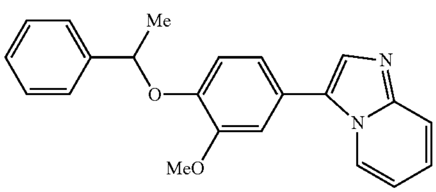 [SMILES: COc1cc(-c2cnc3ccccn23)ccc1OC(C)c1ccccc1] | 113-113.5 | 8.24 (dt, J = 8.9, 1.1 Hz, 1H), 7.64 (dt, J = 9.0, 1.1 Hz, 1H), 7.60 (s, 1H), 7.45-7.26 (overlap of 5H), 7.19-7.13 (m, 1H), 7.02 (d, J = 1.9 Hz, 1H), 6.93 (dd, J = 8.2, 1.9 Hz, 1H), 6.84 (d, J = 8.5 Hz, 1H), 6.77 (ddd, J = 6.9, 6.8, 1.1 Hz, 1H), 5.38 (q, J = 6.6 Hz, 1H), 3.94 (s, 3H), 1.74 (d, J = 6.4 Hz, 3H) | m/z 345.1 (MH⁺) |
| 136 | 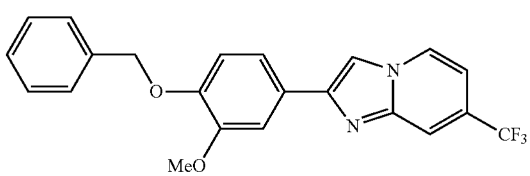 [SMILES: COc1cc(-c2cn3ccc(C(F)(F)F)cc3n2)ccc1OCc1ccccc1] | — | 8.90 (d, 1H), 8.73 (s, 1H), 8.15 (s, 1H), 7.63(s, 1H), 7.30-7.60(m, 7H), 7.20(d, 1H), 5.18(s, 2H), 3.88(s, 3H) | m/z 399 (MH+) |
| 137 | 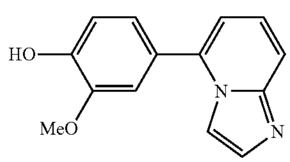 [SMILES: COc1cc(-c2cccc3nccn23)ccc1O] | 177-178 | (CD₃OD) 7.82 (s, 1H), 7.59-7.51 (m, 2H), 7.41 (m, 1H), 7.22 (d, 1H), 7.14 (dd, 1H), 6.95 (d, 1H), 6.88 (dd, 1H), 3.98 (s, 3H) | m/z 241 (M + 1) |
| 138 | 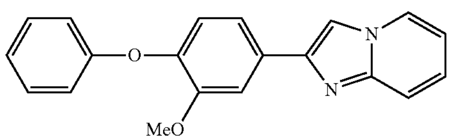 [SMILES: COc1cc(-c2cn3ccccc3n2)ccc1Oc1ccccc1] | 95-97 | 8.12 (dt, J = 7.9, 1.1 Hz, 1H), 7.84 (br s, 1H), 7.72 (d, J = 1.9 Hz, 1H), 7.66-7.63 (m, 1H), 7.44-7.42 (m, 1H), 7.34-7.26 (overlap of 2H), 7.21-18 (m, 1H), 7.16-6.98 (overlap of 3H), 6.78 (ddd, J = 6.7, 6.6, 1.1 Hz, 1H), 3.96 (s, 3H) | m/z 317.3 (MH⁺) |

TABLE 1-continued

| Example No. | Structure | Melting Point (° C.) | ¹H-NMR (CDCl₃) δ, ppm | Mass (EI) |
|---|---|---|---|---|
| 139 | 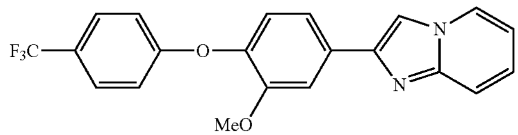 [SMILES: COc1cc(-c2cn3ccccc3n2)ccc1Oc1ccc(C(F)(F)F)cc1] | — | 8.13 (dt, J = 8.0, 1.1 Hz, 1H), 7.84 (br s, 1H), 7.66 (d, J = 1.9 Hz, 1H), 7.56-7.48 (overlap of 3H), 7.42 (dd, J = 8.3, 1.9 Hz, 1H), 7.27-7.20 (m, 1H), 7.07 (d, J = 8.3 Hz, 1H), 7.01-6.95 (overlap of 2H), 6.85 (ddd, J = 6.8, 6.7, 1.1 Hz, 1H), 3.85 (s, 3H) | m/z 385.3 (MH⁺) |
| 140 | 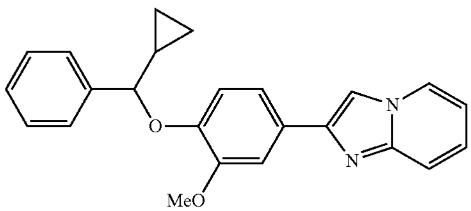 [SMILES: COc1cc(-c2cn3ccccc3n2)ccc1OC(c1ccccc1)C1CC1] | — | 8.07 (dd, J = 6.7, 1.1 Hz, 1H), 7.73 (br s, 1H), 7.61-7.56 (overlap of 2H), 7.45-7.42 (overlap of 2H), 7.36-7.11 (overlap of 5H), 6.77-6.72 (overlap of 2H), 4.57 (d, J = 8.0 Hz, 1H), 4.00 (s, 3H), 1.51-1.43 (m, 1H), 0.74-0.67 (m, 1H), 0.62-0.52 (overlap of 2H), 0.47-0.40 (m, 1H) | m/z 371.2 (MH⁺) |
| 141 | 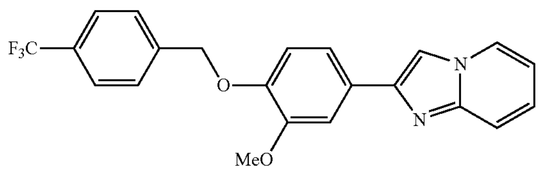 [SMILES: COc1cc(-c2cn3ccccc3n2)ccc1OCc1ccc(C(F)(F)F)cc1] | — | 8.25 (d, 1H), 7.95 (s, 1H), 7.90-7.70 (m, 6H), 7.55 (d, 1H), 7.35 (dd, 1H), 7.10 (d, 1H), 6.90 (t, 1H), 5.40 (s, 2H), 4.20 (s, 3H) | m/z 399 (MH⁺). |
| 142 | 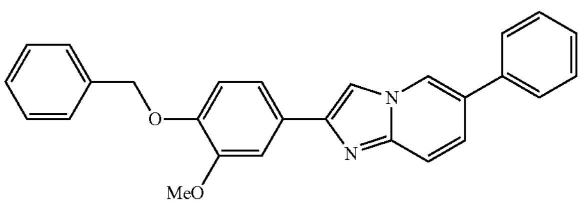 [SMILES: COc1cc(-c2cn3cc(-c4ccccc4)ccc3n2)ccc1OCc1ccccc1] | — | 9.20 (s, 1H), 8.66(s, 1H), 8.25(dd, 1H), 8.05(d, 1H), 7.81(d, 2H), 7.32-7.64(m, 10H), 7.28(d, 1H), 5.20(s, 2H), 3.94(s, 3H) | m/z 407 (MH⁺). |
| 143 | 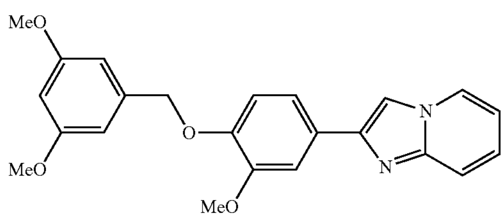 [SMILES: COc1cc(COc2ccc(-c3cn4ccccc4n3)cc2OC)cc(OC)c1] | — | 8.10 (dt, J = 8.0, 1.1 Hz, 1H), 7.77 (br s, 1H), 7.63-7.60 (overlap of 2H), 7.35(dd, J = 8.4, 2.1 Hz, 1H), 7.18-7.12 (m, 1H), 6.93 (d, J = 8.5 Hz, 1H), 6.76 (ddd, J = 6.8, 6.7, 1.1 Hz, 1H), 6.62 (d, J = 2.2 Hz, 2H), 6.39 (t, J = 2.2 Hz, 1H), 5.15 (s, 2H), 4.01 (s, 3H), 3.79 (s, 6H) | m/z 391.2 (MH⁺) |
| 144 | 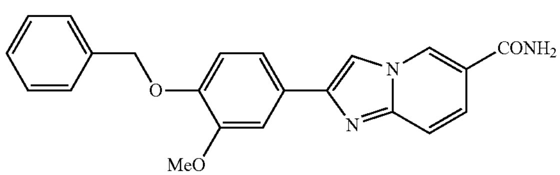 [SMILES: COc1cc(-c2cn3cc(C(N)=O)ccc3n2)ccc1OCc1ccccc1] | — | 9.20 (s, 1H), 8.66(s, 1H), 8.25(dd, 1H), 8.05(d, 1H), 7.81(d, 2H), 7.32-7.64(m, 10H), 7.28(d, 1H), 5.20(s, 2H), 3.94(s, 3H) | m/z 407 (MH⁺). |
| 145 | 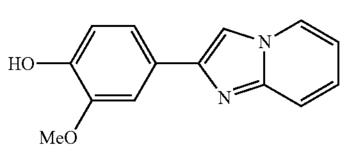 [SMILES: COc1cc(-c2cn3ccccc3n2)ccc1O] | — | 8.30 (d, 1H), 7.95 (s, 1H), 7.80-7.70 (m, 2H), 7.50-7.30 (m, 3H), 7.10 (d, 1H), 6.95 (t, 1H), 4.15 (s, 3H) | m/z 241 (MH⁺) |
| 146 | 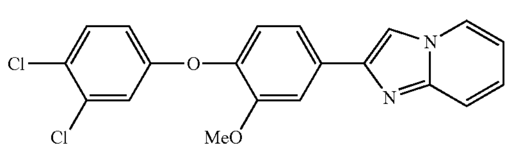 [SMILES: COc1cc(-c2cn3ccccc3n2)ccc1Oc1ccc(Cl)c(Cl)c1] | — | 8.14 (br d, J = 6.9 Hz, 1H), 7.87 (br s, 1H), 7.73 (d, J = 1.9 Hz, 1H), 7.65 (br d, J = 9.3 Hz, 1H), 7.45 (dd, J = 8.2, 1.9 Hz, 1H), 7.34 (d, J = 9.1 Hz, 1H), 7.23-7.17 (m, 1H), 7.08-7.03 (overlap of 2H), 6.85-6.79 (overlap of 2H), 3.94 (s, 3H) | m/z 385.2 (M⁺) |

TABLE 1-continued

| Example No. | Structure | Melting Point (°C.) | $^1$H-NMR (CDCl$_3$) δ, ppm | Mass (EI) |
|---|---|---|---|---|
| 147 | (structure) | — | 8.16 (br d, J = 6.6 Hz, 1H), 7.90 (br s, 1H), 7.77 (d, J = 1.9 Hz, 1H), 7.65 (dd, J = 8.5, 0.6 Hz, 1H), 7.53-7.49 (overlap of 2H), 7.33 (br s, 2H), 7.25-7.19 (m, 1H), 7.14 (d, J = 8.2 Hz, 1H), 6.83 (ddd, J = 6.8, 6.7, 1.1 Hz, 1H), 3.91 (s, 3H) | m/z 453.2 (MH$^+$) |
| 148 | (structure) | — | 8.07 (d, J = 6.9 Hz, 1H), 7.74 (s, 1H), 7.61-7.57 (m, 2H), 7.37-7.23 (overlap of 5H), 7.14 (ddd, J = 8.0, 6.6, 1.4 Hz, 1H), 6.77-6.73 (m, 2H), 5.33 (q, J = 6.6 Hz, 1H), 4.00 (s, 3H), 1.68 (d, J = 6.6 Hz, 3H) | m/z 379.1 (MH$^+$) |
| 149 | (structure) HCl | 276-278 | — | — |

Pharmacological Test 1

Test for Increase in LPL mRNA Expression

A luciferase assay was employed to simply and quickly detect an increase in human LPL mRNA. The principle of the assay is as follows:

Luciferase emits light when reacted with luciferine (substrate). The expression of LPL mRNA is controlled by 5'-UTR and 3'-UTR (promoter regions) of the LPL gene. By introducing the promoter regions of the LPL gene into a commercially available plasmid (for example, that produced by Clonetics Corp.) to produce a plasmid (reporter plasmid) that stably expresses luciferase in human cells, such a plasmid expresses luciferase only under conditions in which LPL mRNA can increase. Therefore, when the substrate is introduced to the expression system and the amount of luciferase expression (luciferase activity) is quantified as the extent of chemiluminescence, the amount of LPL mRNA expression can be estimated.

The test herein was performed as follows: Using a plasmid for the luciferase assay manufactured by Clontech, wherein human LPL 5'-UTR (Enerback, S., et al., *Mol. Cell. Biol.* 12 (10) (1992): 4622-4633) and 3'-UTR (Wion, K. L., et al., *Science* 235 (1987): 4796, 1638-1641) had been inserted, human-derived liposarcoma cell line SW872 (ATCC Accession No. HTB-92) was transformed to prepare an HTB-92/p387/p383 cell line, which stably expresses luciferase.

This HTB-92/p387/p383 cell line was introduced into a 225 cm$^2$ culture flask furnished with a culture medium and cultured at 37° C. in the absence of CO$_2$ until reaching confluence. Leibovitz's L-15 culture medium (containing 10% FBS, 1% GlutaMaxII, 10 μg/ml streptomycin, 1 μg/ml puromycin, 250 μg/ml hygromycin B) was used as the culture medium. After reaching confluence, the cells were collected, plated on 384-well plates to have 20000 cells/well, and cultured with 50 μl/well of the culture medium under the same conditions as above (37° C., absence of CO$_2$). After 3 days of culturing, the culture medium was replaced by 50 μl/well phenol-red-free DMEM (containing 10% FBS, 1% GlutaMax, 10 U/ml penicillin, 10 μg/ml streptomycin, 1 μg/ml puromycin, 250 μg/ml hygromycin, 1 μM dexamethasone, 0.5 μM IBMX; differentiation medium), and the cells were cultured for 5 more days at 37° C. in the presence of CO$_2$ to differentiate.

Furthermore, the culture medium was replaced by a 50 μl/well medium containing a compound of the invention (compound prepared in an Example) as a test substance wherein the compound had been conditioned with DMSO to a specific concentration selected from $10^{-4}$ M to $3\times10^{-10}$ M. The cells were cultured for 5 days at 37° C. in the presence of CO$_2$.

After 5 days of culturing, a luciferase substrate solution (manufactured by Promega Corporation) was introduced to each well in an amount of 30 μl/well. The cells were left to stand 10 minutes at room temperature, and luciferase activities were measured by a luminometer (a microplate scintilltion counter; The Wallac MicroBeta Trilux, manufactured by Perkin Elmer, Inc.).

Cells that had been cultured and differentiated in a differentiation medium prepared by adding 0.1% DMSO to the above-mentioned DMEM medium (differentiation medium) not containing phenol red were used as a control (i.e., cultured and differentiated for 5 days and then stimulated for 5 days). The luciferase activity of these control cells were measured as above. The EC$_{50}$ value (the concentration of test substance that can increase the amount of LPL mRNA expression over the control by 50%, unit: M) was calculated based on the straight line obtained by plotting the results of the tests performed using the test substances at varying concentrations. The maximum induction (Max. Ind. values) was calculated according to the following equation:

$$\text{Max. Ind. Value} = Lt/Lc$$

wherein Lt represents the maximum luciferase activity occurred in response to test substance stimulation; and Lc represents the value indicating the luciferase activity of the control.

The table 2 below shows the results (EC$_{50}$ values and Max. Ind. values) of using the compounds of the present invention as test substances, with the Example numbers representing by what Example methods the respective compounds were prepared.

TABLE 2

| Example | LPL Increase (Max. Ind. Values) | LPL Increase ($EC_{50}$ Values) |
| --- | --- | --- |
| 1 | 3.0 | 6.3 |
| 4 | 1.7 | 2.0 |
| 5 | 1.6 | 3.6 |
| 30 | 1.9 | 6.7 |
| 103 | 1.9 | 7.4 |
| 109 | 1.5 | 3.0 |
| 114 | 1.5 | 7.2 |
| 117 | 2.2 | 3.3 |
| 132 | 1.7 | 6.2 |
| 134 | 1.7 | 6.4 |
| 135 | 1.8 | 5.2 |
| 138 | 2.0 | 2.0 |

As shown in the table, the compounds of the present invention remarkably increase LPL mRNA expression. The results show that the compounds of the invention have excellent LPL increasing effects, even when compared with ethyl 4-[(4-bromo-2-cyanophenyl)carbamoyl]benzyl phosphonate, which is known to have LPL increasing effects and whose Max. Ind. Value is about 1.2.

Pharmacological Test 2

Test of Therapeutical Effect on Olive Oil-Induced Triglyceride Hyperlipidemia Models To conduct this test, 6-week-old SD rats (purchased from Charles River Japan) were used.

According to the body weight of the test rats when they were 5 weeks old, the test rats were divided into test groups and a control group with 6 rats per group.

A predetermined amount of each compound prepared in the Examples was measured and placed in an agate mortar. While 5% aqueous gum arabic solution was gradually introduced to the mortar, the compound was uniformly ground and suspended. Test samples were prepared by further adding 5% aqueous gum arabic solution gradually. Subsequently, these test samples were subjected to ultrasonic washing for 10 minutes to homogenize. Test samples were prepared as and when necessary.

The rats of the test groups were orally administered with the compounds of the invention such that rats received the compounds in an amount of 10, 30, or 100 mg/kg. The compounds of the invention were formulated as 5% gum arabic suspensions as described above.

The rats of the control group were orally administered with 5% aqueous gum arabic solution (not containing the compounds of the invention) in an amount of 5 ml/kg body weight. Administration was conducted once a day continuously for one week at a specific time of day after the rats reached 6 weeks of age. This test was performed under non-fasting conditions (rats had free access to feed and water), and the rats were fasted after the final administration of the compounds or 5% aqueous gum arabic solution.

Two hours after the final administration, olive oil was orally administered to the rats from both groups in an amount of 3 ml/kg body weight.

Two hours after the olive oil administration, blood was collected from the abdominal aorta of the rats of the respective groups using a heparinized syringe. The plasma was centrifugally separated from the blood at a temperature of 4° C., and the triglyceride level of the plasma was measured. A Hitachi 7170 automatic analyzer was used as the measuring instrument. Using the values measured from the test groups and control group, the decrease (%) in plasma triglyceride level was calculated according to the following equation:

Decrease (%) in plasma triglyceride concentration= $(1-E/C) \times 100$ wherein E represents the average plasma triglyceride level in each test group; and C represents the average plasma triglyceride level in the control group.

The table 3 below shows the results of administering the compounds of the invention prepared in the Examples in the amounts specified above.

TABLE 3

| Compounds of the present invention | Dosage (mg/kg) | Decrease in plasma triglyceride level (%) |
| --- | --- | --- |
| Example Compound 1 | 10 | 26 |
| | 30 | 50 |
| | 100 | 76 |
| Example Compound 10 | 10 | 48 |
| | 30 | 67 |
| | 100 | 74 |
| Example Compound 23 | 10 | 66 |
| | 30 | 78 |
| | 100 | 77 |
| Example Compound 58 | 10 | 31 |
| | 30 | 66 |
| | 100 | 79 |
| Example Compound 95 | 10 | 28 |
| | 30 | 65 |
| | 100 | 81 |

As is clear from the results shown in the table above, the compounds of the present invention decrease plasma triglyceride levels remarkably.

Pharmacological Test 3

Anti-Obesity Test Using Zucker Fatty Rats

Zucker fatty rats are obese rats discovered by Zucker et al., in 1961 as mutants among 13 M rats, which are a hybrid between 13C and M rats. These rats (fa/fa) start to appear distinctly obese from normal broods around the age of 3 weeks. As they age, the weight difference between the fatty rats and normal rats increases. Zucker fatty rats are currently kept by a variety of organizations as simple obesity models, and are readily obtainable.

This test was performed using this rat model to evaluate the anti-obesity action of the compounds of the invention. The preparation method of test samples and the test procedures are described below:

(1) Method for Preparing Test Samples

The test samples were prepared in the same manner as in Test Example 2.

(2) Test Procedures

Zucker fatty rats and lean rats (both from Charles River Japan) were purchased at the age of 5 weeks. They were divided into groups (10 rats per group) according to body weight when they reached 6 weeks old. After acclimatization, the administration of test samples was initiated when the rats reached 8 weeks old. Test samples were orally administered using an oral gavage so that the compounds of the invention contained in the test samples were given in an amount of 100 mg/kg body weight (test sample dosage: 5 ml/kg body weight). The test samples were administered once a day over 4 weeks at a specific time of day.

As a control, a group of rats were administered with the same amount of 5% aqueous gum arabic solution (5 ml/kg body weight) instead of the test samples.

The rats of all groups were weighed on the last day of administration. The average body weight of the rats of each test group was compared with the average body weight (standard weight) of the rats of the control group to obtain the weight variations (differences). The weight differences were expressed as percentages in relation to the standard weight.

The values thus calculated are referred to as "weight change %". When a weight difference is negative relative to the standard weight, weight change % is shown with "−" (minus).

During the test period, the rats of the respective groups had free access to rat feed ("CRF-1", manufactured by Oriental Yeast, Co., Ltd.) and water (tap water).

(3) Results

The table 4 below shows the results of the above-described test performed using as test samples compounds of the present invention prepared in the Examples.

TABLE 4

| Test Sample | Weight Change (%) |
| --- | --- |
| None (control) | 0 |
| Compound prepared in Example 1 | −8 |
| Compound prepared in Example 10 | −15 |
| Compound prepared in Example 58 | −19 |
| Compound prepared in Example 95 | −15 |

(4) Analysis

The results shown in the table above establish that the compounds of the invention tested exhibit excellent anti-obesity action.

Pharmacological Test 4
Anti-Obesity Test Using AKR Mice

The purpose of this test is to investigate whether the compounds of the invention inhibit the weight increase of food-induced-obesity model AKR/J mice, which are considered to be closer to humans. The model mice used in this test exhibit a correlation between body weight increase and blood leptin level increase, and therefore anti-obesity action can be determined in terms of both body weight decrease and leptin level decrease (see *J. Clin. Invest.* 99 (3), 1 Feb. 1997: 385-90).

Furthermore, this test enables the evaluation of therapeutic effects on diabetes. That is, it is reported that insulinemia can be observed in AKR/J mice when they are fed with a high-fat diet (see *Am. J. Physiol.* 266 (5 Pt 2), May 1994: R1423-8). It is thus known that insulinemia is strongly associated with diabetes (see, for example, *J. Cardiovasc. Nurs.* 16 (2), January 2002: 17-23). Therefore, this test can verify the therapeutic effects of the compounds of the present invention, used as test compounds, on diabetes.

The test was performed as described below:

For rat feed, powdered CRF-1 (Charles River Formula 1, manufactured by Oriental Yeast, Co., Ltd.) was used as normal feed. As high-fat feed, that prepared by blending CRF-1 with 18% safflower oil (Oriental Yeast, Co., Ltd.) was used.

Test substances were blended with the high-fat feed in an amount of 1 mg per gram of CRF-1.

AKR/J mice (from CLEA Japan, Inc.) were purchased at the age of 4 weeks. They were roughly divided into 2 groups according to body weight when the mice reached 5 weeks old. During this period, all mice were given the normal feed.

Subsequently, the mice of one group (8 mice) continued to be fed with the normal feed (normal feed group). The mice of the other group (8×(the number of the test substances+1) mice) were given the high-fat feed (high-fat feed group).

The body weight of the mice of each group was measured daily. When a notable increase was observed in body weight by comparing the body weight of the mice of the high-fat feed group with the body weight of the mice of the normal feed group, the mice of the high-fat feed group were further divided into groups (8 mice per group), and the feed (high-fat feed) that had been given to these mice was replaced by high-fat feeds containing the test substances. These mice were further reared for 7 weeks ("test substances+high-fat feed groups"; n=8 per type of test substance). Specifically, the administration of the test substances was continued for 7 weeks. A group of mice to which high-fat feed containing no test substance was continued to be given was used as a control (high-fat feed control group; n=8).

Four hours after the feeding on the last day of the 7-week test (the last day of the test), the body weight of the mice of the "test substances+high fat feed groups" was measured. Blood was collected from the abdominal aorta of the mice using a heparinized syringe, and the leptin and insulin levels in the plasma were measured using an Elisa kit (produced by Morinaga). The mice of the other groups (normal feed group and high-fat feed control group) were reared till the last day of the test as above, and 4 hours after the last feeding on the last day of the test the measurements were performed according to the same procedures.

The average values of the test results (body weight, leptin level, and insulin level) of the test substances+high-fat feed groups to which the compounds prepared in Examples (Examples 10 and 58) were used as test substances (hereinbelow referred to as the "Example Compound 10-mixed high-fat feed group" and "Example Compound 58-mixed high-fat feed group") were compared with the respective average values (standard values) of the results obtained from the mice of the high-fat control group to obtain the variations (differences). The differences were expressed as percentages in relation to the standard values. The values thus calculated were referred to as "weight change (%)", "leptin level change (%)", and "insulin level change (%)". In the table below, the symbols "−" (minus) indicate that the differences are negative relative to the standard values.

The table 5 shows the weight change (%), leptin level change (%), and insulin level change (%) of the mice of the Example Compound 10-mixed high-fat feed group, Example Compound 58-mixed high-fat feed group, normal feed group, and high-fat feed control group.

TABLE 5

| Test Group | Weight change (%) | Leptin level change (%) | Insulin level change (%) |
| --- | --- | --- | --- |
| High-fat feed control group | 0 | 0 | 0 |
| Example Compound 10-mixed high-fat feed group | −15 | −68 | −54 |
| Example Compound 58-mixed high-fat feed group | −10 | −55 | −12 |
| Normal feed group | −15 | −70 | −41 |

As is clear from the results shown in Table 36, the compounds of the present invention prepared in Examples 10 and 58 both have excellent anti-obesity action and an outstanding therapeutic effect on diabetes.

All the other compounds prepared in the Examples, which fall within the scope of the present invention, are consider to be able to attain results, from Pharmacological Tests 1 to 4, almost identical to those shown in Tables 33 to 36.

Pharmacological Test 5
Test for LPL Activity-Increasing Effect in Normal Rats 6-week-old SD rats (purchased from Charles River Japan) were used as subjects. The rats were divided into groups according to body weight at the age of 5 weeks. The rats in each test group were orally administered with a 5% gum arabic suspension in an amount of 5 ml/kg of body weight, the suspension containing the test compound of the invention in such an amount that the dose of the compound of the invention became 30 mg/kg of body weight in one group and 100 mg/kg of body weight in another group. The rats in a control group were orally administered with a 5% gum arabic suspension (not containing the test compound of the invention) in an amount of 5 ml/kg of body weight. Each sample suspension was orally administered every day at a specific time of day for 1 week starting when the rats reached the age of 6 weeks.

Four hours after the administration of the sample suspension, skeletal muscle tissues of the rats were collected, then freeze-clamped and stored under liquid nitrogen. LPL activity in the skeletal muscle tissues was measured by the following method.

Method of Measuring Skeletal Muscle LPL Activity
1) Preparation of Skeletal Muscle Tissue Extracts The soleus muscle was homogenized in a chilled solution of 0.05 mol/L $NH_4OH$—$NH_4Cl$ buffer (pH 8.5) containing 0.5 U/mL heparin at 1 mL/100 mg of tissue wet weight. After standing on ice for 60 min with vigorous mixing at intervals of 15 min, the homogenate was centrifuged at 3000 rpm and 4° C. for 10 min and the supernatant was separated.

2) Determination of Skeletal Muscle LPL Activity

The substrate solution was prepared by mixing 2 µCi of glycerol tri[1-$^{14}$C]oleate, 0.133 g of unlabeled triolein, 0.9 mL of 1% Triton X-100, and 0.9 mL of 4% bovine serum albumin. in 0.2 mol/L Tris-HCl buffer (pH 8.6) and 10.2 mL of 0.2 mol/L Tris-HCl buffer (pH 8.6). The mixture was emulsified by sonication on ice for 3 min.

In a glass test tube, 0.1 mL of the tissue extract, 0.05 mL of heat-inactivated rat serum and 0.15 mL of 4% bovine serum albumin in 0.2 mol/L Tris-HCl buffer (pH 7.4) were mixed. Enzyme reaction was started by adding 0.2 mL of the substrate solution and was carried out for 30 min. at 37° C.

The reaction was stopped by addition of 2 mL of 1.5 mol/L $H_2SO_4$/2-propanol (1:40, v/v), and 1 mL of distilled water and 3 mL of hexane were added into the test tube. After vigorously shaking for 10 min. at room temperature, the test tube was centrifuged for 10 min. at 3000 rpm.

The upper layer (3.5 mL) was collected in a new test tube and mixed with 1 mL of 0.1 mol/L KOH.

The test tube was vigorously shaken for 10 min. at room temperature and then centrifuged for 10 min. at 3000 rpm.

After removing the upper layer, 1 mL of the lower layer (water phase) was transferred into a vial for counting, neutralized with 50 µL of 1.3 mol/L HCl and mixed with 4 mL of scintillator. The radioactivity was measured using a liquid scintillation counter.

The LPL activity increase (%) was calculated from the measured values of LPL activity in the control group and test groups according to the following formula:

LPL activity increase (%)=(Test group average value)/(Control group average value)×100−100

The results are shown in a table 6 below.

TABLE 6

Result (Tissue LPL activity)

| Example | Dose | Increase of skeletal muscle LPL activity compared to control (%) |
|---|---|---|
|  | 30 mg/kg | 56 |
|  | 100 mg/kg | 75 |
| 10 | 30 mg/kg | 22 |
|  | 100 mg/kg | 55 |

TABLE 6-continued

Result (Tissue LPL activity)

| Example | Dose | Increase of skeletal muscle LPL activity compared to control (%) |
|---|---|---|
| 23 | 30 mg/kg | 18 |
|  | 100 mg/kg | 15 |
| 30 | 30 mg/kg | 22 |
|  | 100 mg/kg | 31 |
| 85 | 30 mg/kg | 9 |
|  | 100 mg/kg | 36 |
| 95 | 30 mg/kg | 13 |
|  | 100 mg/kg | 25 |

Examples of formulating the pharmaceutical preparations of the invention are described below:

Formulation Example 1

Preparation of Tablets

Using Example Compound 1 as an active ingredient, tablets (10000 tablets) each containing 300 mg of the active ingredient were prepared according to the following formulation:

| | |
|---|---|
| Example Compound 1 | 3000 g |
| Lactose (Japanese Pharmacopoeia) | 335 g |
| Corn starch (Japanese Pharmacopoeia) | 165 g |
| Carboxymethylcellulose calcium (Japanese Pharmacopoeia) | 125 g |
| Methylcellulose (Japanese Pharmacopoeia) | 60 g |
| Magnesium stearate (Japanese Pharmacopoeia) | 15 g |

Using the above formulation, Example Compound 1, lactose, corn starch and carboxymethylcellulose calcium were sufficiently mixed, the mixture was granulated using the methylcellulose aqueous solution, the granules were passed through a 24-mesh sieve and mixed with magnesium stearate, and the resulting mixture was pressed to form tablets.

Formulation Example 2

Preparation of Capsules

Using the Example Compound 95 as an active ingredient, hard gelatin capsules (10000 capsules) each containing 200 mg of the active ingredient were prepared according to the following formulation.

| | |
|---|---|
| Example Compound 95 | 2000 g |
| Crystalline cellulose (Japanese Pharmacopeia) | 300 g |
| Corn starch (Japanese Pharmacopeia) | 170 g |
| Talc (Japanese Pharmacopeia) | 20 g |
| Magnesium stearate (Japanese Pharmacopeia) | 10 g |

Using the above formulation, each ingredient was finely powdered and thoroughly mixed to give a uniform mixture. The desired capsules were then prepared by encapsulating the mixture into gelatin capsules having a size appropriate for oral administration.

The invention claimed is:
1. A method for activating LPL in a patient in need of LPL activation treatment, comprising administering an effective amount of a benzene compound into the patient, the benzene compound being represented by General Formula (1):

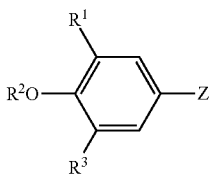

(1)

wherein $R^1$ is lower alkoxy; $R^2$, $R^3$ and Z are any one of the groups (1-1) to (1-3):

(1-1) $R^2$ is phenyl, phenyl having one or two halogen atoms as substituents on the benzene ring, phenyl lower alkyl group, phenyl lower alkyl group having on the benzene ring one or two substituents selected from the group consisting of halogen, and cyano, or $R^1$ and $R^2$ are jointed to form —CH═C(Ph)- (wherein Ph is phenyl); $R^3$ is hydrogen or lower alkoxy; and Z is a group represented by the formula below:

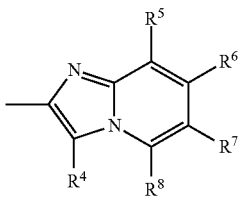

wherein $R^4$ is hydrogen, lower alkyl, or halogen;

$R^5$ is hydrogen, lower alkyl, halogen, hydroxy, lower alkoxy, phenyl lower alkoxy;

$R^6$ is hydrogen, lower alkyl, carboxy, or halogenated lower alkyl;

$R^7$ is hydrogen, lower alkyl, halogen, halogenated lower alkyl, lower alkoxycarbonyl, carboxy, cyano, carbamoyl, or phenyl; and $R^8$ is hydrogen or lower alkyl;

(1-2) $R^2$ is phenyl lower alkyl having one or two halogen atoms as substituents on the benzene ring: $R^3$ is hydrogen or lower alkoxy; and Z is imidazo[2,1-b]thiazol-6-yl or imidazo[2,1-b]thiazol-6-yl having one lower alkyl substituent; and (1-3) $R^2$ is phenyl lower alkyl, or phenyl lower alkyl having one or two halogen atoms as substituents on the benzene ring; $R^3$ is hydrogen or lower alkoxy; and Z is imidazo[1,2-a]pyridin-3-yl.

2. A method according to claim 1 wherein the benzene compound is a compound of General Formula (1), wherein $R^2$, $R^3$ and Z are the group (1-1).

3. A method according to claim 1 wherein the benzene compound is a compound of General Formula (1), wherein $R^2$, $R^3$ and Z are the group (1-2).

4. A method according to claim 1 wherein the benzene compound is a compound of General Formula (1), wherein $R^2$, $R^3$ and Z are the group (1-3).

5. A method according to claim 1 wherein the patient in need of LPL activation treatment is a hyperlipidemia patient.

6. A method according to claim 1 wherein the patient in need of LPL activation treatment is an obese patient.

7. A benzene compound represented by General Formula (1a)

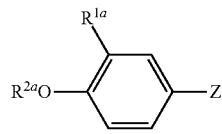

(1a)

wherein $R^{1a}$ is lower alkoxy; and $R^{2a}$ and Z are any one of groups (2-1) to (2-3):

(2-1) $R^{2a}$ is phenyl lower alkyl having one or two halogen atoms as substituents on the benzene ring; and Z is imidazo[2,1-b]thiazol-6-yl or imidazo[2,1-b]thiazol-6-yl having one lower alkyl substituent;

(2-2) $R^{2a}$ is phenyl lower alkyl or phenyl lower alkyl having one or two halogen atoms as substituents on the benzene ring; and Z is imidazo[1,2-a]pyridin-3-yl;

(2-3) $R^{2a}$ is phenyl, phenyl having one or two halogen atoms as substituents on the benzene ring, phenyl lower alkyl group having on the benzene ring one or two substituents selected from the group consisting of halogen, and cyano, or $R^{1a}$ and $R^{2a}$ are jointed to form —CH═C(Ph)- (wherein Ph is phenyl); and Z is a group represented by the formula below:

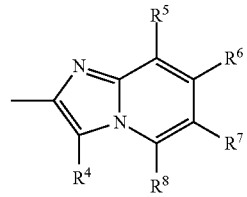

wherein $R^4$ is hydrogen, lower alkyl, or halogen;

$R^5$ is hydrogen, lower alkyl, halogen, hydroxy, lower alkoxy, phenyl lower alkoxy;

$R^6$ is hydrogen, lower alkyl, carboxy, or halogenated lower alkyl;

$R^7$ is hydrogen, lower alkyl, halogen, halogenated lower alkyl, lower alkoxycarbonyl, carboxy, cyano, carbamoyl, or phenyl; and $R^8$ is hydrogen or lower alkyl.

* * * * *